United States Patent
Milstein et al.

(10) Patent No.: US 6,348,207 B1
(45) Date of Patent: Feb. 19, 2002

(54) ORALLY DELIVERABLE SUPRAMOLECULAR COMPLEX

(75) Inventors: Sam J. Milstein, Larchmont; Evgueni Barantsevitch, New Rochelle, both of NY (US); Andrea Leone-Bay, Ridgefield, CT (US); Nai Fang Wang, Long Island City, NY (US); Donald J. Sarubbi, Bronxville, NY (US); Noemi B Santiago, Hawthorne, NY (US)

(73) Assignee: Emisphere Technologies, Inc., Tarrytown, NY (US)

( * ) Notice: Subject to any disclaimer, the term of this patent is extended or adjusted under 35 U.S.C. 154(b) by 0 days.

(21) Appl. No.: 08/941,609

(22) Filed: Sep. 30, 1997

Related U.S. Application Data

(63) Continuation of application No. 08/328,932, filed on Oct. 25, 1994, now Pat. No. 5,714,167, which is a continuation-in-part of application No. 08/051,019, filed on Apr. 22, 1993, now Pat. No. 5,451,410, which is a continuation-in-part of application No. 08/168,776, filed on Dec. 16, 1993, now Pat. No. 5,447,728, which is a continuation-in-part of application No. 08/051,019, and a continuation-in-part of application No. 08/143,571, filed on Oct. 26, 1993, now abandoned, which is a continuation-in-part of application No. 08/076,803, filed on Jun. 14, 1993, now Pat. No. 5,578,323, which is a continuation-in-part of application No. 07/920,346, filed on Jul. 27, 1992, now Pat. No. 5,443,841, which is a continuation-in-part of application No. 07/898,909, filed on Jun. 15, 1992, now abandoned, and a continuation-in-part of application No. PCT/US94/04560, filed on Apr. 22, 1994, said application No. 08/051,019, is a continuation-in-part of application No.08/205,511, filed on Mar. 2, 1994, now Pat. No. 5,792,451, which is a continuation-in-part of application No. 08/231,622, filed on Apr. 22, 1994, now Pat. No. 5,629,020, and a continuation-in-part of application No. 08/231,623, filed on Apr. 22, 1994, now Pat. No. 5,541,155, and a continuation-in-part of application No. 08/315,200, filed on Sep. 29, 1994, now Pat. No. 5,693,338, and a continuation-in-part of application No. 08/316,404, filed on Sep. 30, 1994.

(51) Int. Cl.[7] .......................... A01N 25/12; A61K 9/14
(52) U.S. Cl. ...................... 424/408; 424/409; 424/489; 424/498; 424/499; 424/451; 424/464; 424/470
(58) Field of Search .................................. 424/489, 409, 424/470, 490, 498, 451, 488, 464, 491, 408, 499

(56) References Cited

U.S. PATENT DOCUMENTS 2,671,451 A    3/1954   Bolger ........................ 128/260

(List continued on next page.)

FOREIGN PATENT DOCUMENTS

CA    1077842    8/1976    ............ A61K/9/50

(List continued on next page.)

OTHER PUBLICATIONS

Andini, S. et al., (1975) *Origins of Life*, vol. 6, pp. 147–153.

(List continued on next page.)

*Primary Examiner*—Thurman K. Page
*Assistant Examiner*—W. Benston
(74) *Attorney, Agent, or Firm*—Darby & Darby

(57) ABSTRACT

Methods for transporting a biologically active agent across a cellular membrane or a lipid bilayer. A first method includes the steps of:

Figure 1:
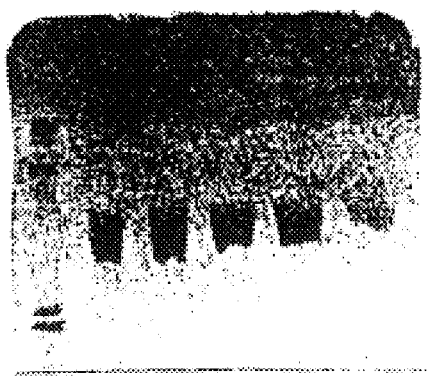

(a) providing a biologically active agent which can exist in a native conformational state, a denatured conformational state, and an intermediate conformational state which is reversible to the native state and which is conformationally between the native and denatured states;

(b) exposing the biologically active agent to a complexing perturbant to reversibly transform the biologically active agent to the intermediate state and to form a transportable supramolecular complex; and (c) exposing the membrane or bilayer to the supramolecular complex, to transport the biologically active agent across the membrane or bilayer. The perturbant has a molecular weight between about 150 and about 600 daltons, and contains at least one hydrophilic moiety and at least one hydrophobic moiety. The supramolecular complex comprises the perturbant noncovalently bound or complexed with the biologically active agent. In the present invention, the biologically active agent does not form a microsphere after interacting with the perturbant. A method for preparing an orally administrable biologically active agent comprising steps (a) and (b) above is also provided as are oral delivery compositions. Additionally, mimetics and methods for preparing mimetics are contemplated.

37 Claims, 31 Drawing Sheets

U.S. PATENT DOCUMENTS

| | | | |
|---|---|---|---|
| 2,828,206 A | 3/1958 | Rosenberg | 99/2 |
| 2,862,918 A | 12/1958 | Meyer et al. | 260/123.5 |
| 2,868,740 A | 1/1959 | Luce | 260/8 |
| RE24,899 E | 11/1960 | Green | |
| 2,971,916 A | 2/1961 | Schleicher et al. | 252/62.5 |
| 3,016,308 A | 1/1962 | Macaulay | 177/37 |
| 3,052,655 A | 9/1962 | Fox et al. | 260/78 |
| 3,057,344 A | 10/1962 | Abella et al. | 128/2 |
| 3,076,790 A | 2/1963 | Fox et al. | 260/78 |
| 3,170,802 A | 2/1965 | Fukushima | 99/145 |
| 3,190,837 A | 6/1965 | Brynko et al. | 252/316 |
| 3,474,777 A | 10/1969 | Figge et al. | 128/2 |
| 3,491,093 A | 1/1970 | Pachter et al. | 260/247.5 |
| 3,565,559 A | 2/1971 | Sato | 424/37 |
| 3,567,650 A | 3/1971 | Bakan | 252/316 |
| 3,574,832 A | 4/1971 | Engel et al. | 424/183 |
| 3,576,758 A | 4/1971 | Emrick | 252/316 |
| 3,687,926 A | 8/1972 | Arima et al. | 260/112.5 |
| 3,725,113 A | 4/1973 | Chang | 117/82 |
| 3,748,277 A | 7/1973 | Wagner | 252/316 |
| 3,794,561 A | 2/1974 | Matsukawa et al. | 195/29 R |
| 3,795,739 A | 3/1974 | Birkmayer et al. | 424/274 |
| 3,816,404 A | 6/1974 | Kablaoui et al. | 260/239.3 |
| 3,822,348 A | 7/1974 | Higashi et al. | 424/95 |
| 3,849,550 A | 11/1974 | Teitelbaum | 424/78 |
| 3,933,873 A | 1/1976 | Love et al. | 260/239.3 |
| 3,937,668 A | 2/1976 | Zolle | 252/316 |
| 3,939,253 A | 2/1976 | Bodor et al. | 424/309 |
| 3,956,172 A | 5/1976 | Saeki et al. | 252/316 |
| 3,962,416 A | 6/1976 | Katzen | 424/19 |
| 3,976,773 A | 8/1976 | Curran | 424/250 |
| 4,035,507 A | 7/1977 | Bodor et al. | 424/311 |
| 4,048,268 A | 9/1977 | Ludwig | 264/15 |
| 4,061,466 A | 12/1977 | Sjoholm et al. | 23/230 B |
| 4,117,801 A | 10/1978 | Dannelly et al. | 118/20 |
| 4,147,767 A | 4/1979 | Yapel | 424/22 |
| 4,183,849 A | 1/1980 | Hansen | 260/112.7 |
| 4,199,561 A | 4/1980 | Roth et al. | 424/32 |
| 4,217,370 A | 8/1980 | Rawlings et al. | 426/98 |
| 4,238,506 A | 12/1980 | Stach et al. | 424/319 |
| 4,239,635 A | 12/1980 | Rieder | 252/34 |
| 4,239,754 A | 12/1980 | Sache et al. | 424/183 |
| 4,272,506 A | 6/1981 | Schwarzberg | 424/8 |
| 4,289,759 A | 9/1981 | Heavner et al. | 424/177 |
| 4,345,588 A | 8/1982 | Widder et al. | 128/1.3 |
| 4,348,384 A | 9/1982 | Horikoshi et al. | 424/101 |
| 4,351,337 A | 9/1982 | Sidman | 128/260 |
| 4,352,883 A | 10/1982 | Lim | 435/178 |
| 4,357,259 A | 11/1982 | Senyei et al. | 252/316 |
| 4,388,304 A | 6/1983 | Nyeki et al. | 424/177 |
| 4,393,192 A | 7/1983 | Curatolo et al. | 528/292 |
| 4,402,856 A | 9/1983 | Schnoring et al. | 428/402.22 |
| 4,402,968 A | 9/1983 | Martin | 424/273 |
| 4,405,598 A | 9/1983 | Brown | 424/45 |
| 4,442,090 A | 4/1984 | Kakeya et al. | 424/178 |
| 4,446,138 A | 5/1984 | Pack | 424/248.57 |
| 4,450,150 A | 5/1984 | Sidman | 424/1.1 |
| 4,457,907 A | 7/1984 | Porter | 424/7.1 |
| 4,460,563 A | 7/1984 | Calanchi | 424/35 |
| 4,462,839 A | 7/1984 | McGinley et al. | 106/198 |
| 4,462,991 A | 7/1984 | Higuchi et al. | 424/177 |
| 4,473,620 A | 9/1984 | Wu et al. | 428/402.24 |
| 4,483,807 A | 11/1984 | Asano | 264/22 |
| 4,492,684 A | 1/1985 | Goosen et al. | 424/19 |
| 4,518,433 A | 5/1985 | McGinley et al. | 106/180 |
| 4,590,265 A | 5/1986 | Bogan et al. | 536/63 |
| 4,608,278 A | 8/1986 | Frank | 427/213.35 |
| 4,613,500 A | 9/1986 | Suzuki et al. | 429/85 |
| 4,647,455 A | 3/1987 | De Bold | 424/95 |
| 4,666,641 A | 5/1987 | Fickat et al. | 264/4.3 |
| 4,671,954 A | 6/1987 | Goldberg | 424/450 |
| 4,673,566 A | 6/1987 | Goosen et al. | 424/19 |
| 4,683,092 A | 7/1987 | Tsang | 264/4.3 |
| 4,690,786 A | 9/1987 | Ninomiya et al. | 264/4.6 |
| 4,692,284 A | 9/1987 | Braden | 264/4.3 |
| 4,692,433 A | 9/1987 | Hostetler et al. | 514/12 |
| 4,703,042 A | 10/1987 | Bodor | 514/56 |
| 4,708,952 A | 11/1987 | Salatinjants | 514/158 |
| 4,745,161 A | 5/1988 | Saudek et al. | 525/420 |
| 4,753,007 A | 6/1988 | Iaccheri et al. | 424/491 |
| 4,757,007 A | 7/1988 | Satoh | 435/69 |
| 4,757,024 A | 7/1988 | Roper | 436/507 |
| 4,757,066 A | 7/1988 | Shiokari et al. | 514/210 |
| 4,766,012 A | 8/1988 | Valenti | 427/213.36 |
| 4,774,320 A | 9/1988 | Tagliabue et al. | 530/328 |
| 4,789,734 A | 12/1988 | Piesrchbacher | 530/395 |
| 4,835,312 A | 5/1989 | Itoh et al. | 564/205 |
| 4,837,381 A | 6/1989 | Steber et al. | 424/502 |
| 4,844,904 A | 7/1989 | Hamaguchi et al. | 424/450 |
| 4,873,087 A | 10/1989 | Morishita et al. | 424/433 |
| 4,878,942 A | 11/1989 | Motegi et al. | |
| 4,886,663 A | 12/1989 | Houghten | 424/88 |
| 4,895,725 A | 1/1990 | Kantor et al. | 424/455 |
| 4,897,444 A | 1/1990 | Brynes et al. | 525/54.1 |
| 4,900,730 A | 2/1990 | Miyauchi | 514/12 |
| 4,908,233 A | 3/1990 | Takizawa et al. | 427/213.35 |
| 4,919,939 A | 4/1990 | Baker | 424/493 |
| 4,925,673 A | 5/1990 | Steiner | 424/455 |
| 4,927,928 A | 5/1990 | Shroot et al. | |
| 4,963,364 A | 10/1990 | Fox et al. | 424/455 |
| 4,976,968 A | 12/1990 | Steiner | 424/491 |
| 4,983,402 A | 1/1991 | Steiner | 424/491 |
| 4,996,292 A | 2/1991 | Fox et al. | 528/328 |
| 5,019,400 A | 5/1991 | Gombotz et al. | 424/497 |
| 5,023,374 A | 6/1991 | Simon | 564/152 |
| 5,039,481 A | 8/1991 | Pacifici et al. | 422/4 |
| 5,041,291 A | 8/1991 | Bader et al. | 424/426 |
| 5,055,300 A | 10/1991 | Gupta | 424/409 |
| 5,066,487 A | 11/1991 | Morelle et al. | 424/68 |
| 5,067,961 A | 11/1991 | Kelman et al. | 623/5 |
| 5,069,936 A | 12/1991 | Yen | 427/213.33 |
| 5,077,278 A | 12/1991 | Hafner et al. | 514/30 |
| 5,100,669 A | 3/1992 | Hyon et al. | 424/426 |
| 5,100,918 A | 3/1992 | Sunshine et al. | 514/557 |
| 5,122,367 A | 6/1992 | Ron et al. | 424/80 |
| 5,126,147 A | 6/1992 | Silvestri et al. | 424/497 |
| 5,137,892 A | 8/1992 | Chu et al. | 514/278 |
| 5,186,947 A | 2/1993 | Goettsche et al. | 424/638 |
| 5,204,099 A | 4/1993 | Barbier et al. | 424/401 |
| 5,206,384 A | 4/1993 | Shibahara et al. | 548/537 |
| 5,216,124 A | 6/1993 | Hansen, Jr. et al. | 530/317 |
| 5,244,653 A | 9/1993 | Berke et al. | 424/70 |
| 5,250,236 A | 10/1993 | Gasco | 264/4.4 |
| 5,271,934 A | 12/1993 | Goldberg et al. | 424/401 |
| 5,271,961 A | 12/1993 | Mathiowitz et al. | 427/213.31 |
| 5,278,148 A | 1/1994 | Branca et al. | 514/19 |
| 5,310,535 A | 5/1994 | Kruper, Jr. et al. | 424/1.53 |
| 5,328,992 A | 7/1994 | Peter et al. | 534/116 |
| 5,352,461 A | 10/1994 | Feldstein et al. | 424/493 |
| 5,384,133 A | 1/1995 | Boyes et al. | 424/501 |
| 5,389,377 A | 2/1995 | Chagnon et al. | 424/450 |
| 5,389,379 A | 2/1995 | Dirix et al. | 424/451 |
| 5,401,516 A | 3/1995 | Milstein et al. | 424/491 |
| 5,418,010 A | 5/1995 | Janda et al. | 427/213.31 |
| 5,439,686 A | 8/1995 | Desai et al. | 424/451 |
| 5,443,841 A | 8/1995 | Milstein et al. | 424/451 |
| 5,447,728 A | 9/1995 | Milstein et al. | 424/490 |
| 5,451,410 A | 9/1995 | Milstein et al. | 424/490 |
| 5,474,997 A | 12/1995 | Gray et al. | 514/252 |
| 5,536,813 A | 7/1996 | Charpenel et al. | 530/324 |
| 5,540,939 A | 7/1996 | Milstein et al. | 424/491 |

| | | | |
|---|---|---|---|
| 5,541,155 A | 7/1996 | Leone-Bay et al. ............. | 514/2 |
| 5,578,323 A | 11/1996 | Milstein et al. .............. | 424/499 |
| 5,601,846 A | 2/1997 | Milstein et al. .............. | 424/499 |
| 5,629,020 A | 5/1997 | Leone-Bay et al. ......... | 424/489 |
| 5,643,957 A | 7/1997 | Leone-Bay et al. ......... | 514/563 |
| 5,650,386 A | 7/1997 | Leone-Bay et al. ............. | 514/2 |
| 5,665,700 A | 9/1997 | Cho et al. ...................... | 514/2 |
| 5,667,806 A | 9/1997 | Kantor ....................... | 424/484 |
| 5,714,167 A | 2/1998 | Milstein et al. ............... | 424/90 |

FOREIGN PATENT DOCUMENTS

| | | | |
|---|---|---|---|
| DE | 2 424 169 | 12/1974 | ............ A61K/9/00 |
| DE | 2 343 037 | 3/1975 | |
| DE | 3 202 255 | 10/1982 | ........... C08L/89/00 |
| DE | 3 612 102 | 10/1986 | ........... C07K/15/00 |
| EP | 0 000 667 A1 | 2/1979 | ............ A61K/9/50 |
| EP | 0 036 145 A1 | 9/1981 | .......... A61K/31/62 |
| EP | 0 068 341 | 1/1983 | .......... A61K/31/16 |
| EP | 0 105 804 | 4/1984 | ........... C12N/15/00 |
| EP | 0 130 162 A2 | 1/1985 | ............ B01J/13/02 |
| EP | 0 170 540 A1 | 2/1986 | .......... A61K/9/52 |
| EP | 226223 A2 | 6/1987 | ........ C07C/103/46 |
| EP | 0 342 054 A2 | 11/1989 | ............ A61K/7/06 |
| EP | 0 342 056 A2 | 11/1989 | ............ A61K/7/06 |
| EP | 0 365 183 | 4/1990 | .......... A61K/31/18 |
| EP | 0 366 277 | 5/1990 | .......... A61K/9/107 |
| EP | 0 418 642 | 3/1991 | .......... A61K/37/30 |
| EP | 0 448 057 | 9/1991 | ........... C12P/21/08 |
| EP | 0 452 161 | 10/1991 | ............ A61K/7/48 |
| EP | 0 459 795 | 12/1991 | .......... A61K/37/02 |
| EP | 0 467 389 | 1/1992 | .......... A61K/9/52 |
| EP | 0 490 549 A1 | 6/1992 | .......... A61K/47/12 |
| EP | 0 517 211 A1 | 9/1992 | .......... A61K/47/12 |
| EP | 0 616 799 A1 | 9/1994 | ............ A61K/7/00 |
| ES | 369853 | 7/1969 | |
| FR | 1 351 358 | 3/1964 | |
| FR | 1 468 601 | 2/1967 | |
| FR | 2 133 926 | 12/1972 | .......... A61K/27/00 |
| FR | 2 326 934 | 5/1977 | .......... A61K/47/00 |
| FR | 2 565 102 | 12/1985 | ............ A61K/9/52 |
| GB | 929401 | 6/1963 | |
| GB | 1 075 952 | 8/1967 | |
| GB | 1 236 885 | 6/1971 | |
| GB | 1 567 763 | 5/1980 | ............ A61K/9/22 |
| GB | 2 095 994 | 10/1982 | ............ A61K/9/00 |
| IL | 71258/2 | 12/1987 | |
| JP | 48-24246 | 3/1973 | |
| JP | 56-68612 | 6/1981 | .......... A61K/31/19 |
| JP | 58-35111 | 3/1983 | ............ A61K/9/66 |
| JP | 6-107682 | 4/1994 | |
| NL | 208826 | 12/1964 | |
| NL | 280825 | 12/1964 | |
| NO | B-146698 | 11/1982 | .......... A61K/37/26 |
| WO | WO 85/00105 | 1/1985 | ............ A61K/9/52 |
| WO | 85/00110 | 1/1985 | .......... A61K/47/00 |
| WO | WO 85/00809 | 2/1985 | ........ C07D/233/64 |
| WO | WO 87/04076 | 7/1987 | .......... A61K/45/02 |
| WO | WO 88/01213 | 2/1988 | ............ B23B/5/16 |
| WO | WO 92/19263 | 12/1992 | .......... A61K/39/00 |
| WO | WO 93/18754 | 9/1993 | ............ A61K/9/16 |
| WO | WO 93/25583 | 12/1993 | ........... C07K/15/00 |
| WO | WO 94/11015 | 5/1994 | .......... A61K/37/00 |
| WO | WO 94/14420 | 7/1994 | ............ A61K/9/16 |
| WO | WO 94/18950 | 9/1994 | .......... A61K/9/127 |
| WO | WO 94/18997 | 9/1994 | .......... A61K/37/00 |
| WO | WO 94/21234 | 9/1994 | |
| WO | WO 94/23702 | 10/1994 | ............ A61K/9/16 |
| WO | WO 94/23767 | 10/1994 | ............ A61L/9/16 |
| WO | WO 94/24291 | 10/1994 | ......... A61K/39/015 |
| WO | WO 94/28878 | 12/1994 | ............ A61K/9/14 |
| WO | WO 95/11690 | 5/1995 | .......... A61K/37/00 |
| WO | WO 85/02772 | 7/1995 | .......... A61K/49/00 |
| WO | WO 95/28839 | 11/1995 | .......... A01N/37/46 |
| WO | WO 95/28920 | 11/1995 | .......... A61K/31/19 |
| WO | WO 96/12473 | 5/1996 | ............ A61K/9/16 |
| WO | WO 96/12474 | 5/1996 | ............ A61K/9/16 |
| WO | WO 96/12475 | 5/1996 | ............ A61K/9/16 |
| WO | WO 96/21464 | 7/1996 | .......... A61K/39/00 |
| WO | WO 96/30063 | 10/1996 | .......... A61K/38/00 |
| WO | WO 96/33699 | 10/1996 | ............ A61K/9/16 |
| WO | WO 96/39835 | 12/1996 | .......... A01N/43/50 |
| WO | WO 96/40070 | 12/1996 | ............ A61K/9/14 |
| WO | WO 96/40076 | 12/1996 | ............ A61K/9/16 |
| WO | WO 97/10197 | 3/1997 | .......... C07C/51/10 |
| WO | WO 97/31938 | 9/1997 | ............ C07K/5/00 |
| WO | WO 97/36480 | 10/1997 | .......... A01N/37/12 |
| WO | 97/47270 | 12/1997 | |

OTHER PUBLICATIONS

Brooke, S.1 et al. (1977) *BioSystems,* vol. 9, pp. 1–22.
Chen et al. (1975) "Evidence for Hemiacetal Formation", *Biochemistry,* vol. 18, No. 5, pp. 921–925.
Davis et al. (1983) "Leucinal Inhibits . . . ", *Pharmacology Biochemistry Behavior,* vol. 19, pp. 791–794.
Dose, K. (1974) *Origins of Life,* vol. 5, pp. 239–252.
Fasman et al. (1964) *Biochemistry,* vol. 3, No. 11, pp. 1665–1674.
Fox, S.W. et al. (1976) *BioSystems,* vol. 8, pp. 40–44.
Fox, S.W. et al., *Molecular Evolution and the Origin of Life,* Maxel Decker, New York (1977).
Fox, S.W. et al. (1968) *Biochim. Biophys. Acta,* vol. 160, pp. 246–249.
Fox, S.W. (1976) *Origins of Life,* vol. 7, pp. 49–68.
Fox, S.W. (1980) *Naturwissenschaften,* vol. 67, pp. 378–383.
Fox, S.W. et al. (1960) *Archives of Biochemistry and Biophysics,* vol. 86, pp. 281–285.
Fox, S.W. et al. (1974) *Origins of Life,* vol. 5, pp. 227–237.
Fox, S.W. (1984) *Origins of Life,* vol. 14, pp. 485–488.
Gol'dovskii, A.M. (1978) *Zhurnal Evolyutsionnoi Biokhimii i Fiziologii,* vol. 14(6), pp. 437–439.
Gurrieri, S. et al. (1973) *Thermochimica Acta,* vol. 7, pp. 231–239.
Harada, K. et al. (1979) *BioSystems,* vol. 11, pp. 47–53.
Harada et al., (1960) *Archives of Biochemistry and Biophysics,* vol. 86, pp. 274–280.
Hare (1970) *Etude Cenetique De La Polycondensation Thermique D'$_X$–Amino Acides,* vol. 45, pp. 330–339.
Heinrich, M.R. et al. (1969) *Archives of Biochemistry and Biophysics,* vol. 130, pp. 441–448.
Heinz, B. et al. (1981) *BioSystems,* vol. 14, pp. 33–40.
Hennon, G. et al. (1975) *Biochimie,* vol. 57, pp. 1395–1396.
Hsu, L.L. et al. (1976) *BioSystems,* vol. 8, pp. 89–101.
Hsu, L.L. et al. (1971) *Currents in Modern Biology,* vol. 4, pp. 12–25.
Ishima, Y. et al. (1981), *BioSystems,* vol. 14, pp. 243–251.
Jackson et al. (1991) "Pharmacological . . . ", *J. Pharm. & Exp. Thera.,* vol. 261, No. 1, pp. 546–552.
Jungck, J.R. et al. (1973) *Naturwissenschaften,* vol. 60, pp. 425–427.
Kokufuta, E. et al. (1984) *BioSystems,* vol. 16, pp. 175–181.
Krampitz, G. et al. (1967) *Naturwissenschaften,* pp. 516–517.
Krampitz, G. et al. (1968) *Naturwissenschaften,* pp. 345 and 346.
Krampitz, G. et al. (1966) *Naturwissenschaften,* pp. 7 and 8.
Lacey, Jr., J.C. et al. (1979) *BioSystems,* vol. 11, pp. 9–17.

Lacey, Jr., J.C. et al. (1979) *BioSystems,* vol. 11, pp. 1–7.
Martinez Luque–Romero, M. et al. (1986), *BioSystems,* vol. 19, pp. 267–272.
Masinovsky, Z. et al. (1989) *BioSystems,* vol. 22, pp. 305–310.
Matsuno, K. (1982) *BioSystems,* vol. 15, pp. 1–11.
Matsuno, K. (1984) *BioSystems,* vol. 17, pp. 11–14.
Matsuno, K. (1981) *BioSystems,* vol. 14, pp. 163–170.
McAlhaney, W.W. et al. (1976) *BioSystems,* vol. 8, pp. 45–50.
Melius, P. et al. (1987) *BioSystems,* vol. 20, pp. 213–217.
Melius, P. et al. (1975) *Bioorganic Chemistry,* vol. 4, pp. 385–391.
Melius, P. (1979) *BioSystems,* vol. 11, pp. 125–132.
Miquel, J. et al. (1971) *Currents in Modern Biology,* vol. 3, pp. 299–306.
Nakashima, T. et al. (1980) *J. Mol. Evol.,* vol. 15, pp. 161–168.
Nakashima, T. et al. (1981) *BioSystems,* vol. 14, pp. 151–161.
Novak, V.J.A. (1984) *Origins of Life,* vol. 14, pp. 513–522.
Olafsson, P.G. et al. (1971) *Polymer Letters,* vol. 9, pp. 521–528.
Phillips, R.D. et al. (1974) *Int. J. Peptide Protein Res.,* vol. 6, pp. 309–319.
Przbylski, A.T. et al. (1982) *Die Naturwissenschaften,* vol. 69, pp. 561–563.
Przybylski, A.T. et al. (1984) *Applied Biochemistry and Biotechnology,* vol. 10, pp. 301–307.
Przybylski, A.T. (1985) *BioSystems,* vol. 17, pp. 281–288.
Rohlfing, D.L. (1975) *Origins of Life,* vol. 6, pp. 203–209.
Rohlfing, D.L. (1970) *Science,* vol. 169, pp. 998–1000.
Rohlfing, D.L. (1967) *Archives of Biochemistry and Biophysics,* vol. 118, pp. 468–474.
Rohlfing, D.L. et al. *Catalytic Activities of Thermal Polyanhydro–α–Amino Acids,* pp. 373–418, 1969.
Rohlfing, D.L. et al. (1976) *BioSystems,* vol. 8, pp. 139–145.
Ryan, J.W. et al. (1973) *BioSystems,* vol. 5, pp. 115–118.
Saunders, M.A. et al. (1974) *BioSystems,* vol. 6, pp. 81–92.
Snyder, W.D. et al. (1975) *BioSystems,* vol. 7, pp. 222–229.
Sokol, P.E. (1974) *Journal of the American Oil Chemists'Society,* vol. 52, pp. 101–102.
Tschager et al. (1988) *Milchwirtschaftliche Berichte,* vol. 95, pp. 79–83.
Vaughan, G. et al. (1987) *BioSystems,* vol. 20, pp. 219–223.
Vol'kenshtein, M.V. (1989) *Molekulyarnaya Biologiya,* vol. 23(1), pp. 23–37.
Waehneldt, T.V. et al. (1968) *Biochim. Biophys. Acta,* vol. 160, pp. 239–245.
Williams et al. (1991) *J. Biol. Chem.,* vol. 266, No. 8, pp. 5182–5190.
Yuki, A. et al. (1969) *Biochemical and Biophysical Research Communications,* vol. 36(4), pp. 657–663.
Zulaski et al. (1983) "New Carboxyalkyl Inhibitors of Brain Enkenphalinase", *J. Med. Chem.,* 26, pp. 60–65.
(1985) *Chemical Abstracts,* vol. No. 105(1), Abstract No. 12027p.
(1985) *Chemical Abstracts,* vol. No. 102(6), Abstract No. 50870d.
*Chemical Abstract,* vol. 80(9) Abst. No. 52392a.
Bergeron, Raymond J., et al. (1994) "Macromolecular Self–Assembly of Diketopiperazine Tetrapeptides", *Journal of the American Chemical Society,* vol. 116, pp. 8479–8484.

Bergeron, Raymond J., et al. (1993) "A Comparative Study of the Iron–Clearing Properties of Desferrithiocin Analogues With Desferrioxamine B in a Cebus Monkey Model", *Blood,* vol. 81, No. 8, pp. 2166–2173.
Bergeron, Raymond J., et al. (1992) "A Comparison of the Iron–Clearing Properties of 1,2–Dimethyl–3–Hydroxypyrid–4–One, 1,2–Diethyl–3–Hydroxypyrid–4–One, and Deferoxamine", *Blood,* vol. 79, No. 7, pp. 1882–1890.
Bergeron, Raymond J., et al. (1991) "Evaluation of Desferrithiocin and Its Synthetic Analogs as Orally Effective Iron Chelators", *Journal of Medicinal Chemistry,* vol. 34, No. 7, pp. 2072–2078.
Bergeron, Raymond et al., "A Comparative Evaluation of Iron Clearance Models", *Annals New York Academy of Sciences,* pp. 278–393, Mar. 13–15, 1990.
Andriuoli, G., et al. (1990), *Haemostasis* 20 (suppl. 1):154–158.
Caramazza, I., et al. (1991), *Thrombosis Research* 62:785–789.
Guarini, S., et al. (1983) *Experimentia* 41:350–352.
Guarini, S., et al. (1985), *Pharmacological Research Communications* 17(8):685–697.
Dal Pozzo, A., et al. (1989), *Thrombosis Research* 56:119–124.
Gelb, R., et al (1983), *Lite Sciences* 33(1):83–85.
Watterberg et al. (1988), *Pediatric Research,* vol. 23, No. 4, part 2 , p. 570A, col. 1, abstract No. 2209.
Bernstein (1985), *Chest* 87(1):68S–73S.
Damge et al. (1988), *Diabetes* 37:246–251.
*Chemical Abstracts:* 83 184360k, (1975).
Amino, Y., et al., *Chem. Pharm. Bull.* 36(11):4426–4434 (1988).
Baughman, R.A. et al., *Proc. of the 6th Inter'l. Symp. on Recent Advs. in Drug Delivery Systems, Ctr for Controlled Chem. Delivery,* University of Utah, Feb. 22–25, 1993, Salt Lake City, UT, pp. 179–180 "Method for Assessing The Stability of Proteinoid Microspheres".
Haas, S. et al., "Assessment Of Stability Of Proteinoid Microspheres", *Proceed. Intern. Symp. Control. Rel. Bioact. Mater.,* 20 (1993), Controlled Research Society, Inc.
X. Ma, et al., *Proceed. Intern. Symp. Control. Rel. Bioact. Mater.,* 20 (1993), Controlled Release Society, Inc. "In Vitro Mechanistic Investigation of the Proteinoid Microsphere Oral Delivery System".
Yen, H.–R H., et al., "Adsorption of Sulforhodamine 101 on Proteinoid Microspheres" *Proceed. Intern. Symp. Control. Rel. Bioact. Mater.,* 20 (1993), Controlled Release Society, Inc.
Presented at *"IBC Rational Drug Design Conference",* San Diego, Calif.—Dec. 1994.
Leone–Bay et al., Presented at *"Winter Conference on Medicinal and Bioorganic Chemistry"* Steamboat Springs, Colorado—Feb. 1995 "Microsphere Formation and Drug Delivery in a Series of Derivatized Amino Acids".
Santiago et al., *Pharm. Res.* 11: 1994, p. S–298 "Oral Delivery of Heparin Microspheres made with Modified Amino Acids".
Leone–Bay et al., *Pharm. Res.* 11: 1994, p. S–121 "Oral Delivery of Heparin using Acylated Amino Acids".
Sarubbi et al., *Pharm. Res.* 11: 1994, p. S–299 "Oral Calcitonin Delivery using the PODDS Technology".
Leipold et al., *Pharm. Res.* 11: 1994, p. S–298 "Oral Delivery of Interferon in Rats and Primates".

Santiago et al., *Pharm. Res.* 11: 1994, p. S–298 "Evaluation in Rats of Vehicles for the Oral Delivery of Low Molecular Weight Heparin".

X. Ma et al., PDD 7303 *Pharmaceutical Research* 9(10):S–244, 1992 (Oct. Supplement).

Milstein et al., *Symposia Abstracts.* AAPS Annual Meeting, San Antonia, TX, Nov. 15–19 (1993).

Santiago et al. "Initial Studies In The Assessment of Proteinoid Microsphere Activity" *Proceed. Intern. Symp. Control. Rel. Bioact. Mater.,* 20 (1993), Controlled Release Society, Inc.

Santiago et al., "Oral Immunization of Rats with Influenza Virus M Protein (M1) Microspheres" *Proceed. Intern. Symp. Control. Rel. Bioact. Mater.,* 19 (1992), Controlled Release Society, Inc., p. 116–117.

Santiago et al. "Proteinoid Microspheres For The Oral Delivery of Heparin" *Proceed. Intern. Symp. Control. Rel. Bioact. Mater.,* 19 (1992), Controlled Release Society, Inc. p. 514–515.

Santiago et al. *American Society for Microbiology* 92nd General Meeting, Abstract of the General Meeting, p. 159, May 26–30, 1992.

Milstein et al. "Preparation And In Vitro Characterization Of Proteinoid Microspheres" *Proceed Intern. Symp. Control. Rel. Bioact. Mater.,* 19 (1992), Controlled Release Society, Inc. p. 516–517.

Doris K. Chiappetta, *Eastern Analytical Symposium,* Nov. 17, 1992 "Solutions for Problems in Bioanalysis".

Elizabeth A. Harris, M.S., *Eastern Analytical Symposium,* Nov. 17, 1992 "Solutions for Problems in Bioanalysis".

*AAPS 6TH Ann. Meeting and Exp.,* "Proteinoids—A Novel Drug Delivery System" Nov. 19, 1992, p. 33.

Milstein et al., "Efficient Oral Delivery Of Monoclonal Antibodies By Proteinoid Encapsulation" *The 1993 Miami Bio/Technology Winter Symposium—Advances in Gene Technology: Protein Engineering and Beyond,* Jan. 17–22, 1993.

Xinghang Ma, et al. "Stability Study of Drug–loaded Proteinoid Microsphere Formulations during Freeze–drying" *Journal of Drug Targeting,* 1994, vol. 2, pp. 9–21.

Baughman et al., "Screening Candidate Microsphere Formulations By Incubating In Simulated Digestive Fluids" *Proc. of the 6th Intern'l. Sympo. on Recent Advances in Drug Delivery Systems,* Ctr. for Controlled Chem. Delivery, University of Utah, Feb. 22–25, 1993, pp. 181–182.

Robert O. Dillman, M.D., *Annals of Internal Medicine* 1989:111 pp. 592–600, "Monoclonal Antibodies for Treating Cancer".

Brendan D. Curti, *Critical Reviews in Oncology/Hematology,* 1993: 14 pp. 29–39 "Physical barriers to drug delivery in tumors".

V. Hird et al, *Genes and Cancer,* edited by Desmond Carney & Karol Sikora, pp. 183–189, Immunotherapy with Monoclonal Antibodies.

Michael E. Osband et al., *Immunology Today,* vol. 11, No.6 1990, pp. 193–195, "Problems in the investigational study and clinical use of cancer immunotherapy".

William J. Harris, *Tibtech* Feb. 1993 vol. 11, pp. 42–44 "Therapeutic antibodies—the coming of age".

Thomas A. Waldmann, *Science,* Jun. 21, 1991, 252:1657–1662, "Monoclonal Antibodies in Diagnosis and Therapy".

*Chemical Abstracts,* 76(14):72994u, (1971).

*Chemical Abstracts,* 84(7):44660d, (1975).

*Chemical Abstracts,* 86(16):107529g, (1976).

*Chemical Abstracts,* 112(15):134663h, (1989).

*Chemical Abstracts,* 114(22):214519x, (1990).

J. Györe et al., *Thermal Analysis,* vol. 2—Proceeding Fourth ICTA Budapest 1974, pp. 387–394.

*Chemical Abstracts,* 99(19) 158832b, (1982).

*Derwent Abstracts,* JP 67008622, (1967).

*Journal of Medicinal Chemistry,* vol. 38, No. 21, pp. 4257–4262, (1995), "Microsphere Formation in a Series of Derivatized α–Amino Acids: Properties, Molecular Modeling, and Oral Delivery of Salmon Calcitonin".

Andrea Leone–Bay et al., *Journal of Medicinal Chemistry,* vol. 38, No. 21, pp. 4263–4269, (1995), "N–Acylated α–Amino Acids as Novel Oral Delivery Agents for Proteins".

*The Extra Pharmacopoeia,* Thirtieth Edition, pp. 325–326, (1993).

Stephen J. Douglas et al., *Chemistry and Industry,* vol. 22:748–751, 1985.

C.A. Finch, *Chemistry and Industry,* vol. 22:752–756, 1985.

John A. Butera et al., *J. Med. Chem.,* vol. 34:3212–3228, 1990.

Madeline G. Cimini et al., *Ann. Report in Med Chem.,* vol. 27:89–98., 1992.

Bernadette Earley et al., *Brain Research,* vol. 546:282–286, 1991.

John W. Ellingboe et al., *J. Med Chem.,* vol. 35:705–716, 1992.

William C. Lumma et al., *J. Med Chem.,* vol. 30:758–763, 1987.

Joseph J. Lynch et al., *J. of Pharm. and Exp. Therap.,* vol. 269:541–554, 1994.

Kiyoshi Matsuno et al., *Brain Research,* vol. 575:315–319, 1992.

Thomas K. Morgan et al., *J. Med. Chem.,* vol. 33:1091–1097, 1990.

Hitoshi Oinuma et al., *J. Med. Chem.,* vol. 33:903–905, 1990.

Tadimeti S. Rao et al., *Molecular Pharmacology,* vol. 37:978–982, 1990.

Asaji Kondo, *Microcapsule Processing and Technology,* pp. 154–165, 1979.

G. Pastores et al., *J. Liquid Chromatography,* 18(15):3049–3059, 1995.

D. Sinha et al., *J. Bio. Chem.,* 260(19):10714–10719. 1985.

E. Franssen et al., *J. Med. Chem.,* 35:1246–1259, 1992.

*Chemical Abstracts,* 99(23):191473h, Dec. 5, 1983.

R. Langer, *Science,* 249:1528, Sep. 28, 1990.

M. Alonso et al., *Vaccine,* 12:299, 1994.

A. Leone–Bay et al., *J. Med. Chem.,* 39:2571–2578, 1996.

R. Thompson, *Biochemistry,* 12:47–51, 1973.

S. Thompson, *J. Med. Chem.,* abstract, 86:174780, 1986.

Ito et al., *Proc. Natl. Acad. Sci.,* 76(3):1199–1203, Mar. 1979.

Finkelstein et al., *J. Mol. Biol.,* 103:15–24, May 1976.

Dolgikh et al., *Eur. Biophys. J.,* 13:109–121, 1985.

Dolgikh et al., *FEBS Letters,* 136:311–315, Dec. 1981.

Ptitsyn et al., *Quar. Rev. Biophys.,* 13(3):339–386, Aug. 1980.

Chen et al., *Biochemistry,* 31:1464–1476, Feb. 1992.

Bychkova et al., *Chemtracts—Biochem. and Molec. Biol.,* 4:133–163, 1993.

Christensen et al., *J. Med. Chem.,* 33:1091–1097, Apr. 1990.
Haynie et al., *Proteins: Structure, Function, and Genetics,* 16:115–140, Jun. 1993.
Goto et al., *Biochemistry,* 28:945–952, Feb. 1989.
Sakai et al., *Protein Expression and Purification,* 4:563–569 (1993).
Norgaard–Pederson, Chapter 16, 125–128.
Norgaard–Pederson et al., *Acta med. scand.,* 192:227–230, 1972.
Phillips, *Structural Biology,* 1(1):76–77, Jan. 1994.
Creighton, *Science,* 240:267, 344–343, Apr. 1988.
Wyman, J., Jr., *Linked Functions and Reciprocal Effects,* 224–286.
Liang, H. et al., *Biochemistry,* 30:2772–2782, Mar. 1991.
Carr, C.M. et al., *Science,* 266:234–236, Oct. 14, 1994.
Ramsay, G. et al., *Biochemistry,* 28:529–533, Jan. 1989.
Ptitsyn, O.B., *Protein Engineering,* 7(5):593–596, May 1994.
Ptitsyn, O.B. et al., *FEBS,* 262(1):20–24, Mar. 1990.
Creighton, T.E., *Structural Biology,* 1(3):135–138, Mar. 1994.
Nölting, B. et al., *Biochemistry,* 32:12319–12323, Nov. 1993.
Vonderviszt, F. et al., *Biochemical and Biophysical Research Communications,* 148(1):92–98, Oct. 14, 1987.
Koseki, T. et al., *J. Biochem.,* 103:425–430, Mar. 1988.
Goto, Y. et al., *J. Mol. Biol.,* 214:803–805, Aug. 1990.
Barrick, D. et al., *J. Mol. Biol.,* 237:588–601, Apr. 1994.
Peng, X. et al., *Biochemistry,* 33:8323–8329, Jul. 1994.
Uversky, V.N. et al., *Biochemistry,* 33:2782–2791, Mar. 1994.
Purcell, A.W. et al., *Anal. Chem.,* 65:3038–3047, Nov. 1993.
Palleros, D.R. et al., *Biochemistry,* 32:4314–4321, Apr. 1993.
Finkelstein, A.V. et al., *Prog. Biophys. molec. Biol.,* 50:171–190, 1987.
Redfield, C. et al., *Structural Biology,* 1(1):23–29, Jan. 1994.
Uversky, V.N., *Biochemistry,* 32:13288–13298, Dec. 1993.
Finkelstein, A.V. et al., *Bioplymers,* 28:1681–1694, Oct. 1989.
Hagihara Y. et al., *J. Mol. Biol.,* 231:180–184, May 1993.
Goto, Y., *J. Mol. Biol.,* 218:387–396, Mar. 1991.
Goto, Y., et al., *Biochemistry,* 29:3480–3488, Apr. 1990.
Goto, Y., et al., *Proc. Natl. Acad. Sci. USA,* 87–573–577, Jan. 1990.
Peterson, M. et al., *Nature,* 357:596–598, Jun. 18, 1992.
Momburg, F. et al., *Nature,* 367:648–651, Feb. 17, 1994.
Peterson, M. et al., *Nature,* 345:172–174, May 10, 1990.
Krumbiegel, M. et al., *Biophysical Journal,* 67:2355–2360, Dec. 1994.
Wiedmann, B. et al., *Nature,* 370:434–440, Aug. 11, 1994.
Gray, R.A. et al., *Biochemistry,* 33:1323–1331, Feb. 1994.
Calciano, L.J. et al., *Biochemistry,* 32:5644–5649, Jun. 1993.
Semisotnov, G.V. et al., *J. Mol. Biol.,* 213:561–568, Jun. 1990.
Prestrelski, S.J. et al., *Biochemistry,* 30:8797–8804, Sep. 1991.
Weinstein, M. et al., *Medicina,* XXX(2):147–152, Mar.–Apr. 1970.
Kuwajima, K. et al., *FEBS,* 334(3):265–268, Nov. 1993.
Bromberg, L.E. et al., *Proc. Natl. Acad. Sci. USA,* 91:143–147, Jan. 1994.
Rothman, J.E., *Nature,* 372:55–63, Nov. 3, 1994.
Beyreuther, K. et al., *Nature,* 370:419–420, Aug. 11, 1994.
Kocisko, D.A., *Nature,* 370:471–474, Aug. 1994.
Neupert, W. et al., *Nature,* 370:421–422, Aug. 1994.
Mendel, D. et al., *Science,* 256:1798–1802, Jun. 1992.
Kim, C.A. et al., *Nature,* 362:267–270, Mar. 1993.
Richardson, J.S. et al., *Science,* 240:1648–1652, Jun. 1988.
Blaber, Michael et al., *Science,* 260:1637–1640, Jun. 1993.
Kellis, J.T., Jr. et al., *Nature,* 333:784–786, Jun. 1988.
Gao, J. et al., *Science,* 244:1069–1072, Jun. 1989.
Presta, L.G. et al., *Science,* 240:1632–1641, Jun. 1988.
Hodges, R.S. et al., *Journal of Biological Chemistry,* 263/24:11768–11775, Aug. 1988.
Mondrup, M., *Annals of Academy of Medicine,* 9(1):60–64, Jan. 1980.
Kaiser, J., *Science,* 265:1525, Sep. 1994.
Radmacher, M. et al., *Science,* 265:1577–1579, Sep. 1994.
Kondo, Takahito et al., *Clinica Chimica Acta,* 60:347–353, May 1975.
Semisotnov, G.V. et al., *FEB,* 224(1):9–13, Nov. 1987.
Ptitsyn, O.B. et al., *Journal of Biomolecular Structure & Dynamics,* 4(1):137–156, Aug. 1986.
Brazhnikov, E.V. et al., *Biopolymers,* 24:1899–1907, Oct. 1985.
de Dios, A.C. et al., *Science,* 260:1491–1496:Jun. 4, 1993.
Chen, Bao–lu et al., *Biochemistry,* 28:685–691, Jan. 1989.
Chen, Bao–lu et al., *Biochemistry,* 28:691–699, Jan. 1989.
Naujokas, M.F. et al., *Cell,* 74:257–268, Jul. 1993.
de Haseth, J.A., *New York SAS Announcer,* Abstract & Drawings presented at Nov. meeting.
DeRuiter, J. et al., *Biochemicai Pharmacology,* 40(10):2219–2226, Nov. 1990.
Bode, W. et al., *Proteolysis and Physiological Regulation,* 43–76.
Marshall, G.R. et al., *Quantitative Structure–Activity Relationships in Drug Design,* 287–295, 1989.
Ogawa, T. et al., *Peptide Research,* 3(1):35–41, Jan.–Feb. 1990.
Tsou, C.–L., *Science,* 262:380–381, Oct. 1993.
Hahn, K.W. et al., *Science,* 248:1544–1547, Jan. 1989.
Luger, K. et al., *Science,* 243:206–210, Jan. 1989.
Cygler, M., *Nature,* 363:674–698, Jun. 1993.
Verschueren, K.H.G., *Nature,* 363:693–698, Jun. 1993.
Wong, C.–H., *Articles,* 1145–1152, Jun. 1989.
Bone, R. et al., *Nature,* 339:191–196, May 1989.
Riddihough, G., *Nature,* 362:793, Apr. 1993.
Aqvist J. et al., *Biochemistry,* 28:4680–4689, May 1989.
Quiocho, F.A. et al. *Nature,* 340:404–407, Aug. 1989.
Janin, J. et al., *J. Mol. Biol.,* 100:197–211, Jan. 1976.
Warshel, A. et al., *Proc. Natl. Acad. Sci. USA,* 86:5820–5824, Aug. 1989.
Dorovska–Taran, V.N. et al., *Eur. J. Biochem.,* 211:47–55, Jan. 1993.
Brandt, W. et al., *Journal of Computer–Aided Molecular Design,* 6:159–174, Apr. 1992.
Jadaud, P. et al., *Chirality* 1:38–44, Jan. 1989.
Burke, P.A. et al., *J. Bio. Chem.,* 267/28:20057–20064, Oct. 1992.
Schreuder, H.A. et al., *Structural Biology,* 1:48–54, Jan. 1994.
Mattos, C. et al., *Structural Biology,* 1:55–58, Jan. 1994.
Fujii, S. et al., *J. Biochem,* 95:319–322, Feb. 1984.
Fujii, S., *Adv–Exp Med Biol.,* 70:75–79, 1976.
Nakayama, T. et al., *Chem. Pharm. Bull.,* 41(1):117–125, Jan. 1993.

Okutome, T. et al., *Chem. Pharm. Bull.,* 32(5):1854–1865, May 1984.
Nakayama, T. et al., *Chem. Pharm. Bull.,* 32(10):3968–3980, Oct. 1984.
Yaegashi, T. et al., *Chem. Pharm. Bull.,* 32(11):4466–4477, Nov. 1984.
Niinobe, M. et al., *FEBS Letters,* 172(2):159–162, Jul. 1984.
Ogawa, K. et al., *Chem. Pharm. Bull.,* 34(8):3252–3266, Aug. 1986.
Aoyama, T. et al., *Chem. Pharm. Bull.,* 33(4):1458–1471, Apr. 1985.
Wert, Jr., J.J. et al., *Biochemical and Biophysical Research Communications,* 186(3):1327–1332, Aug. 1992.
Yokoo, N. et al., *Yakugaku Zasshi,* 108(2):164–169, Feb. 1988.
Yokoo, N. et al., *Yakugaku Zasshi,* 107(9):732–737, Sep. 1987.
Yokoyama, T. et al., *Studies on New Synthetic Inhibitors . . .*, 271–276.
Muramatu, M. et al., *J. Biochem.,* 58(3):214–226, Sep. 1965.
Ohkoshi, M. et al., *Gann,* 73:108–110, Feb. 1982.
Hitomi, Y. et al., *Haemostasis,* 15:164–168, Mar. 1985.
Ikehara, S., *Immunology,* 55:595–600, Aug. 1985.
Tamura, Y. et al., *Biochimica et Biophysica Acta,* 484:417–422, Oct. 1977.
Walker, B. et al., *Biochem. J.,* 293:321–323, Jul. 1993.
DeGrado, W.F., *Nature,* 365:488–489, Oct. 1993.
Levashov, A.V. et al., *FEBS* 13434, 336(3):385–388, Dec. 1993.
Schellenberger, V. et al., *Biochemistry,* 32:4349–4353, Apr. 1993.
Lovell, J. et al., *Biochemical Society Transactions,* 21:268S Aug. 1993.
Bagger, S., *Protease and Cobalt (III)—Ligated Peptides,* 165–171, Jan. 1993.
Maeda, L. et al., *Biochemical and Biophysical Research Communications,* 193(1):428–433, May 1993.
Li, M. et al., *Biochemical and Biophysical Research Communications,* 196(2):907–913, Oct. 1993.
Flynn, G.C. et al., *Proc. Natl. Acad. Sci. USA,* 90:10826–10830, Nov. 1993.
Demuth, H.–U. et al., *Pharmazie,* 43:262–264, 1988.
Demuth, H.–U. et al., *Studies in Organic Chemistry,* 31:439–446, 1987.
Sakamoto, H. et al., *J. Mol. Rec.,* 6:95–100, Feb. 1993.
Lee, A.Y. et al., *Chemistry & Biology,* introductory issue:x–xiApr. 1994.
Benedetti, E. et al., *Int. J. Peptide Protein Res.,* 21:163–181, 1983.
Piela, L. et al., *Biopolymers,* 26:1273–1286, 1987.
Demuth, H.–U. et al., *J. Org. Chem.,* 54:5880–5883, 1989.
Kovach, I.M. et al., *Advances in the Biosciences,* 65:205, 212, 1987.
Parker, et al., *Peptide Research,* 4(6):347–354, Nov.–Dec. 1991.
Parker, et al., *Peptide Research,* 4(6):355–363, Nov.–Dec. 1991.
Tanaka, et al., *Biophysical Chemistry,* 50:47–61, May 1994.
Fedorov, et al., *J. Mol. Biol.,* 225:927–931, Jun. 1992.
Freire, et al., *J. Mol. Biol,* 222:687–698, Dec. 1991.
Baker, et al., *Biochemistry,* 33/24:7505–7509, Jun. 1994.
Freire, et al., *Biochemistry,* 31:250–256, Jan. 1992.
Freire, E., *Dept. of Biol. and Biocalorimetry Ctr.,* In Press Manuscript:1–35, Jul. 1994.
Xie, et al., *Dept. of Biol. and Biocalorimetry Ctr.,* In Press Manuscript:1–46, May 1994.
Murphy, et al., *Dept. of Biol. and Biocalorimetry Ctr.,* 43:312–361, 1992.
Gething, et al., *Nature,* 355–33–45, Jan. 1992.
Martin, et al., *Structure,* 1:161–164, Nov. 1993.
Agard, David A. *Science,* 260:1903–1904, Jun. 1993.
Cioni, et al., *Biophysical Chemistry,* 52:25–34, 1994.
Oss, et al., *J. Dispersion Science and Technology,* 12:273–287, 1991.
Hu, et al., *Biochemistry,* 33:562–569, Jan. 1994.
Nishii, et al., *Biochemistry,* 33:4903–4909, Apr. 1994.
Evans, et al., *Proteins: Structure, Function and Genetics,* 9:248–266, 1991.
Bjork, et al., *Fed. of European Bio. Societies,* 299/1:66–68, Mar. 1992.
Fuji, et al., *J. Biochem,* 88/3:789–796, Mar. 1980.
Taniguchi, Ernesto, *Analytical Biochemistry,* 72:144–152, May 1976.
Fuji, et al., *J. Biochem,* 93/1:189–196, Jan. 1983.
Sosnick, T.R., *Structure Biol.,* 1/3:149–156, Mar. 1994.
Ptitsyn, et al., *Biopolymers,* 22:15–25, Jan. 1983.
Ptitsyn, et al., *Protein Engineering,* 2/6:443–447, Mar. 1989.
Stuart, D., *Nature,* 371:19, Sep. 1994.
Balant, et al., *European Journal of Drug Metabol. & Pharm.,* 15/2:143–153, Apr.–Jun. 1990.
Bychkova, et al., *Biochemistry,* 31:7566–7571, Aug. 1992.
Finkelstein, et al., *Biopolymers,* 16:469–495, Mar. 1977.
Finkelstein, et al., *Biopolymers,* 16:497–524, Mar. 1977.
Shortle, et al., *Biochemistry,* 27:4761–4768, Jun. 1988.
Murphy, et al., *Biochemistry,* 30/20:337; 29/37:8679; 30/20:5059, 1990–1991.
Plaza del Pino, et al., *Biochemistry,* 31:11196–11202, Nov. 1992.
Murphy, K.P. et al., *J. Mol. Biol.,* 227:293–306, Sep. 1992.
Fu, et al., *Proc. Natl. Acad. Sci. USA.,* 89:9335–9338, Oct. 1992.
Xie, et al., *Biochemistry,* 30:10673–10678, Nov. 1991.
Dunitz, J.D., *Science,* 264:670, Apr. 1994.
Pethig, R., *Dielectric Studies of Protein Hydration,* 265–288.
Oliveira, et al., *J. Mol. Biol.,* 240:184–187, Jul. 1994.
Bone, S., *Phys. Med. Biol.,* 39:1801–1809, 1994.
Search Results: Timasheff, S.N., *Methods in Mol. Biol.,* 40:253–69, 1995; Ward et al., *Biochemistry,* 33:11900–1908, Oct. 94; Ward et al., *Biochemistry,* 33:11891–11899, Oct. 94; Perez–Ramirez et al., *Biochemistry,* 33:6262–6267, May 1994; Perez–Ramirez et al., *Biochemistry,* 33:6253–6261, May 1994; Timasheff, S.N., Ann. Rev. Biophys. Biomol. Struct., 22:67–97, 1993; Bhat et al., *Protein Science,* 1:1133–1143, Sep. 1992; Timasheff, S.N., *Biochemistry,* 31:9857–9864, Oct. 1992.
Kemeny, *Process Analysis,* 69–71.
Mitchell, P., *Res. Microb.,* 286–289, Mar.–Apr. 1990.
Matouschek, et al., *Nature,* 340:122–126, Jul. 1989.
Bychkova et al., *Mol. Biol.,* 14:278–286, 1980.
Xie, et al., *Dept. of Biol. and Biocalorimetry Ctr.,* In Press Manuscript:1–25, Apr. 1994.
Buchner, et al., *Biochemistry,* 30:6922–6929, Jul. 1991.
Matthews, R.C., *Annu. Rev. Biochem.,* 62:653–683, 1993.
Finkelstein, et al., *Proteins: Structure, Function and Genetics,* 10:287–299, 1991.
Zhong, et al., *Proc. Natl. Acad. Sci. USA,* 89:4462–4465, May 1992.

Kajihara, et al., *J. Biochem*, 104:638–642, Oct. 1988.
Bullough, et al., *Nature*, 371:37–42, Sep. 1994.
Schon, et al., *Biochemistry*, 28:5019–5024, Jun. 1989.
Ramsay, et al., *Biochemistry*, 29:8677–8683, Sep. 1990.
Ptitsyn, O.B., *FEBS Letter*, 285/2:176–181, Jul. 1991.
Pfeil, et al., *FEBS Letter*, 198/2:287–291, Mar. 1986.
Ptitsyn, et al., *FEBS Letter*, 317/3:181–184, Feb. 1993.
Uversky, et al., *FEBS Letter*, 314/1:89–92, Dec. 1992.
Vas, et al., *Eur. J. Biochem.*, 189, 575–579, May 1990.
Sinev, et al., *Eur. J. Biochem.*, 180, 61–66, Mar. 1989.
Bowers, C.Y., *Journal of Ped. Endocrin.*, 6/1:21–31, Jan.–Mar. 1993.
Gardner, M.L.G., *Biol. Rev.*, 59:289–331, Feb. 1984.
Gardner, M.L.G., *Ann. Rev. Nutr.*, 8:329–350, 1988.
Ishida, et al., *J. Am. Chem. Soc.*, 107:3305–3314, 1985.
Dill, et al., *Nature Structural Biol.*, 4/1:10–19, Jan. 1997.
Murphy, K.P. et al., *Proteins: Structure, Function, and Genetics*, 15:113–120, Feb.
Freire E. et al., *Annu. Rev. Biophys. Biophys. Chem.*, 19:159–189, 1990.
Breslauer, K.J. et al., *Methods in Enzymology*, 211:533–567, 1992.
Ptitsyn et al., *FEBS Lett.*, 341:15–18, Mar. 1994.
Shrake, A. et al., *Biopolymers*, 32:925–940, Aug. 1992.
Saroff, H.A., *Biopolymers*, 31:1037–1047, Aug. 1991.
Royer, C.A., *Analytical Biochemistry*, 210:91–97, Apr. 1993.
Miranker, A., *Science*, 262:896–900, Nov. 1993.
Kuehn, M.J. et al., *Science*, 262:1234–1241, Nov. 1993.
Travis J., *Science*, 262:1374, Nov. 1993.
Harbury, P.B. et al., *Science*, 262:1401–1407, Nov. 1993.
Baldwin, E.P. et al., *Science*, 262:1715–1718, Dec. 1993.
Jennings, P.A. et al., *Science*, 262:892–896, Nov. 1993.
Kamtekar, S. et al., *Science*, 262:1680–1685, Dec. 1993.
Lovejoy, B. et al., *Science*, 259:1288–1293, Feb. 1993.
Bhakuni, V. et al., *Biochemistry*, 30:5055–5060, May 1991.
Ohgushi, M. et al., *FEBS 0981*, 164:21–24, Nov. 1983.
Strickland, D.K. et al., *Biochemistry*, 30:2797–2803, Mar. 1991.
Straume, M. et al., *Analytical Biochemistry*, 203:259–268, Jun. 1992.
Hua, Q.X. et al., *Biochemistry*, 32:1433–1442, Feb. 1993.
Ui, N., *Biochimica et Biophysica Acta*, 229:567–581, Mar. 1971.
Thompson, K.S. et al., *Biochemistry*, 32(21):5491–5496, Jun. 1993.
Chervenak, M.C. et al., *J. Am. Chem. Soc.*, 116:10533–10539, 1994.
Beschiaschvili, G. et al., *Biochemistry*, 31:10044–10053, Oct. 1992.
Sigurskjold, B.W. et al., *Eur. J. Biochem.*, 197:239–246, 1991.
Williams, B.A. et al., *J. Bio. Chem.*, 267(32):22907–22911, Nov. 1992.
Holzman, T.F. et al., *J. Pro. Chem.*, 10(5):553–563, Oct. 1991.
Connelly, P.R. et al., *Proc. Natl. Acad. Sci. USA*, 89:4781–4785, Jun. 1992.
Freire, E. et al., *Analytical Chemistry*, 62(18):950A–959A, Sep. 1990.
Wiseman, T. et al., *Analytical Biochemistry*, 179:131–137, May 1989.
Brandts, J.F. et al., *Article: An Instrument for Rapid Determination . . .* , 30–35, May 1990.

Weber, P.C. et al., *Biochemistry*, 31:9350–9354, Oct. 1992.
Varadarajan, R. et al., *Biochemistry*, 31:1421–1426, Feb. 1992.
Connelly, P.R., *Biochemistry*, 29:6108–6114, Jun. 1990.
Lin, L.–N. et al., *Biochemistry*, 30(50):11660–11668, Dec. 1991.
Bains, G. et al., *Analytical Biochemistry*, 192:203–206, Jan. 1991.
Ogasahara, K. et al., *J. Bio. Chem.*, 267(8):5222–5228, Mar. 1992.
Marky, L.A., *Biochemistry*, 29:4805–4811, May 1990.
Thermodynamics, Snowbird, VT, Aug. 1992: *Effects of Mutations on the Thermodynamics of Processing Proteins.*
Ledeen, R.W. et al., *New Trends in Ganglioside Research*, 14:93–104, 1988.
Williams, B.A. et al., *J. Org. Chem*, 58:3507–3510, 1993.
Morin, P.E. et al., *Biochemistry*, 30:8494–8500, Aug. 1991.
Myers, M. et al., *Biochemistry*, 26(14):4309–4315, Jul. 1987.
Zhang, F. et al., *Biochemistry*, 31(7):2005–2011, Feb. 1992.
Blume, A. et al., *Biochemistry*, 31(19):4636–4642, May 1992.
Ptitsyn, O.B., *FEBS Letters*, 93(1):1–4, Sep. 1978.
Ptitsyn, O.B., *FEBS Letters*, 101(1):1–5, May 1979.
Pain, R.H., *Nature*, 358:278–307, Jul. 1992.
Dobson, C.M., *Current Biology*, 4(7):636–640, Jul. 1994.
Mayo, S.L. et al., *Science*, 262:873–876, Nov. 1993.
Ohgushi, M. et al., *Adv. Biophys.*, 18:75–90, 1984.
van Osdol, W.W. et al., *Biopys. J.*, 59:48–54, Jan. 1991.
Koenigbauer, M.J., *Pharmaceutical Research*, 11(6);777–783, Jun. 1994.
Blandamer, M.J. et al., *J. Chem. Soc. Faraday Trans.*, 86(9):1437–1441, 1990.
Kubal, et al., *Eur. J. Biochem*, 781–787, Mar. 1994.
Slavik, J., *Biochimica et Biophysica Acta*, 694:1–24, Aug. 1982.
Miranker, et al., *Nature*, 349:633–636, Feb. 1991.
Feng, et al., *Biochemistry*, 30:7711–7717, Aug. 1991.
Hagihara, et al., *J. Mol. Biol.*, 237:336–348, Apr. 1994.
Foguel, et al., *Proc. Natl. Acad. Sci. USA*, 91:8244–8247, Aug. 1994.
Goto, et al., *Biochemistry*, 32:11878–11885, Nov. 1993.
Narhi, et al., *Biochemistry*, 32:5214–5221, May 1993.
Zemel, et al., *Kidney International*, 46:1422–1430, Nov. 1994.
Safar, et al., *Biochemistry*, 33:8375–8383, Jul. 1994.
Pietrzkowski, et al., *Cancer Research*, 52:6447–6451, Dec. 1992.
Nakano, et al., *The Journal of Biological Chemistry*, 265/21:123561–12362, Jul. 1990.
Carra, et al., *Protein Science*, 3:952–959, Jun. 1994.
Hlodan, et al., *FEBS Letter*, 343:256–260, May 1994.
Philo, et al., *Biochemistry*, 32:10812–10818, Oct. 1993.
Dryden, et al., *Biochimica et Biophysica Acta*, 1078:94–100, May 1991.
Kumar, et al., *The Journal of Biological Chemistry*, 269/17:12620–12625, Apr. 1994.
Nozaki, et al., *Journal of the American Chemical Society*, 89/4:736–742, Feb. 1967.
Nozaki, et al., *Journal of the American Chemical Society*, 89/4:742–749, Feb. 1967.
Liepinsh, et al., J. Am. Chem. Soc., 116:9670–9674, Dec. 1994.

Weiner, et al., *Biochemical and Biop. Res. Communications*, 198/3:915–922, Feb. 1994.
Matthews, B.W., *Annu. Rev. Biochem.*, 62:139–160, 1993.
Kemp, et al., *Nature*, 352:451–454; 352:379, Aug. 1991.
Lesk, A.M., *Nature*, 352:379, Aug. 1991.
Serrano, et al., *Nature*, 342:296–299, Nov. 1989.
Sandberg, et al., *Science*, 245:54–57, Jul. 1989.
Wuthrich, K., *Science*, 243:45–50, Jan. 1989.
Pain, R.H., *Science*, 344:198–200; 344:268–270, Mar. 1990.
Handel, T.M., *Science*, 261:879–885, Aug. 1993.
Xie, et al., *Protein Science*, 3:2175–2184, Dec. 1994.
Connelly, et al., *Biochemistry*, 32:5583–5590, Jun. 1993.
Qui, et al., *The Journal of Cell Biology*, 125:595–605, May 1994.
Thomas, D.J., *J. Mol. Biol.*, 216:459–465, Nov. 1990.
Mach, et al., *Biochemistry*, 32/30:7703–7711, Aug. 1993.
Artigues, et al., *The Journal of Biological Chemistry*, 269/35:21990–21999, Sep. 1994.
Jin, et al., *Proc. Natl. Acad. Sci. USA.*, 91:113–117, Jan. 1994.
Charman, et al., *Pharmaceutical Research*, 10/7: 954–962, Jul. 1993.
Wallis, M., *Journal of Molecular Endocrinology*, 11:351–359, Dec. 1993.
Cunningham, et al., *J. Mol. Biol.*, 234:554–563, Dec. 1993.
Sinha, et al., *Journal of Clinical Endocrinology and Metabolism*, 78/6:1411–1418, Jun. 1994.
Shi, et al., *Biochemistry*, 33:7536–7546, Jun. 1994.
Daggett, et al., *Structural Biology*, 4:291–295, 1994.
Mumenthaler, et al., *Pharmaceutical Research*, 11/1:12–20, 1994.
Bismuto, et al., *J. Mol. Biol.*, 241:103–109, 1994.
Arcelloni, et al., *Analytical Biochemistry*, 212:160–167, Jul. 1993.
Bychkova, V.E. et al., Manuscript:1–17.
Hoogstraate, A.J., *Pharm. Res.*, 11(1):83–89, Jan. 1994.
Frezzatti, Jr., W.A. et al., *Biochimica et Biophysica Acta*, 860:531–538, Sep. 1986.
Schreier, S. et al., *Biochimica t Biophysica Acta*, 769:231–237, Jan. 1984.
Bychkova, V.E. et al., *FEB 06336*, 238(2):231–234, Oct. 1988.
Kahns, A.H. et al., *Pharmaceutical Research*, 8(12):1533–1538 (and 1 Fig.), Dec. 1991.
Lakey, J.H. et al., *Eur. J. Biochem.*, 220:155–163, Feb. 1994.
Ulbrandt, N.D. et al., *J. Bio. Chem.*, 267(21):15184–15192, Jul. 1992.
Laine, R.O. et al., *Nature*, 341:63–65, Sep. 1989.
Infante, M.R. et al., *Int. J. Peptide Protein Res.*, 43:173–179, Feb. 1994.
Haltia, T. et al., *BBA Bochimica et Biophysica Acta*, 1228:1–27, Feb. 1995.
Tamm, L.K., *Biochimica et Biophysica Acta*, 1071:123–148, Jul. 1991.
Bramhall, J., *Biochemistry*, 26:2848–2855, May 1987.
Dunker, A.K. et al., *FEBS 10366*, 292(1,2):275–278, Nov. 1991.
Sanders, J.C. et al., *Biochemistry*, 32:12446–12454, Nov. 1993.
Manning, M. et al., *Biochemical and Biphysical Research Communications*, 112(2):349–55, Apr. 1983.
Griffith, J. et al., *Cell*, 23:747–753, Mar. 1981.
Roberts, L.M. et al., *Biochemistry*, 32:10479–10488, Oct. 1993.
Brasseur, R. et al., *Biochimica et Biophysica Acta*, 1029:267–273, Nov. 1990.
Manning, M. et al., *Archives of Biochemistry and Biophysics*, 236(1):297–303, Jan. 1985.
Rohrer, J. et al., *Science*, 250:1418–1421, Dec. 1990.
Kuhn, A., *Science*, 238:1413–1415, Dec. 1987.
Schiksnis, R.A. et al., *J. Mol. Biol.*, 200:741–743, Apr. 1988.
DaPoian, A.T. et al., *Biochemistry*, 33:8339–8346, Jul. 1994.
Derossi, D. et al., *J. Bio. Chem.*, 269(14):10444–10450, Apr. 1994.
Engelman, D.M. et al., *Cell*, 23:411–422, Feb. 1981.
DeGrado, W.F. et al., *Science*, 243:622–628, 1988.
Regan, L. et al., *Science*, 241:976–978, 1988.
Lehn, J., *Makromol. Chem., Macromol. Symp.*, 69:1–17, 1993.
Scrimin, P., *Chimicaoggi*, pp. 63–67, 1989.
Lehn, J., *Angew. Chem. Int. Ed. Engl.*, 27:90–112, 1988.
Chemical Abstracts, Registry No. 73548–12–6 (Apr. 1991).
Chemical Abstracts, Registry No. 70204–54–5 (Apr. 1991).
G. Picciola, *II Farmaco*, 31:655–664 (1976).
Andini, S. et al., (1975) *Orgins of Life*, vol. 6, pp. 147–153.

1 2 3 4 5 6

1 2 3 4 5 6

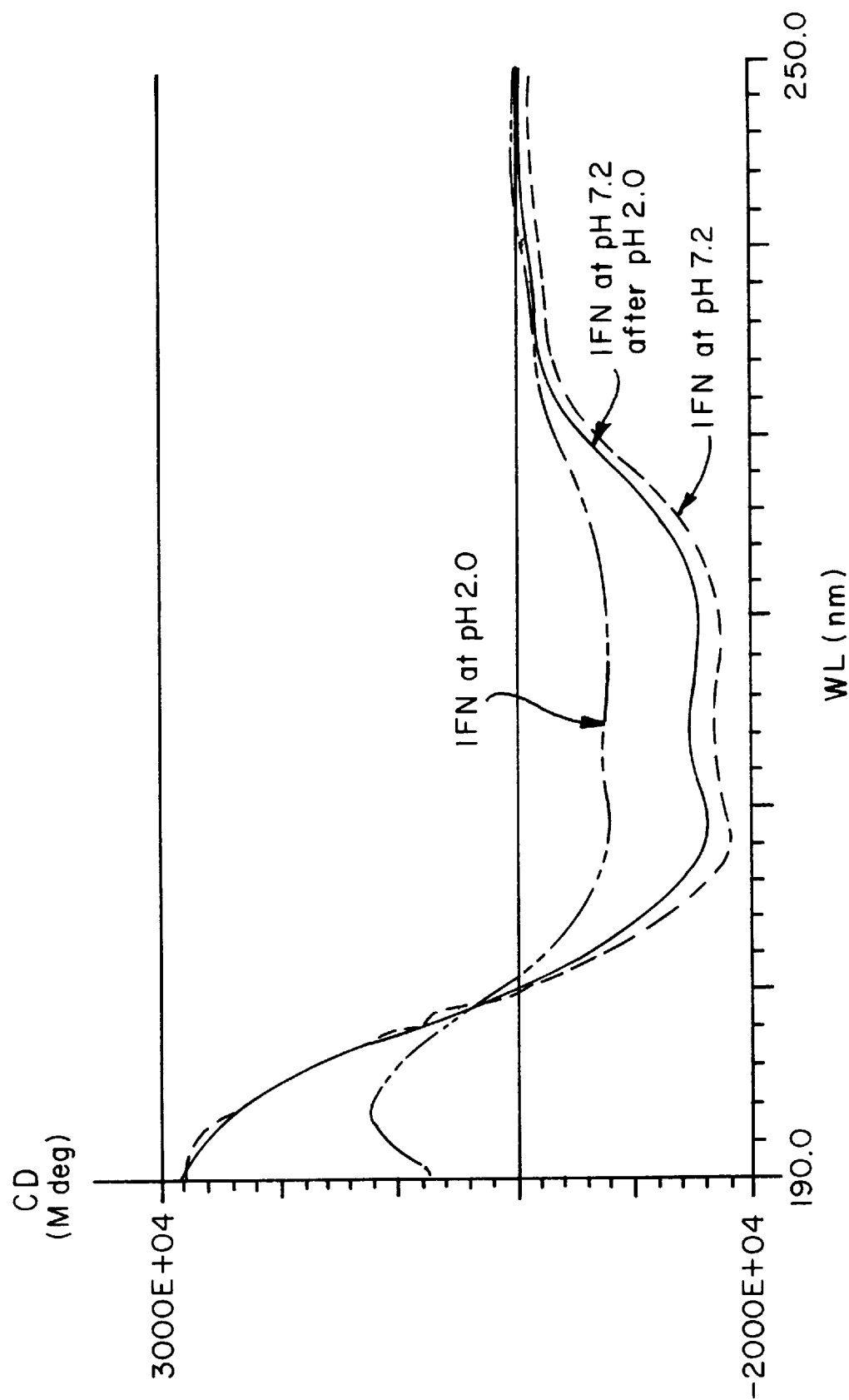

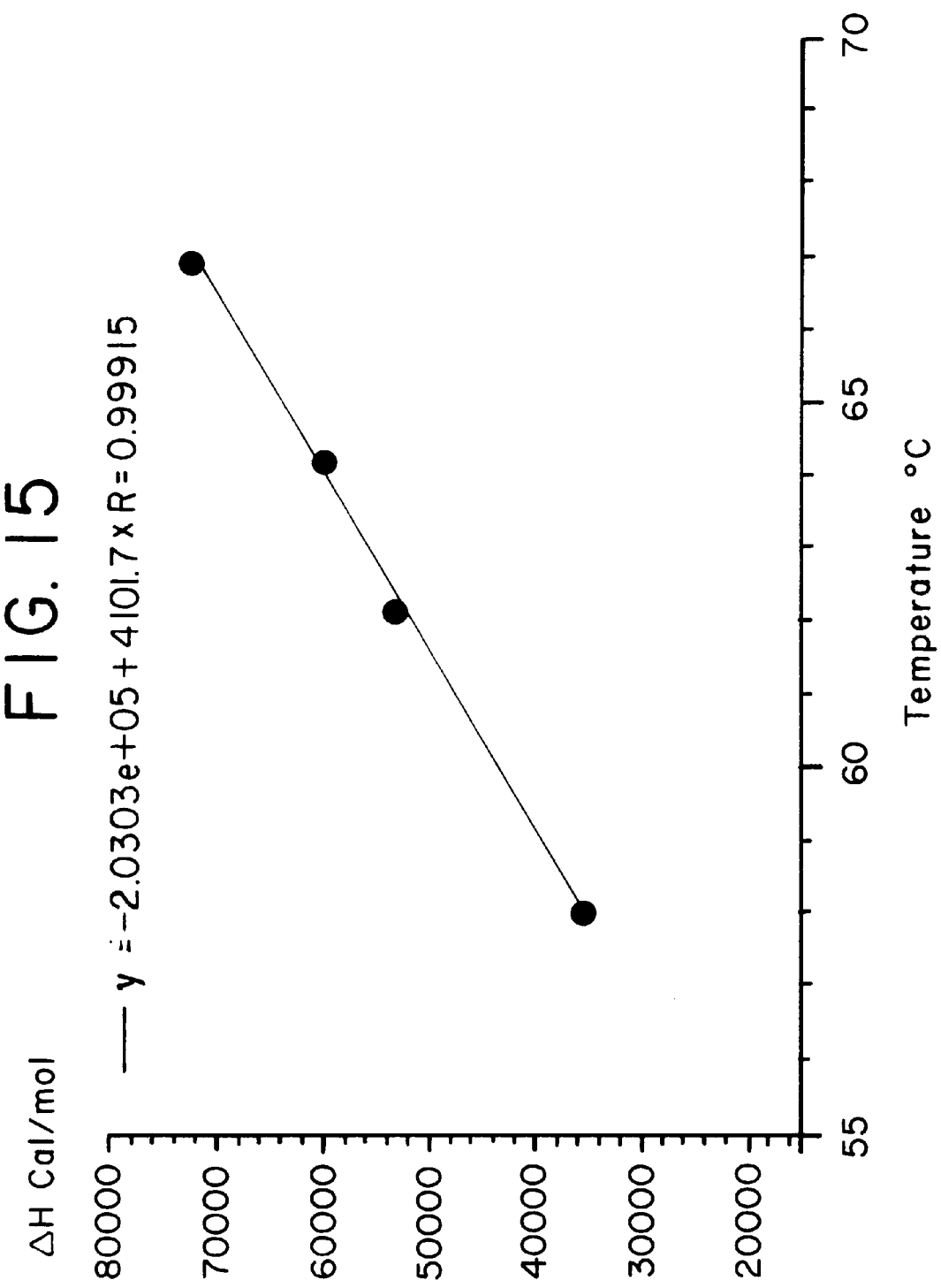

ORALLY DELIVERABLE SUPRAMOLECULAR COMPLEX

This is a continuation of application Ser. No. 08/328,932, filed Oct. 25, 1994, now U.S. Pat. No. 5,714,617;

which is a continuation-in-part of Ser. No. 08/051,019, filed Apr. 22, 1993, now U.S. Pat. No. 5,451,410;

and a continuation-in-part of Ser. No. 08/168,776, filed Dec. 16, 1993, now U.S. Pat. No. 5,447,728;

which is a continuation-in-part of Ser. No. 08/051,019, filed Apr. 22, 1993, now U.S. Pat. No. 5,451,410;

and a continuation-in-part of Ser. No. 08/143,571, filed Oct. 6, 1993, now abandoned;

which is a continuation-in-part of Ser. No. 08/076,803, filed Jun. 14, 1993, now U.S. Pat. No. 5,578,323;

which is a continuation-in-part of Ser. No. 07/920,346, filed Jul. 27, 1992, now U.S. Pat. No. 5,443,841;

which is a continuation-in-part of Ser. No. 07/898,909, filed Jun. 15, 1992, now abandoned;

and a continuation-in-part of PCT/US94/04560, filed Apr. 22, 1994;

which is a continuation-in-part of Ser. No. 08/051,019, filed Apr. 22, 1993, now U.S. Pat. No. 5,451,410;

and a continuation-in-part of Ser. No. 08/205,511, filed Mar. 2, 1994, now U.S. Pat. No. 5,792,451;

and a continuation-in-part of Ser. No. 08/231,622, filed Apr. 22, 1994, now U.S. Pat. No. 5,629,020;

and a continuation-in-part of Ser. No. 08/205,511, filed Mar. 2, 1994, now U.S. Pat. No. 5,792,451;

and a continuation-in-part of Ser. No. 08/231,623, filed Apr. 22, 1994, now U.S. Pat. No. 5,541,155;

and a continuation-in-part of Ser. No. 08/315,200, filed Sep. 29, 1994, now U.S. Pat. No. 5,693,338;

and a continuation-in-part of Ser. No. 08/316,404, filed Sep. 30, 1994 now pending.

FIELD OF THE INVENTION

The present invention relates to methods and compositions for transporting active agents, and particularly biologically active agents, across cell membranes or or lipid bilayers. These methods and compositions facilitate the delivery of an active agent to a target, such as the delivery of a pharmaceutical agent through an adverse environment to a particular location of the body.

BACKGROUND OF THE INVENTION

Conventional means for delivering active agents to their intended targets, e.g. human organs, tumor cites, etc., are often severely limited by the presence of biological, chemical, and physical barriers. Typically, these barriers are imposed by the environment through which delivery must take place, the environment of the target for delivery, or the target itself.

Biologically active agents are particularly vulnerable to such barriers. Oral delivery to the circulatory system for many biologically active agents would be the route of choice for administration to animals if not for physical barriers such as the skin, lipid bi-layers, and various organ membranes that are relatively impermeable to certain biologically active agents, but which must be traversed before an agent delivered via the oral route can reach the circulatory system. Additionally, oral delivery is impeded by chemical barriers such as the varying pH in the gastrointestinal (GI) tract and the presence in the oral cavity and the GI tract of powerful digestive enzymes.

Calcitonin and insulin exemplify the problems confronted in the art in designing an effective oral drug delivery system. The medicinal properties of calcitonin and insulin can be readily altered using any number of techniques, but their physicochemical properties and susceptibility to enzymatic digestion have precluded the design of a commercially viable delivery system. Others among the numerous agents which are not typically amenable to oral administration are biologically active proteins such as the cytokines (e.g. interferons, IL-2, etc); erythropoietin; polysaccharides, and in particular mucopolysaccharides including, but not limited to, heparin; heparinoids; antibiotics; and other organic substances. These agents are also rapidly rendered ineffective or are destroyed in the GI tract by acid hydrolysis, enzymes, or the like.

Biotechnology has allowed the creation of numerous other compounds, of which many are in clinical use around the world. Yet, the current mode of administration of these compounds remains almost exclusively via injection. While in many cases oral administration of these compounds would be preferable, these agents are labile to various enzymes and variations in pH in the GI tract and are generally unable to penetrate adequately the lipid bilayers of which cell membranes are typically composed. Consequently, the active agent cannot be delivered orally to the target at which the active agent renders its intended biological effect.

Typically, the initial focus of drug design is on the physiochemical properties of pharmaceutical compounds and particularly their therapeutic function. The secondary design focus is on the need to deliver the active agent to its biological target(s). This is particularly true for drugs and other biologically active agents that are designed for oral administration to humans and other animals. However, thousands of therapeutic compounds are discarded because no delivery systems are available to ensure that therapeutic titers of the compounds will reach the appropriate anatomical location or compartment(s) after administration and particularly oral administration. Furthermore, many existing therapeutic agents are underutilized for their approved indications because of constraints on their mode(s) of administration. Additionally, many therapeutic agents could be effective for additional clinical indications beyond those for which they are already employed if there existed a practical methodology to deliver them in appropriate quantities to the appropriate biological targets.

Although nature has achieved successful inter- and intracellular transport of active agents such as proteins, this success has not been translated to drug design. In nature, the transportable conformation of an active agent such as a protein is different than the conformation of the protein in its native state. In addition, natural transport systems often effect a return to the native state of the protein subsequent to transport. When proteins are synthesized by ribosomes, they are shuttled to the appropriate cellular organelle by a variety of mechanisms e.g. signal peptides and/or chaperoning. Gething, M- J., Sambrook, J., *Nature*, 355, 1992, 33–45. One of the many functions of either the signal peptides or the chaperonins is to prevent premature folding of the protein into the native state. The native state is usually described as the 3-dimensional state with the lowest free energy. By maintaining the protein in a partially unfolded state, the signal peptides or the chaperonins facilitate the protein's ability to cross various cellular membranes until the protein reaches the appropriate organelle. The chaperonin then separates from the protein or the signal peptide is cleaved from the protein, allowing the protein to fold to the native state. It is well known that the ability of the protein to transit cellular membranes is at least partly a consequence of being in a partially unfolded state.

Current concepts of protein folding suggest that there are a number of discrete conformations in the transition from the native state to the fully denatured state. Baker, D., Agard, D. A., *Biochemistry*, 33, 1994, 7505–7509. The framework model of protein folding suggests that in the initial early stages of folding the domains of the protein that are the secondary structure units will form followed by the final folding into the native state. Kim, P. S., Baldwin, R. L., *Annu. Rev. Biochem.*, 59, 1990, 631–660. In addition to these kinetic intermediates, equilibrium intermediates appear to be significant for a number of cellular functions. Bychkova, V. E., Berni, R., et al, *Biochemistry*, 31, 1992, 7566–7571, and Sinev, M. A., Razgulyaev, O. I., et al, *Eur. J. Biochem.*, 1989, 180, 61–66. Available data on chaperonins indicate that they function, in part, by keeping proteins in a conformation that is not the native state. In addition, it has been demonstrated that proteins in partially unfolded states are able to pass through membranes, whereas the native state, especially of large globular proteins, penetrates membranes poorly, if at all. Haynie, D. T., Freire, E., Proteins:Structure, *Function and Genetics*, 16, 1993, 115–140.

Similarly, some ligands such as insulin which are unable to undergo conformational changes associated with the equilibrium intermediates described above, lose their functionality. Hua, Q. X., Ladbury, J. E., Weiss, M. A., *Biochemistry*, 1993, 32, 1433–1442; Remington, S., Wiegand, G., Huber, R., 1982, 158, 111–152; Hua, Q. X., Shoelson, S. E., Kochoyan, M. Weiss, M. A., *Nature*, 1991, 354, 238–241.

Studies with diphtheria toxin and cholera toxin indicate that after diphtheria toxin binds to its cellular receptor, it is endocytosed, and while in this endocytic vesicle, it is exposed to an acidic pH environment. The acidic pH induces a structural change in the toxin molecule which provides the driving force for membrane insertion and translocation to the cytosol. See, Ramsay, G., Freire, E. *Biochemistry*, 1 990, 29, 8677–8683 and Schon, A., Freire, E., *Biochemistry*, 1 989, 28, 5019–5024. Similarly, cholera toxin undergoes a conformational change subsequent to endocytosis which allows the molecule to penetrate the nuclear membrane. See also, Morin, P. E., Diggs, D., Freire, E., *Biochemistry*, 1990, 29, 781–788.

Earlier designed delivery systems have used either an indirect or a direct approach to delivery. The indirect approach seeks to protect the drug from a hostile environment. Examples are enteric coatings, liposomes, microspheres, microcapsules. See, colloidal drug delivery systems, 1994, ed. Jorg Freuter, Marcel Dekker, Inc.; U.S. Pat. No. 4,239,754; Patel et al. (1976), *FEBS Letters*, Vol. 62, pg. 60; and Hashimoto et al. (1979), *Endocrinology Japan*, Vol. 26, pg. 337. All of these approaches are indirect in that their design rationale is not directed to the drug, but rather is directed to protecting against the environment through which the drug must pass enroute to the target at which it will exert its biological activity, i.e. to prevent the hostile environment from contacting and destroying the drug.

The direct approach is based upon forming covalent linkages with the drug and a modifier, such as the creation of a prodrug. Balant, L. P., Doelker, E., Buri, P., *Eur. J. Drug Metab. And Pharmacokinetics*, 1990, 15(2), 143–153. The linkage is usually designed to be broken under defined circumstances, e.g. pH changes or exposure to specific enzymes. The covalent linkage of the drug to a modifier essentially creates a new molecule with new properties such as an altered log P value and/or as well as a new spatial configuration. The new molecule has different solubility properties and is less susceptible to enzymatic digestion. An example of this type of method is the covalent linkage of polyethylene glycol to proteins. Abuchowski, A., Van Es, T., Palczuk, N. C., Davis, F. F., *J. Biol. Chem.* 1977, 252, 3578.

Broad spectrum use of prior delivery systems has been precluded, however, because: (1) the systems require toxic amounts of adjuvants or inhibitors; (2) suitable low molecular weight cargos, i.e. active agents, are not available; (3) the systems exhibit poor stability and inadequate shelf life; (4) the systems are difficult to manufacture; (5) the systems fail to protect the active agent (cargo); (6) the systems adversely alter the active agent; or (7) the systems fail to allow or promote absorption of the active agent.

There is still a need in the art for simple, inexpensive delivery systems which are easily prepared and which can deliver a broad range of active agents to their intended targets, especially in the case of pharmaceutical agents that are to be administered via the oral route.

SUMMARY OF THE INVENTION

The present invention discloses methods for transporting a biologically active agent across a cellular membrane or a lipid bilayer. A first method includes the steps of:

(a) providing a biologically active agent which can exist in a native conformational state, a denatured conformational state, and an intermediate conformational state which is reversible to the native state and which is conformationally between the native and denatured states;

(b) exposing the biologically active agent to a complexing perturbant to reversibly transform the biologically active agent to the intermediate state and to form a transportable supramolecular complex; and (c) exposing the membrane or bilayer to the supramolecular complex, to transport the biologically active agent across the membrane or bilayer.

The perturbant has a molecular weight between about 150 and about 600 daltons, and contains at least one hydrophilic moiety and at least one hydrophobic moiety. The supramolecular complex comprises the perturbant non-covalently bound or complexed with the biologically active agent. In the present invention, the biologically active agent does not form a microsphere after interacting with the perturbant.

Also contemplated is a method for preparing an orally administrable biologically active agent comprising steps (a) and (b) above.

In an alternate embodiment, an oral delivery composition is provided. The composition comprises a supramolecular complex including:

(a) a biologically active agent in an intermediate conformational state which is reversible to the native state, non-covalently complexed with (b) a complexing perturbant having a molecular weight ranging from about 150 to about 600 and having at least one hydrophilic moiety and at least one hydrophobic moiety;

wherein the intermediate state is conformationally between the native conformation state and denatured conformation state of the biologically active agent and the composition is not a microsphere.

Further contemplated is a method for preparing a mimetic which is transportable across cellular membrane(s) or lipid-bilayer(s) and which is bioavailable to the host after crossing the membrane(s) or bilayer(s). A biologically active agent which can exist in a native conformational state, a denatured conformational state, and an intermediate conformational state which is reversible to the native state and which is conformationally between the native state and the denatured state, is exposed to a complexing perturbant to reversibly transform the biologically active agent to the intermediate conformational state and to form a transportable supramolecular complex. The perturbant has a molecular weight between about 150 and about 600 daltons and at least one hydrophilic moiety and one hydrophilic moiety. The supramolecular complex comprises the perturbant non-covalently complexed with the biologically active agent, and the biologically active agent does not form a microsphere with the perturbant. A mimetic of the supramolecular complex is prepared.

Alternatively, a method for preparing an agent which is transportable across a cellular membrane or a lipid-bilayer, and which is bioavailable after crossing the membrane or bilayer, is provided. A biologically active agent which can exist in a native conformational state, a denatured conformational state, and an intermediate conformational state which is reversible to the native state and which is conformationally between the native and denatured states, is exposed to a perturbant to reversibly transform the biologically active agent to the intermediate state. The agent, a mimetic of the intermediate state, is prepared.

BRIEF DESCRIPTION OF THE DRAWINGS

FIG. 1 is illustration of a native gradient gel of α-interferon (IFN) and a modified amino acid complexing perturbant.

FIG. 2 is an illustration of a native gradient gel of α-interferon and a thermal condensate complexing perturbant.

FIG. 3 is a graphic illustration of serum levels of α-interferon after oral administration of α-interferon with and without complexing perturbants.

FIG. 4 is a graphic illustration of changes in serum calcium in rats orally administered salmon calcitonin with and without complexing perturbants.

FIG. 5 is a graphic illustration of guanidine hydrochloride (GuHCl) induced denaturation of α-interferon.

FIG. 6 is a graphic illustration of the concentration effect of GuHCl on α-interferon conformation.

FIG. 7 is a graphic illustration of the pH denaturation of α-interferon.

FIG. 8 is a graphic illustration of the pH denaturation of insulin.

FIGS. 9A and 9B are graphic illustrations of the reversibility of the circular dichroism spectrum of α-interferon.

FIG. 10 is a graphic illustration of the circular dichroism spectrum of α-interferon.

FIG. 11 is a graphic illustration of intrinsic tryptophan fluorescence of α-interferon and a complexing perturbant.

FIG. 12 is a graphic illustration of serum levels of α-interferon after oral administration of α-interferon with and without complexing perturbant.

FIG. 13 is a graphic illustration of the differential scanning calorimetry of α-interferon and complexing perturbant.

FIGS. 14A and 14B are graphic illustrations of the reversibility of the transformation due to complexing perturbants.

FIG. 15 is a graphic illustration of the effect of complexing perturbant on α-interferon.

FIG. 16 is a graphic illustration of serum levels of α-interferon after oral administration of α-interferon with and without complexing perturbant.

FIG. 17 is a graphic illustration of the concentration effect of complexing perturbant on α-interferon conformation.

FIG. 18 is a graphic illustration of serum levels of α-interferon after oral administration with and without complexing perturbant.

FIG. 19 is a graphic illustration of the effect of complexing perturbant on α-interferon.

FIG. 20 is a graphic illustration of the Isothermal Titration Calorimetry of α-interferon and complexing perturbant.

FIG. 21 is a graphic illustration of the Isothermal Titration Calorimetry of α-interferon and complexing perturbant.

FIG. 22 is a graphic illustration of the effects of complexing perturbants on α-interferon.

FIG. 23 is a graphic illustration of the effect of the concentration of complexing perturbants on α-interferon.

FIG. 24 is a graphic illustration of the Isothermal Titration Calorimetry of α-interferon and complexing perturbant.

FIG. 25 is a graphic illustration of serum levels of α-interferon after oral administration with complexing perturbants.

FIG. 26 is a graphic illustration of the in vivo pharmacokinetics of recombinant human growth hormone mixed with complexing perturbants.

FIG. 27 is a graphic illustration of pancreative inhibition assay with α-interferon and complexing perturbants.

FIG. 28 is a graphic illustration of the effect of DSC of heparin at pH 5.0.

FIG. 29 is a graphic illustration of the degree of retardation vs. peak APTT values from in vivo dosing experiments with heparin.

FIG. 30 is a graphic illustration of clotting time in rats after oral administration of heparin with and without complexing perturbants.

DETAILED DESCRIPTION OF THE INVENTION

All biological organisms can be described as being comprised of aqueous compartments separated from one another by cell membranes or lipid bilayers. Active agents, and particularly pharmacologic or therapeutic active agents, have one solubility value in an aqueous environment and an entirely different solubility value in a hydrophobic environment. Typically, delivery of an active agent from the site of administration to the target site, such as a site of pathology, requires passing the active agent through cell membranes or lipid bilayers in which the solubility of the active agent will vary. Additionally, oral delivery of active agent requires the ability to resist enzymatic degradation, pH differentials, and the like. These barriers result in significant irreversible partial, or in some instances total, loss of the active agent or its biological activity between the site of administration and the target. Consequently, the quantity of active agent that is required to elicit a proper response, such as a therapeutic response, may not reach the target. Therefore, active agents require some assistance in reaching and then in crossing these membranes or lipid bilayers.

The present invention effects active agent delivery by creating a reversibly non-covalently complexed supramolecule from the active agent and complexing perturbant. As a result, the three-dimensional structure or conformation of the active agent is changed, but the chemical composition of the active agent molecule is not altered. This alteration in structure (but not composition) provides the active agent with the appropriate solubility (log P) to cross or penetrate the membrane or lipid bilayer and to resist enzymatic degradation and the like. Crossing refers to transport from one side of the cell membrane or lipid bilayer to the opposite side (i.e. from the outside or exterior to the inside or interior of a cell and/or visa versa), whether the cell membrane or lipid bilayer is actually penetrated or not. Additionally, the perturbed intermediate state of the active agent or the supramolecular complex itself can be used as a template for the preparation of mimetics which would, accordingly, be transportable across a cell membrane or a lipid bilayer. After crossing the cell membrane or lipid bilayer, an active agent has biological activity and bioavailability, either by restoration to the native state or by retaining biological activity or bioavailability acquired in the intermediate state. The mimetic acts similarly after crossing the cell membrane or lipid bilayer.

Active Agents

The native conformational state of an active agent is typically described as the three dimensional state with the lowest free energy ($\Delta G$). It is the state in which the active agent typically possesses the full complement of activity ascribed to the agent, such as the full complement of biological activity ascribed to a biologically active agent.

The denatured conformational state is the state in which the active agent has no secondary or tertiary structure.

Intermediate conformational states exist between the native and denatured states. A particular active agent may have one or more intermediate states. The intermediate state achieved by the present invention is structurally and energetically distinct from both the native and denatured states. Active agents useful in the present invention must be transformable from their native conformational state to a transportable intermediate conformational state and back to their native state, i.e. reversibly transformable, so that when the active agent reaches its target, such as when an orally delivered drug reaches the circulatory system, the active agent retains, regains, or acquires a biologically, pharmacologically, or therapeutically significant complement of its desired biological activity. Preferably the $\Delta G$ of the intermediate state ranges from about −20 Kcal/mole to about 20 Kcal/mole, and most preferably, it ranges from about −10 Kcal/mole to about 10 Kcal/mole.

For example in the case of a protein, the intermediate state has significant secondary structure, significant compactness due to the presence of a sizable hydrophobic core, and a tertiary structure reminiscent of the native fold but without necessarily exhibiting the packing of the native state. The difference in free energy ($\Delta G$) between the intermediate state and the native state is relatively small. Hence, the equilibrium constant between the native and the transportable, reversible intermediate state(s) is close to unity (depending upon experimental conditions). Intermediate states can be confirmed by, for example, differential scanning calorimetry (DSC), isothermal titration calorimetry (ITC), native gradient gels, NMR, fluorescence, and the like.

Without being bound by any theory, applicants believe that the physical chemistry of the intermediate state can be understood by the following explanation relating to proteinaceous active agents. Proteins can exist in stable intermediate conformations that are structurally and energetically distinct from either the native state or the denatured state. The inherent stability of any conformation(s) of any protein is reflected in the Gibbs free energy of the conformation(s). The Gibbs free energy for any state of a monomeric protein is described thermodynamically by the following relationship:

$$\Delta G^\circ = \Delta H^\circ(T_R) - T\Delta S^\circ(T_R) + \Delta Cp^\circ((T-T_R) - T\ln(T/T_R)) \quad (1)$$

where T is the temperature, $T_R$ is a reference temperature, $\Delta H^\circ(T_R)$ and $T\Delta S^\circ(T_R)$ are the relative enthalpy and entropy of this state at the reference temperature, and $\Delta Cp^\circ$ is the relative heat capacity of this state. It is convenient to chose the native state as the reference state to express all relative thermodynamic parameters.

The sum of the statistical weights of all states accessible to the protein is defined as the partition function G:

$$Q = \sum_{i=0}^{n} e^{-\Delta Gi/RT} \quad (2)$$

Equation 2 can also be written as $$Q = 1 + \sum^{n-1} e^{-\Delta Gi/RT} + e^{-\Delta Gn/RT} \quad (3)$$

where the second term includes all the intermediates that become populated during the transition. The first and last terms of equation (3) are the statistical weights of the native and denatured states, respectively. Under most conditions, protein structure could be approximated by a two-state transition function:

$$Q \approx 1 + e^{-\Delta Gn/RT} \quad (4)$$

See, Tanford, C., *Advances in Protein Chemistry,* 1968, 23, 2–95. Conformations of proteins that are intermediate between the native state and the denatured state can be detected by, for example, NMR, calorimetry, and fluorescence. Dill, K. A., Shortle, D., *Annu. Rev. Biochem.* 60, 1991, 795–825.

All thermodynamic parameters can be expressed in terms of the partition function. Specifically the population of molecules in state i is given in equation (5)

$$Pi = \frac{e^{-\Delta Gi/RT}}{Q} \quad (5)$$

Therefore, measurement of the appropriate terms in equation (1) that would allow for the calculation of the Gibbs free energy would determine the extent to which any intermediate state(s) is populated to any significant degree under defined experimental conditions. This in turn indicates the role that these intermediate state(s) play in drug delivery. The more populated the intermediate state, the more efficient the delivery.

Active agents suitable for use in the present invention include biologically active agents and chemically active agents, including, but not limited to, fragrances, as well as other active agents such as, for example, cosmetics.

Biologically active agents include, but are not limited to, pesticides, pharmacological agents, and therapeutic agents. For example, biologically active agents suitable for use in the present invention include, but are not limited to, peptides, and particularly small peptides; hormones, and particularly hormones which by themselves do not or only pass slowly through the gastrointestinal mucosa and/or are susceptible to chemical cleavage by acids and enzymes in the gastrointestinal tract; polysaccharides, and particularly mixtures of mucopolysaccharides; carbohydrates; lipids; or any combination thereof. Further examples include, but are not limited to, human growth hormones; bovine growth hormones; growth releasing hormones; interferons; interleukin-1; insulin; heparin, and particularly low molecular weight heparin; calcitonin; erythropoietin; atrial naturetic factor; antigens; monoclonal antibodies; somatostatin; adrenocorticotropin, gonadotropin releasing hormone; oxytocin; vasopressin; cromolyn sodium (sodium or disodium chromoglycate); vancomycin; desferrioxamine (DFO); antimicrobials, including, but not limited to anti-fungal agents; or any combination thereof.

The methods and compositions of the present invention may combine one or more active agents.

Perturbants

Perturbants serve two purposes in the present invention. In a first embodiment, the active agent is contacted with a perturbant which reversibly transforms the active agent from the native state to the intermediate transportable state. The perturbant non-covalently complexes with the active agent to form a supramolecular complex which can permeate or cross cell membranes and lipid bilayers. This supramolecular complex can be used as a template for the design of a mimetic or can be used as a delivery composition itself. The perturbant, in effect, fixes the active agent in the transportable intermediate state. The perturbant can be released from the supramolecular complex, such as by dilution in the circulatory system, so that the active agent can return to the native state. Preferably, these perturbants have at least one hydrophilic (i.e. readily soluble in water, such as for example, a caroxylate group) and at least one hydrophobic moiety (i.e. readily soluble in an orginac solvent such as, for example, a benzene group), and have a molecular weight ranging from about 150 to about 600 daltons and most preferably from about 200 to about 500 daltons.

Complexing perturbant compounds include, but are not limited to proteinoids including linear, non-linear, and cyclic proteinoids; modified (acylated or sulfonated) amino acids, poly amino acids, and peptides; modified amino acid, poly amino acid, or peptide derivatives (ketones or aldehydes); dilketopiperazine/amino acid constructs; carboxylic acids; and various other perturbants discussed below.

Again without being bound by any theory, applicant believes that the non-covalent complexing may be effected by intermolecular forces including but not limited to, hydrogen bonding, hydrophilic interactions, electrostatic interactions, and Van der Waals interactions. For any given active agent/perturbant supramolecular complex, there will exist some combination of the aforementioned forces that maintain the association.

The association constant $K_a$ between the perturbant and the active agent can be defined according to equation (6)

$$Ka=e^{-\Delta G/RT} \qquad (6)$$

The dissociation constant $K_d$ is the reciprocal of $K_a$. Thus measurement of the association constants between perturbant and active agent at a defined temperature will yield data on the molar Gibbs free energy which allows for the determination of the associated enthalpic and entropic effects. Experimentally these measurements can be made, for example, using NMR, fluorescence or calorimetry.

This hypothesis can be illustrated with proteins in the following manner:

Protein unfolding can be described according to the equilibrium that exists between its various conformational states, e.g.

$$N \overset{k_1}{\longleftrightarrow} / \overset{k_2}{\longleftrightarrow} D \qquad (7)$$

where N is the native state, I is the intermediate state(s), D is the denatured state, and $k_1$ and $k_2$ are the respective rate constants. $K_1$ and $K_2$ are the respective equilibrium constants. Accordingly, $$Q = \sum_{i=0}^{n} e^{-\Delta Gi/RT} \qquad (2)$$

$$= 1 + e^{-\Delta G_1/RT} + e^{-\Delta G_2/RT}$$

$$= 1 + K_1 + K_2 \qquad (8)$$

$$= 1 + k_1 + k_1 k_2 \qquad (9)$$

This suggests that increasing the partition function of the intermediate state(s) should have a positive impact on the ability to deliver the active agent, i.e.

$$P_I = K_1/(1+K_1+K_2) \qquad (10)$$

Because complexing must be reversible, the complexing of the perturbant with the active agent, as measured by the $K_a$, must be strong enough to insure delivery of the drug either to the systemic circulation and/or to the target(s), but not so strong so that disengagement of the perturbant will not occur in a timely manner to allow the active agent to renature if necessary to produce the desired effect(s).

In a second embodiment, perturbants reversibly transform the active agent to the intermediate state so that the conformation of that state can be used as a template for the preparation of mimetics. Perturbants for this purpose need not, but may, complex with the active agent. Therefore, in addition to the complexing perturbants discussed above, perturbants that change the pH of the active agent or its environment, such as for example, strong acids or strong bases; detergents; perturbants that change the ionic strength of the active agent or its environment; other agents such as for example, guanidine hydrochloride; and temperature can be used to transform the active agent. Either the supramolecular complex or the reversible intermediate state can be used as a template for mimetic design.

Complexing Perturbants

Amino acids are the basic materials used to prepare many of the complexing perturbants useful in the present invention. An amino acid is any carboxylic acid having at least one free amine group and includes naturally occurring and synthetic amino acids. The preferred amino acids for use in the present invention are -amino acids, and most preferably are naturally occurring -amino acids. Many amino acids and amino acid esters are readily available from a number of commercial sources such as Aldrich Chemical Co. (Milwaukee, Wis., USA); Sigma Chemical Co. (St. Louis, Mo., USA); and Fluka Chemical Corp. (Ronkonkoma, N.Y., USA).

Representative, but not limiting, amino acids suitable for use in the present invention are generally of the formula

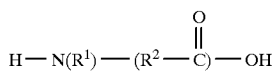

I wherein:

$R^1$ is hydrogen, $C_1$–$C_4$ alkyl, or $C_2$–$C_4$ alkenyl;

$R^2$ is $C_1$–$C_{24}$ alkyl, $C_2$–$C_{24}$ alkenyl, $C_3$–$C_{10}$ cycloalkyl, $C_3$–$C_{10}$ cycloalkenyl, phenyl, naphthyl, ($C_1$–$C_{10}$ alkyl) phenyl, ($C_2$–$C_{10}$ alkenyl) phenyl, ($C_1$–$C_{10}$ alkyl) naphthyl, ($C_2$–$C_{10}$ alkenyl) naphthyl, phenyl ($C_1$–$C_{10}$ alkyl), phenyl ($C_2$–$C_{10}$ alkenyl), naphthyl ($C_1$–$C_{10}$ alkyl), or naphthyl ($C_2$–$C_{10}$ alkenyl);

$R^2$ being optionally substituted with $C_1$–$C_4$ alkyl, $C_2$–$C_4$ alkenyl, $C_1$–$C_4$ alkoxy, —OH, —SH, —$CO_2R^3$, $C_3$–$C_{10}$ cycloalkyl, $C_3$–$C_{10}$ cycloalkenyl, heterocycle having 3–10 ring atoms wherein the hetero atom is one or more of N, O, S, or any combination thereof, aryl, ($C_1$–$C_{10}$ alk)aryl, ar($C_1$–$C_{10}$ alkyl) or any combination thereof;

$R^2$ being optionally interrupted by oxygen, nitrogen, sulfur, or any combination thereof; and $R^3$ is hydrogen, $C_1$–$C_4$ alkyl, or $C_2$–$C_4$ alkenyl.

The preferred naturally occurring amino acids for use in the present invention as amino acids or components of a peptide are alanine, arginine, asparagine, aspartic acid, citrulline, cysteine, cystine, glutamine, glycine, histidine, isoleucine, leucine, lysine, methionine, ornithine, phenylalanine, proline, serine, threonine, tryptophan, tyrosine, valine, hydroxy proline, γ-carboxyglutamate, phenylglycine, or O-phosphoserine. The preferred amino acids are arginine, leucine, lysine, phenylalanine, tyrosine, tryptophan, valine, and phenylglycine.

The preferred non-naturally occurring amino acids for use in the present invention are β-alanine, α-amino butyric acid, γ-amino butyric acid, γ-(aminophenyl) butyric acid, α-amino isobutyric acid, citrulline, ε-amino caproic acid, 7-amino heptanoic acid, β-aspartic acid, aminobenzoic acid, aminophenyl acetic acid, aminophenyl butyric acid, γ-glutamic acid, cysteine (ACM), ε-lysine, ε-lysine (A-Fmoc), methionine sulfone, norleucine, norvaline, ornithine, d-ornithine, p-nitro-phenylalanine, hydroxy proline, 1,2,3,4,-tetrahydroisoquinoline-3-carboxylic acid, and thioproline.

Poly amino acids are either peptides or two or more amino acids linked by a bond formed by other groups which can be linked, e.g., an ester, anhydride or an anhydride linkage. Special mention is made of non-naturally occurring poly amino acids and particularly non-naturally occurring hetero-poly amino acids, i.e. of mixed amino acids.

Peptides are two or more amino acids joined by a peptide bond. Peptides can vary in length from di-peptides with two amino acids to polypeptides with several hundred amino acids. See, Walker, *Chambers Biological Dictionary*, Cambridge, England: Chambers Cambridge, 1989, page 215. Special mention is made of non-naturally occurring peptides and particularly non-naturally occurring peptides of mixed amino acids. Special mention is also made of di-peptides tri-peptides, tetra-peptides, and penta-peptides, and particularly, the preferred peptides are di-peptides and tri-peptides. Peptides can be homo- or hetero-peptides and can include natural amino acids, synthetic amino acids, or any combination thereof.

Proteinoid Complexing Perturbants

Proteinoids are artificial polymers of amino acids. The proteinoids preferably are prepared from mixtures of amino acids. Preferred proteinoids are condensation polymers, and most preferably, are thermal condensation polymers. These polymers may be directed or random polymers. Proteinoids can be linear, branched, or cyclical, and certain proteinoids can be units of other linear, branched, or cyclical proteinoids.

Special mention is made of diketopiperazines. Diketopiperizines are six member ring compounds. The ring includes two nitrogen atoms and is substituted at two carbons with two oxygen atoms. Preferably, the carbonyl groups are at the 1 and 4 ring positions. These rings can be optionally, and most often are, further substituted.

Diketopiperazine ring systems may be generated during thermal polymerization or condensation of amino acids or amino acid derivatives. (Gyore, J; Ecet M. *Proceedings Fourth ICTA* (*Thermal Analysis*), 1974, 2, 387–394 (1974)). These six membered ring systems were presumably generated by intra-molecular cyclization of the dimer prior to further chain growth or directly from a linear peptide (Reddy, A. V., *Int. J. Peptide Protein Res.*, 40, 472–476 (1992); Mazurov, A. A. et al., *Int. J. Peptide Protein Res.*, 42, 14–19 (1993)).

Diketopiperazines can also be formed by cyclodimerization of amino acid ester derivatives as described by Katchalski et al., *J. Amer. Cheir. Soc.*, 68, 879–880 (1946), by cyclization of dipeptide ester derivatives, or by thermal dehydration of amino acid derivatives and high boiling solvents as described by Kopple et al., *J. Org. Chem.*, 33 (2), 862–864 (1968).

In a typical synthesis of a diketopiperazine, the COOH group(s) of an amino acid benzyl ester are activated in a first step to yield a protected ester. The amine is deprotected and cyclized via dimerization in a second step, providing a diketopiperazine di-ester. Finally, the COOH group(s) are deprotected to provide the diketopiperazine.

Diketopiperazines typically are formed from α-amino acids. Preferably, the α-amino acids of which the diketopiperazines are derived are glutamic acid, aspartic acid, tyrosine, phenylalanine, and optical isomers of any of the foregoing.

Special mention is made of diketopiperizines of the formula

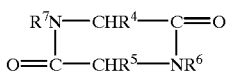

II wherein $R^4$ $R^5$, $R^6$, and $R^7$ independently are hydrogen, $C_1$–$C_{24}$ alkyl, $C_1$–$C_{24}$ alcenyl, phenyl, naphthyl, ($C_1$–$C_{10}$ alkyl)phenyl, ($C_1$–$C_{10}$ alkenyl)phenyl, ($C_1$–$C_{10}$ allkyl) naphthyl, ($C_1$–$C_{10}$ alkenyl)naphthyl, phenyl ($C_1$–$C_{10}$ alkyl), phenyl($C_1$–$C_{10}$ alkenyl), naphthyl ($C_1$–$C_{10}$ alkyl), and naphthyl ($C_1$–$C_{10}$ alkenyl); any of $R^4$, $R^5$, $R^6$, and $R^7$ independently may optionally be substituted with $C_1$–$C_4$ alkyl, $C_1$–$C_4$ alkenyl, $C_1$–$C_4$ alkoxy, —OH, —SH, and —$CO_2R^8$ or any combination thereof; $R^8$ is hydrogen, $C_1$–$C_4$ alkyl or $C_1$–$C_4$ alkenyl; and any of $R^4$, $R^5$, $R^6$, and $R^7$ independently may optionally be interrupted by oxygen, nitrogen, sulfur, or any combination thereof.

The phenyl or naphthyl groups may optionally be substituted. Suitable, but non-limiting, examples of substituents are $C_1$–$C_6$ alkyl, $C_1$–$C_6$ alkenyl, $C_1$–$C_6$ alkoxy, —OH, —SH, or $CO_2R^9$ wherein $R^9$ is hydrogen, $C_1$–$C_6$ alkyl, or $C_1$–$C_6$ alkenyl.

Preferably, $R^6$ and $R^7$ independently are hydrogen, $C_1$–$C_4$ alkyl or $C_1$–$C_4$ alkenyl. Special mention is made of diketopiperazines which are preferred complexing perturbants. These diketopiperazines include the unsubstituted diketopiperazine in which $R^4$, $R^5$, $R^6$, and $R^7$ are hydrogen, and diketopiperazines which are substituted at one or both of the nitrogen atoms in the ring, i.e. mono or di-N-substituted. Special mention is made of the N-substituted diketopiperazine wherein one or both of the nitrogen atoms is substituted with a methyl group.

Special mention is also made of diketopiperizines of the formula

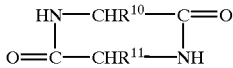

III wherein $R^{10}$ and $R^{11}$ independently are hydrogen, $C_1$–$C_{24}$ alkyl, $C_1$–$C_{24}$ alkenyl, phenyl, naphthyl, ($C_1$–$C_{10}$ alkyl) phenyl, ($C_1$–$C_{10}$ alkenyl)phenyl, ($C_1$–$C_{10}$ alkyl)naphthyl, ($C_1$–$C_{10}$ alkenyl)naphthyl, phenyl ($C_1$–$C_{10}$ alkyl), phenyl ($C_1$–$C_{10}$ alkenyl), naphthyl ($C_1$–$C_{10}$ alkyl), and naphthyl ($C_1$–$C_{10}$ alkenyl); but both $R^{10}$ and $R^{11}$ can not be hydrogen; either or both $R^{10}$ or $R^{11}$ independently may optionally be substituted with $C_1$–$C_4$ allkyl, $C_1$–$C_4$ alkenyl, $C_1$–$C_4$ alkoxy, —OH, —SH, and —$CO_2R^{12}$ or any combination thereof; $R^{12}$ is hydrogen, $C_1$–$C_4$ alkyl or $C_1$–$C_4$ alkenyl; and either or both $R^{10}$ and $R^{11}$ independently may optionally be interrupted by oxygen, nitrogen, sulfur, or any combination thereof.

The phenyl or naphthyl groups may optionally be substituted. Suitable, but non-limiting, examples of substituents are $C_1$–$C_6$ alkyl, $C_1$–$C_6$ alkenyl, $C_1$–$C_6$ alkoxy, —OH, —SH, or $CO_2R^{13}$ wherein $R^{13}$ is hydrogen, $C_1$–$C_6$ alkyl, or $C_1$–$C_6$ alkenyl. When one of $R^{10}$ or $R^{11}$ is hydrogen, the diketopiperazine is mono-carbon-(C)-substituted. When neither $R^{10}$ nor $R^{11}$ is hydrogen, the diketopiperazine is di-carbon-(C)-substituted.

Preferably, $R^{10}$, $R^{11}$, or both $R^{10}$ and $R^{11}$, contain at least one functional group, a functional group being a non-hydrocarbon portion responsible for characteristic reactions of the molecule. Simple functional groups are heteroatoms including, but not limited to halogens, oxygen, sulfur, nitrogen, and the like, attached to, the carbon of an alkyl group by a single or multiple bond. Other functional groups include, but are not limited to, for example, hydroxyl groups, carboxyl groups, amide groups, amine groups, substituted amine groups, and the like.

Preferred diketopiperazines are those which are substituted at one or two of the carbons of the ring with a functional group that includes at least one carboxyl functionality.

Amino Acid(s)/Diketopiperazine Complexing Perturbants

Diketopiperizines may also be polymerized with additional amino acids to form constructs of at least one amino acid or an ester or an amide thereof and at least one diketopiperazine, preferably covalently bonded to one another.

When the diketopiperazine is polymerized with additional amino acids, one or more of the R groups must contain at least one functional group, a functional group being a non-hydrocarbon portion responsible for characteristic reactions of the molecule. Simple functional groups are heteroatoms including, but not limited to halogens, oxygen, sulfur, nitrogen, and the like, attached to, the carbon of an alkyl group by a single or multiple bond. Other functional groups include, but are not limited to, for example, hydroxyl groups, carboxyl groups, amide groups, amine groups, substituted amine groups, and the like.

Special mention is also made of diketopiperazines which are preferred components of the amino acids/diketopiperazine perturbants of the present invention. Such preferred diketopiperazines are those which are substituted at one or two of the carbons of the ring and preferably are substituted with a functional group that includes at least one carboxyl functionality.

Most preferably, the diketopiperazines in the amino acids/diketopiperazine perturbants are prepared from trifunctional amino acids such as L-glutamic acid and L-aspartic acid which cyclize to form diketopiperazines.

The diketopiperazines can generate a bis-carboxylic acid platform which can be further condensed with other amino acids to form the perturbant. Typically, the diketopiperazine will react and covalently bond with one or more of the amino acids through the functional group(s) of the R groups of the diketopiperazines. These unique systems, because of the cis-geometry imparted by the chiral components of the diketopiperazine ring (Lannom, H. K. et al., *Int. J. Peptide Protein Res.*, 28, 67–78 (1986)), provide an opportunity to systematically alter the structure of the terminal amino acids while holding the orientation between them fixed relative to non-cyclic analogs (Fusaoka et al., *Int. J. Peptide Protein Res.*, 34, 104–110 (1989); Ogura, H. et al., *Chem. Pharma. Bul.*, 23, 2474–2477 (1975). See also, Lee, B. H. et al. *J. Org. Chem.*, 49, 2418–2423 (1984); Buyle, R., *Helv. Chim. Acta*, 49, 1425, 1429 (1966). Other methods of polymerization known to those skilled in the art may lend themselves to amino acid/diketopiperazine polymerization as well.

The amino acids/diketopiperazine perturbants may include one or more of the same or different amino acids as well as one or more of the same or different diketopiperazines as described above.

Ester and amide derivatives of these amino acids/diketopiperazine perturbants are also useful in the present invention.

Modified Amino Acid Complexing Perturbants

Modified amino acids, poly amino acids or peptides are either acylated or sulfonated and include amino acid amides and sulfonamides.

Acylated Amino Acid Complexing Perturbants

Special mention is made of acylated amino acids having the formula $$Ar-Y-(R^{14})_n-OH \qquad IV$$

wherein Ar is a substituted or unsubstituted phenyl or naphthyl;
Y is

$R^{14}$ has the formula

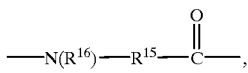

wherein:
$R^{15}$ is $C_1$ to $C_{24}$ alkyl, $C_1$ to $C_{24}$ alkenyl, phenyl, naphthyl, ($C_1$ to $C_{10}$ alkyl) phenyl, ($C_1$ to $C_{10}$ alkenyl) phenyl, ($C_1$ to $C_{10}$ alkyl) naphthyl, ($C_1$ to $C_{10}$ alkenyl)

naphthyl, phenyl ($C_1$ to $C_{10}$ alkyl), phenyl ($C_1$ to $C_{10}$ alkenyl), naphthyl ($C_1$ to $C_{10}$ alkyl) and naphthyl ($C_1$ to $C_{10}$ alkenyl);

$R^{15}$ is optionally substituted with $C_1$ to $C_4$ alkyl, $C_1$ to $C_4$ alkenyl, $C_1$ to $C_4$ alkoxy, —OH, —SH and —$CO_2R^5$, cycloalkyl, cycloalkenyl, heterocyclic alkyl, alkaryl, heteroaryl, heteroalkaryl, or any combination thereof;

$R^{17}$ is hydrogen, $C_1$ to $C_4$ alkyl or $C_1$ to $C_4$ alkenyl;

$R^{15}$ is optionally interrupted by oxygen, nitrogen, sulfur or any combination thereof; and $R^{16}$ is hydrogen, $C_1$ to $C_4$ alkyl or $C_1$ to $C_4$ alkenyl.

Special mention is also made of those having the formula

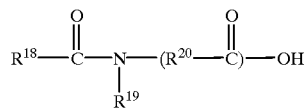

V wherein:

$R^{18}$ is (i) $C_3$–$C_{10}$ cycloalkyl, optionally substituted with $C_1$–$C_7$ alkyl, $C_2$–$C_7$ alkenyl, $C_1$–$C_7$ alkoxy, hydroxy, phenyl, phenoxy or —$CO_2R^{21}$, wherein $R^1$ is hydrogen, $C_1$–$C_4$ alkyl, or $C_2$–$C_4$ alkenyl; or (ii) $C_1$–$C_6$ alkyl substituted with $C_3$–$C_{10}$ cycloalkyl;

$R^{19}$ is hydrogen, $C_1$–$C_4$ alkyl, or $C_2$–$C_4$ alkenyl;

$R^{20}$ is $C_1$–$C_{24}$ alkyl, $C_2$–$C_{24}$ alkenyl, $C_3$–$C_{10}$ cycloalkyl, $C_3$–$C_{10}$ cycloalkenyl, phenyl, naphthyl, ($C_1$–$C_{10}$ alkyl) phenyl, ($C_2$–$C_{10}$ alkenyl) phenyl, ($C_1$–$C_{10}$ alkyl) naphthyl, ($C_2$–$C_{10}$ alkenyl) naphthyl, phenyl ($C_1$–$C_{10}$ alkyl), phenyl ($C_2$–$C_{10}$ alkenyl), naphthyl ($C_1$–$C_{10}$ alkyl) or naphthyl ($C_2$–$C_{10}$ alkenyl);

$R^{20}$ being optionally substituted with $C_1$–$C_4$ alkyl, $C_2$–$C_4$ alkenyl, $C_1$–$C_4$ alkoxy, —OH, —SH, —$CO_2R^{22}$, $C_3$–$C_{10}$ cycloalkyl, $C_3$–$C_{10}$ cycloalkenyl, heterocycle having 3–10 ring atoms wherein the hetero atom is one or more of N, O, S or any combination thereof, aryl, ($C_1$–$C_{10}$ alk)aryl, ar($C_1$–$C_{10}$ alkyl), or any combination thereof;

$R^{20}$ being optionally interrupted by oxygen, nitrogen, sulfur, or any combination thereof; and $R^{22}$ is hydrogen, $C_1$–$C_4$ alkyl, or $C_2$–$C_4$ alkenyl.

Some preferred acylated amino acids include salicyloyl phenylalanine, and the compounds having the formulas:

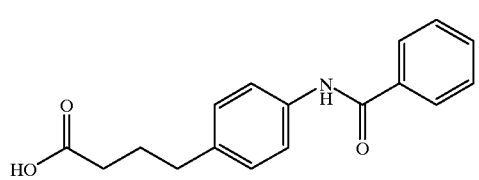

VI

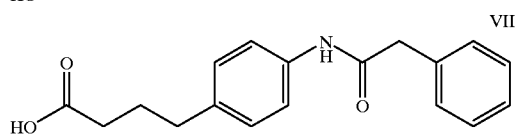

VII

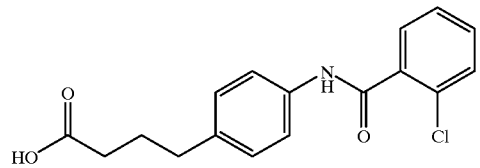

VIII

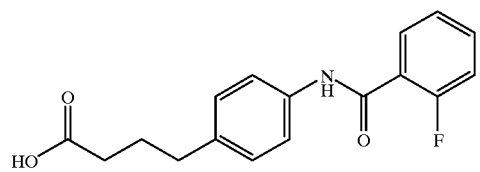

IX

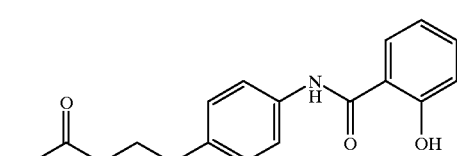

X

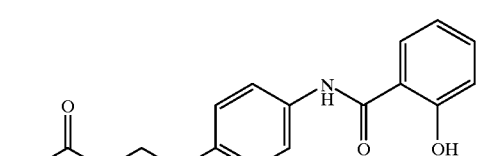

XI

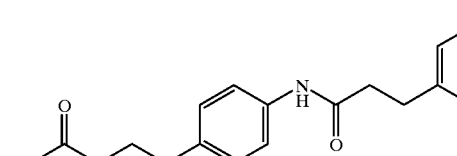

XII

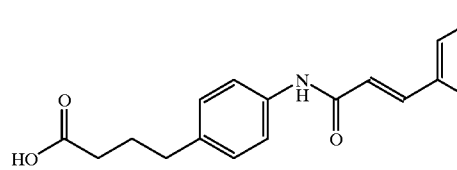

XIII

XIV

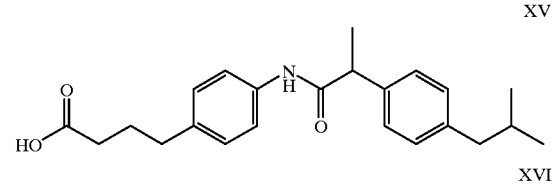

XV

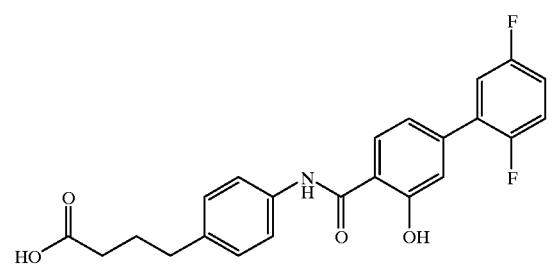

XVI

XVII
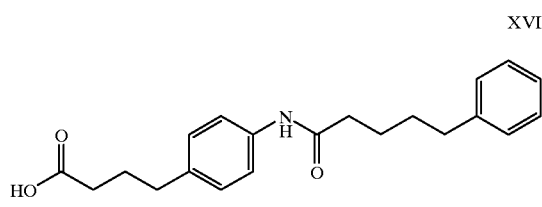
XVIII
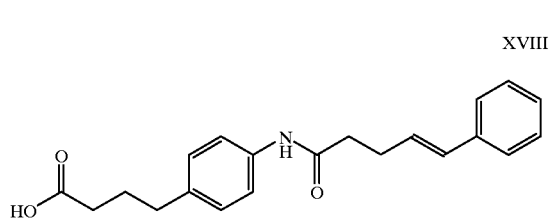
XIX
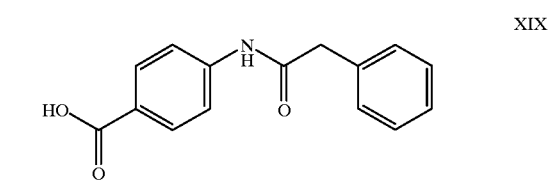
XX
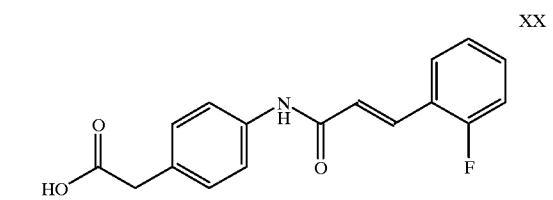
XXI
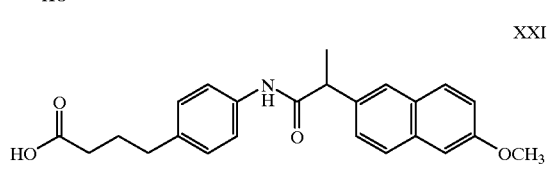
XXII
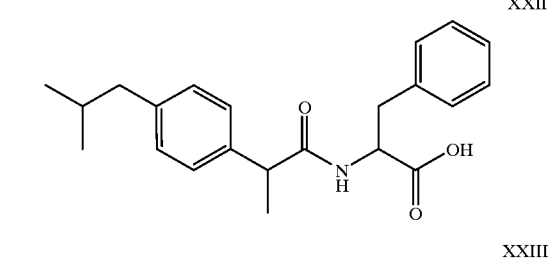
XXIII
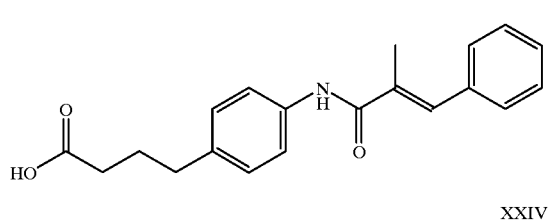
XXIV
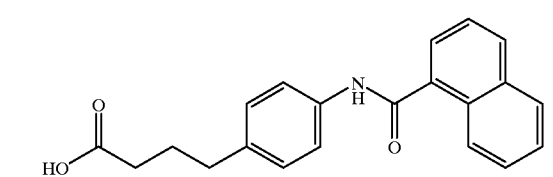
XXV
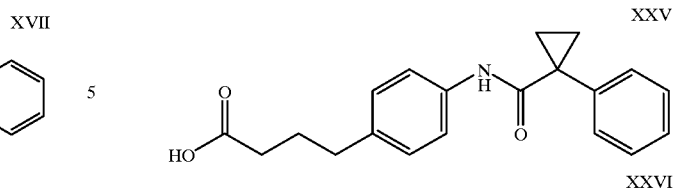
XXVI
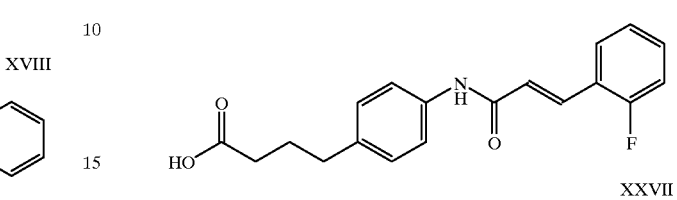
XXVII
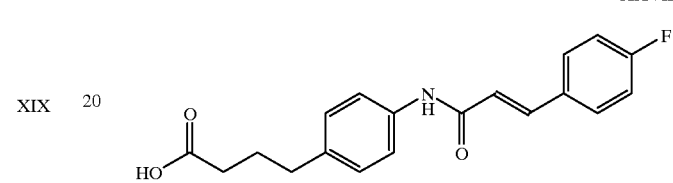
XXVIII
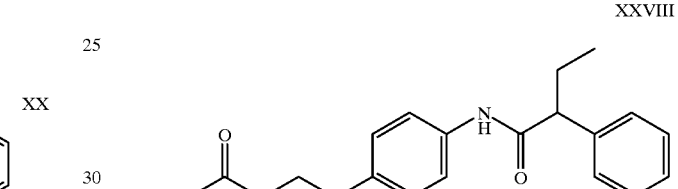
XXIX
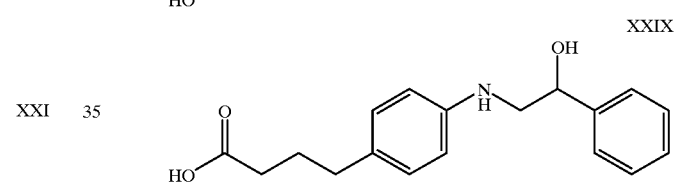
XXX
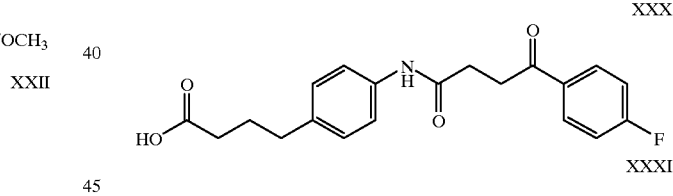
XXXI
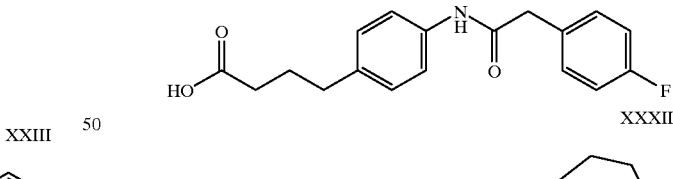
XXXII
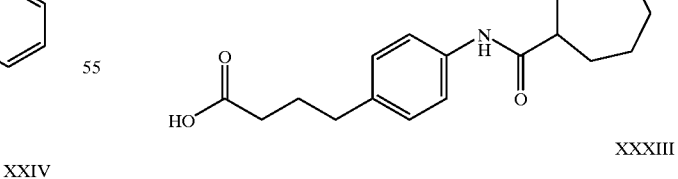
XXXIII
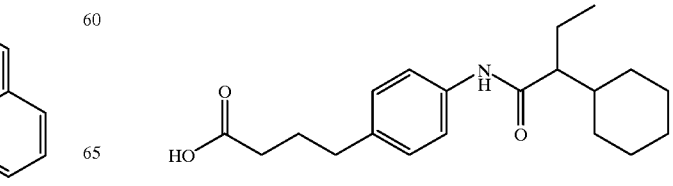

XXXIV
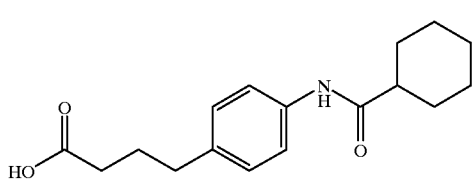
XXXV
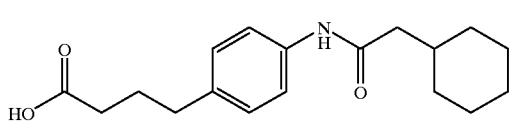
XXXVI
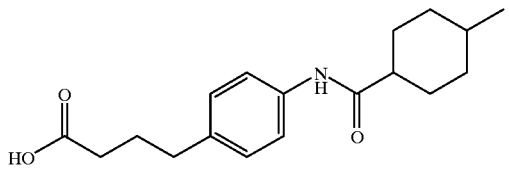
XXXVII
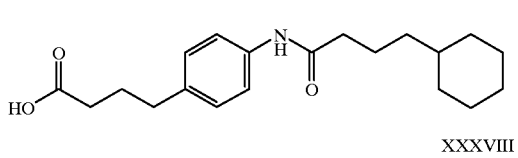
XXXVIII
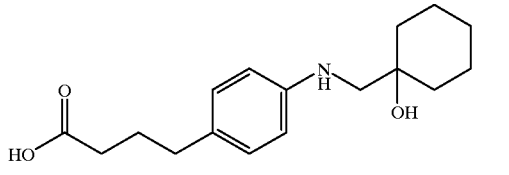
XXXIX
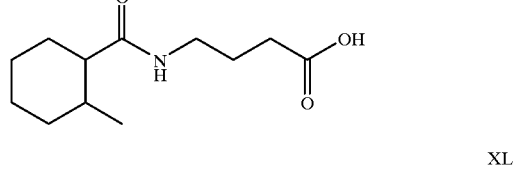
XL
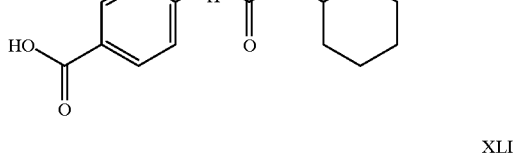
XLI
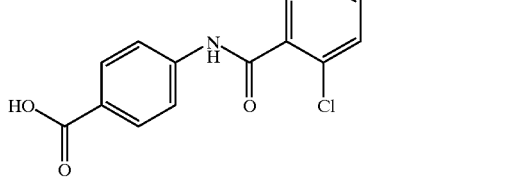
XLII
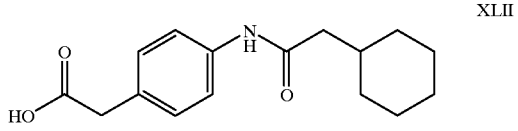
XLIIA
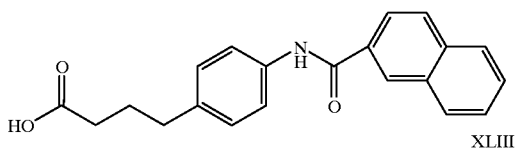
XLIII
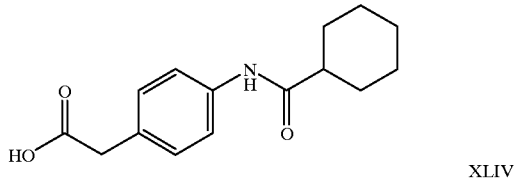
XLIV
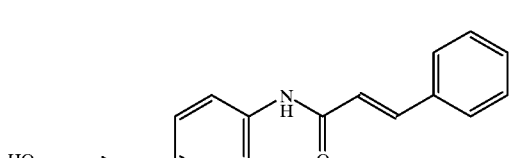
XLV
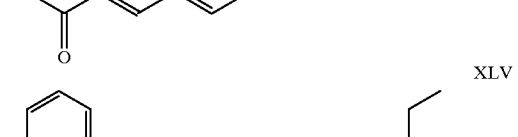
XLVI
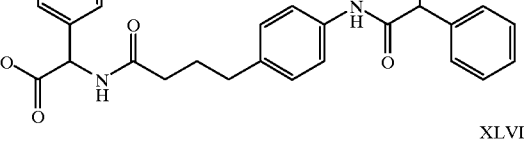
XLVII
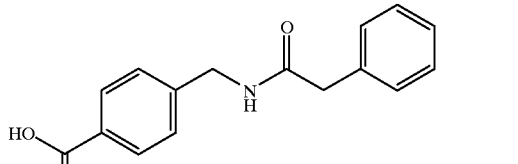
XLVIII
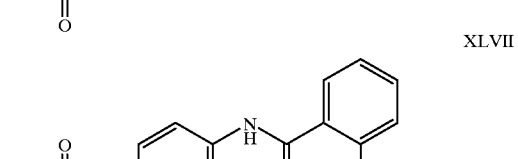
XLVIIIA
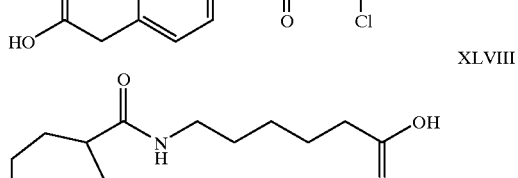

Special mention is made of compounds having the formula:

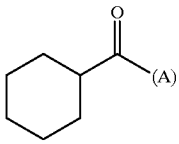

XLIX wherein A is Try, Leu, Arg, Trp, or Cit; and
optionally wherein if A is Try, Arg, Trp or Cit; A is acylated at 2 or more functional groups.

Preferred compounds are those wherein A is Try; A is Tyr and is acrylated at 2 functional groups; A is Arg; A is Arg and is acylated at 2 functional groups; A is Trp; A is Trp and is acylated at 2 functional groups; A is Cit; and A is Cit and is acylated at 2 functional groups.

Special mention is also made of compounds having the formula:

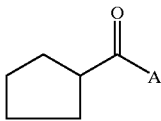

L wherein A is Arg or Leu; and
wherein if A is Arg, A is optionally acylated at 2 or more functional groups;

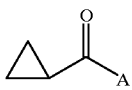

LI where A is Leu or phenylglycine;

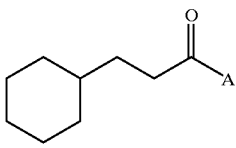

LII wherein A is phenylglycine; and

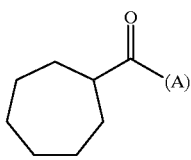

LIII wherein A is phenylglycine.

Acylated amino acids may be prepared by reacting single amino acids, mixtures of two or more amino acids, or amino acid esters with an amine modifying agent which reacts with free amino moieties present in the amino acids to form amides.

Suitable, but non-limiting, examples of acylating agents useful in preparing acylated amino acids include acid chloride acylating agents having the formula

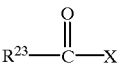

wherein:
$R^{23}$ an appropriate group for the modified amino acid being prepared, such as, but not limited to, alkyl, alkenyl, cycloalkyl, or aromatic, and particularly methyl, ethyl, cyclohexyl, cyclophenyl, phenyl, or bezyl, and X is a leaving group. Typical leaving groups include, but are not limited to, halogens such as chlorine, bromine and iodine.

Examples of the acylating agents include, but are not limited to, acyl halides including, but not limited to, acetyl chloride, propyl chloride, cyclohexanoyl chloride, cyclopentanoyl chloride, and cycloheptanoyl chloride, benzoyl chloride, hippuryl chloride and the like; and anhydrides, such as acetic anhydride, propyl anhydride, cyclohexanoic anhydride, benzoic anhydride, hippuric anhydride and the like. Preferred acylating agents include benzoyl chloride, hippuryl chloride, acetyl chloride, cyclohexanoyl chloride, cyclopentanoyl chloride, and cycloheptanoyl chloride.

The amine groups can also be modified by the reaction of a carboxylic acid with coupling agents such as the carbodiimide derivatives of amino acids, particularly hydrophilic amino acids such as phenylalanine, tryptophan, and tyrosine. Further examples include dicyclohexylcarbodiimide and the like.

If the amino acid is multifunctional, i.e. has more than one —OH, —NH$_2$ or —SH group, then it may optionally be acylated at one or more functional groups to form, for example, an ester, amide, or thioester linkage.

For example, in the preparation of many acylated amino acids, the amino acids are dissolved in an aqueous alkaline solution of a metal hydroxide, e.g., sodium or potassium hydroxide and the acylating agent added. The reaction time can range from about 1 hour and about 4 hours, preferably about 2–2.5 hours. The temperature of the mixture is maintained at a temperature generally ranging between about 5° C. and about 70° C., preferably between about 10° C. and about 50° C. The amount of alkali employed per equivalent of NH$_2$ groups in the amino acids generally ranges between about 1.25 moles and about 3 moles, and is preferably between about 1.5 moles and about 2.25 moles per equivalent of NH$_2$. The pH of the reaction solution generally ranges between about pH 8 and about pH 13, and is preferably between about pH 10 and about pH 12. The amount of amino modifying agent employed in relation to the quantity of amino acids is based on the moles of total free NH$_2$ in the amino acids. In general, the amino modifying agent is employed in an amount ranging between about 0.5 and about 2.5 mole equivalents, preferably between about 0.75 and about 1.25 equivalents, per molar equivalent of total NH$_2$ groups in the amino acids.

The modified amino acid formation reaction is quenched by adjusting the pH of the mixture with a suitable acid, e.g., concentrated hydrochloric acid, until the pH reaches between about 2 and about 3. The mixture separates on standing at room temperature to form a transparent upper layer and a white or off-white precipitate. The upper layer is discarded, and modified amino acids are collected by filtration or decantation. The crude modified amino acids are then mixed with water. Insoluble materials are removed by filtration and the filtrate is dried in vacuo. The yield of modified amino acids generally ranges between about 30 and about 60%, and usually about 45%. The present invention also contemplates amino acids which have been modified by multiple acylation, e.g., diacylation or triacylation.

If amino acid esters or amides are the starting materials, they are dissolved in a suitable organic solvent such as dimethylformamide or pyridine, are reacted with the amino modifying agent at a temperature ranging between about 5° C. and about 70° C., preferably about 25° C., for a period ranging between about 7 and about 24 hours. The amount of amino modifying agents used relative to the amino acid esters are the same as described above for amino acids.

Thereafter, the reaction solvent is removed under negative pressure and optionally the ester or amide functionality can be removed by hydrolyzing the modified amino acid ester with a suitable alkaline solution, e.g., 1 N sodium hydroxide, at a temperature ranging between about 50° C. and about 80° C., preferably about 70° C., for a period of time sufficient to hydrolyze off the ester group and form the modified amino acid having a free carboxyl group. The hydrolysis mixture is then cooled to room temperature and acidified, e.g., with an aqueous 25% hydrochloric acid solution, to a pH ranging between about 2 and about 2.5. The modified amino acid precipitates out of solution and is recovered by conventional means such as filtration or decantation.

The modified amino acids may be purified by acid precipitation, recrystallization or by fractionation on solid column supports. Fractionation may be performed on a suitable solid column supports such as silica gel, alumina, using solvent mixtures such as acetic acid/butanol/water as the mobile phase; reverse phase column supports using trifluoroacetic acid/acetonitrile mixtures as the mobile phase; and ion exchange chromatography using water as the mobile phase. The modified amino acids may also be purified by extraction with a lower alcohol such as methanol, butanol, or isopropanol to remove impurities such as inorganic salts.

The modified amino acids generally are soluble in alkaline aqueous solution (pH≧9.0); partially soluble in ethanol, n-butanol and 1:1 (v/v) toluene/ethanol solution and insoluble in neutral water. The alkali metal salts, e.g., the sodium salt of the derivatized amino acids are generally soluble in water at about a pH of 6–8.

In poly amino acids or peptides, one or more of the amino acids may be modified (acylated). Modified poly amino acids and peptides may include one or more acylated amino acid(s). Although linear modified poly amino acids and peptides will generally include only one acylated amino acid, other poly amino acid and peptide configurations can include more than one acylated amino acid. Poly amino acids and peptides can be polymerized with the acylated amino acid(s) or can be acylated after polymerization.

Special mention is made of the compound:

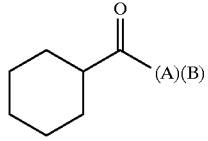

LIV wherein A and B independently are Arg or Leu.
Sulfonated Amino Acid Complexing Perturbants
Sulfonated modified amino acids, poly amino acids, and peptides are modified by sulfonating at least one free amine group with a sulfonating agent which reacts with at least one of the free amine groups present. Special mention is made of compounds of the formula

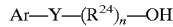

LV wherein Ar is a substituted or unsubstituted phenyl or naphthyl;
Y is —SO$_2$—, R$^{24}$ has the formula

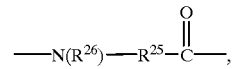

wherein:
R$^{25}$ is C$_1$ to C$_{24}$ alkyl, C$_1$ to C$_{24}$ alkenyl, phenyl, naphthyl, (C$_1$ to C$_{10}$ alkyl) phenyl, (C$_1$ to C$_{10}$ alkenyl) phenyl, (C$_1$ to C$_{10}$ alkyl) naphthyl, (C$_1$ to C$_{10}$ alkenyl) naphthyl, phenyl (C$_1$ to C$_{10}$ alkyl), phenyl (C$_1$ to C$_{10}$ alkenyl), naphthyl (C$_1$ to C$_{10}$ alkyl) and naphthyl (C$_1$ to C$_{10}$ alkenyl);
R$^{25}$ is optionally substituted with C$_1$ to C$_4$ alkyl, C$_1$ to C$_4$ alkenyl, C$_1$ to C$_4$ alkoxy, —OH, —SH and —CO$_2$R$^{27}$ or any combination thereof;
R$^{27}$ is hydrogen, C$_1$ to C$_4$ alkyl or C$_1$ to C$_4$ alkenyl;
R$^{25}$ is optionally interrupted by oxygen, nitrogen, sulfur or any combination thereof; and
R$^{26}$ is hydrogen, C$_1$ to C$_4$ alkyl or C$_1$ to C$_4$ alkenyl.

Suitable, but non-limiting, examples of sulfonating agents useful in preparing sulfonated amino acids include sulfonating agents having the formula R$^{28}$—SO$_2$—X wherein R$^{28}$ is an appropriate group for the modified amino acid being prepared such as, but not limited to, alkyl, alkenyl, cycloalkyl, or aromatics and X is a leaving group as described above. One example of a sulfonating agent is benzene sulfonyl chloride.

Modified poly amino acids and peptides may include one or more sulfonated amino acid(s). Although linear modified poly amino acids and peptides used generally include only one sulfonated amino acid, other poly amino acid and peptide configurations can include more than one sulfonated amino acid. Poly amino acids and peptides can be polymerized with the sulfonated amino acid(s) or can be sulfonated after polymerization.

Modified Amino Acid Derivative Complexing Perturbants
Modified amino acid, polyamino acid, or peptide derivatives are amino acids, poly amino acids, or peptides which have had at least one acyl-terminus converted to an aldehyde or a ketone, and are acylated at at least one free amine group, with an acylating agent which reacts with at least one of the free amine groups present.

Amino acid, poly amino acid, or peptide derivatives can be readily prepared by reduction of amino acid esters or peptide esters with an appropriate reducing agent. For example, amino acid, poly amino acid, or peptide aldehydes can be prepared as described in an article by R. Chen et al., *Biochemistry*, 1979, 18, 921–926. Amino acid, poly amino acid, or peptide ketones can be prepared by the procedure described in *Organic Syntheses, Col. Vol. IV*, Wiley, (1963), page 5. Acylation is discussed above.

For example, the derivatives may be prepared by reacting a single amino acid, poly amino acid, or peptide derivative or mixtures of two or more amino acid or peptide derivatives, with an acylating agent or an amine modifying agent which reacts with free amino moieties present in the derivatives to form amides. The amino acid, poly amino acid, or peptide can be modified and subsequently derivatized, derivatized and subsequently modified, or simultaneously modified and derivatized. Protecting groups may be used to avoid unwanted side reactions as would be known to those skilled in the art.

In modified poly amino acid or peptide derivative, one or more of the amino acid may be derivatized (an aldehyde or a ketone) and/or modified, (acylated) but there must be at least one derivative and at least one modification.

Special mention is made of the modified amino acid derivatives N-cyclohexanoyl-Phe aldehyde, N-acetyl-Phe-aldehyde, N-acetyl-Tyr ketone, N-acetyl-Lys ketone and N-cyclohexanoyl-Leu ketone, and N-cyclohexanoyl phenyl-alanine aldehyde.

Carboxylic Acid Complexing Perturbants

Various carboxylic acids and salts of these carboxylic acids may be used as complexing perturbants. These carboxylic acids have the formula:

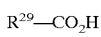

$$R^{29}-CO_2H \qquad \text{LVI}$$

wherein $R^{29}$ is $C_1$ to $C_{24}$ alkyl, $C_2$ to $C_{24}$ alkenyl, $C_3$ to $C_{10}$ cycloalkyl, $C_3$ to $C_{10}$ cycloalkenyl, phenyl, naphthyl, ($C_1$ to $C_{10}$ alkyl)phenyl, ($C_2$ to $C_{10}$ alkenyl) phenyl, ($C_1$ to $C_{10}$ alkyl)naphthyl, ($C_2$ to $C_{10}$ alkenyl) naphthyl, phenyl($C_1$ to $C_{10}$ alkyl), phenyl($C_2$ to $C_{10}$ alkenyl), naphthyl($C_1$ to $C_{10}$ alkyl) and naphthyl($C_2$ to $C_{10}$ alkenyl);

$R^{29}$ being optionally substituted with $C_1$ to $C_{10}$ alkyl, $C_2$ to $C_{10}$ alkenyl, $C_1$ to $C_4$ alkoxy, —OH, —SH, —$CO_2R^3$, $C_3$ to $C_{10}$ cycloalkyl, $C_3$ to $C_{10}$ cycloalkenyl, heterocyclic having 3–10 ring atoms wherein the hetero atom is one or more atoms of N, O, S or any combination thereof, aryl, ($C_1$ to $C_{10}$ alk)aryl, aryl($C_1$ to $C_{10}$)alkyl, or any combination thereof;

$R^{29}$ being optionally interrupted by oxygen, nitrogen, sulfur, or any combination thereof; and $R^{30}$ is hydrogen, $C_1$ to $C_4$ alkyl or $C_2$ to $C_4$ alkenyl.

The preferred carboxylic acids are cyclohexanecarboxylic acid, cyclopentanecarboxylic acid, cycloheptanecarboxylic acid, hexanoic acid, 3-cyclohexanepropanoic acid, methyl-cyclohexanecarboxylic acid, 1,2-cyclohexanedicarboxylic acid, 1,3-cyclohexanedicarboxylic acid, 1,4-cyclohexanedicarboxylic acid, 1-adamantanecarboxylic acid, phenylpropanoic acid, adipic acid, cyclohexanepentanoic acid, cyclohexanebutanoic acid, pentylcyclohexanoic acid, 2-cyclopentanehexanoic acid, cyclohexane pentanoic acid, hexanedioic acid, cyclohexanebutanoic acid, and (4-methylphenyl) cyclohexane acetic acid.

Other Examples of Complexing Perturbants

Although all complexing perturbants which can form the supramolecular complexes described herein are within the scope of the present invention, other examples of complexing perturbants include, but are not limited to, 2-carboxymethyl-phenylalanine-leucine; 2-benzyl succinic acid, an actinonin, phenylsulfonyl aminophenyl-butyric acid,

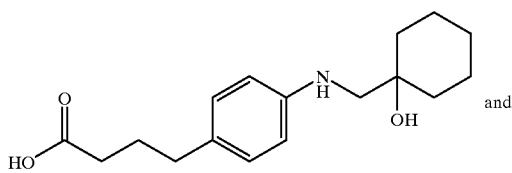

LVII and

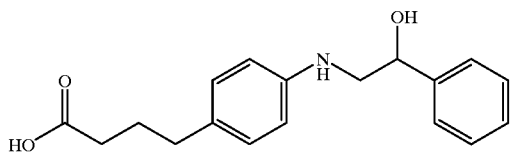

LVIII

Mimetics

Mimetics within the scope of the present invention are constructs which are structural and/or functional equivalents of an original entity. Structural and chemically functional mimetics of the supramolecular complexes and the reversible transportable intermediate states of active agents are not necessarily peptidic, as non-peptidic mimetics can be prepared which have the appropriate chemical and/or structural properties. However, preferred mimetics are peptides which have a different primary structure than the supramolecular complex or the intermediate state, but retain the same secondary and tertiary structure of the supramolecular complex or the intermediate state. Although mimetics may have less bioactivity than a native state or intermediate state active agent or supra molecular comples, the mimetics may possess other important properties which may not be possessed by the native state such as, for example, further increased ability to be delivered orally.

Methods of preparation of such mimetics are described, for example, in Yamazaki et al., *Chirality* 3:268–276 (1991); Wiley et al., *Peptidomimetics Derived From Natural Products*, Medicinal Research Reviews, Vol. 13, No. 3, 327–384 (1993); Gurrath et al., *Eur. J. Biochem* 210:991–921 (1992); Yamazaki et al, *Int. J. Peptide Protein Res.* 37:364–381 (1991); Bach et al., *Int. J. Peptide Protein Res.* 38:314–323 (1991); Clark et al., *J. Med. Chem.* 32:2026–2038 (1989); Portoghese, *J. Med. Chem.* 34:(6) 1715–1720 (1991); Zhou et al., *J. Immunol.* 149 (5) 1763–1769 (Sep. 1, 1992); Holzman et al., *J. Protein Chem.* 10: (5) 553–563 (1991); Masier et al., *Arch. Insect Biochem. and Physiol.* 22:87–111 (1993); Saragovi et al., *Biotechnology* 10: (July 1992); Olmsteel et al., *J. Med. Chem.* 36:(1) 179–180 (1993); Malin et al. *Peptides* 14:47–51 (1993); and Kouns et al., *Blood* 80:(10) 2539–2537 (1992); Tanaka et al., *Biophys. Chem.* 50 (1994) 47–61; DeGrado et al., *Science* 243 (Feb. 3, 1989); Regan et al., *Science* 241: 976–978 (Aug. 19, 1988); Matouschek et al, *Nature* 340: 122–126 (Jul. 13, 1989); Parker et al., *Peptide Research* 4: (6) 347–354 (1991); Parker et al., *Peptide Research* 4:(6) 355–363 (1991); Federov et al., *J. Mol. Biol.* 225: 927–931 (1992); Ptitsyn et al., *Biopolymers* 22: 15–25 (1983); Ptitsyn et al., *Protein Engineering* 2:(6) 443–447 (1989).

For example, protein structures are determined by the collective intra- and inter-molecular interactions of the constituent amino acids. In alpha helices, the first and fourth amino acid in the helix interact non-covalently with one another. This pattern repeats through the entire helix except for the first four and last four amino acids. In addition, the side chains of amino acids can interact with one another. For example, the phenyl side chain of phenylaline would probably not be solvent exposed if that phenylalanine were found-in a helix. If the interactions of that phenylalanine contributed to helix stability then substituting an alanine for a phenylalanine would disrupt the helix and change the conformation of a protein.

Therefore, a mimetic could be created by first determining which amino acid side chains became solvent exposed and thus removed from contributing to stabilization of the native state such as by the technique of scanning mutagenesis. Mutants containing amino acid substitutions at those same sights could be created so that the substituted amino acids would render the protein conformation more intermediate-like that native-like. Confirmation that the appropriate structure had been synthesized could come from spectroscopy and other analytical methods.

Delivery Compositions

Delivery compositions which include the supramolecular complex described above are typically formulated by mixing the perturbant with the active agent. The components can be prepared well prior to administration or can be mixed just prior to administration.

The delivery compositions of the present invention may also include one or more enzyme inhibitors. Such enzyme inhibitors include, but are not limited to, compounds such as actinonin or epiactinonin and derivatives thereof.

These compounds have the formulas below:

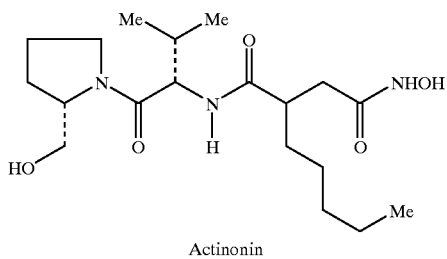

Actinonin LIX

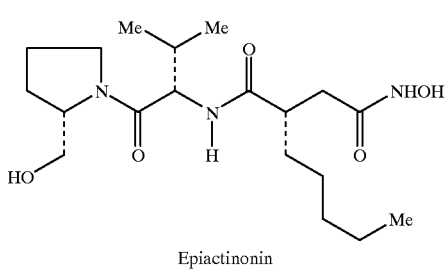

Epiactinonin LX

Derivatives of these compounds are disclosed in U.S. Pat. No. 5,206,384. Actinonin derivatives have the formula:

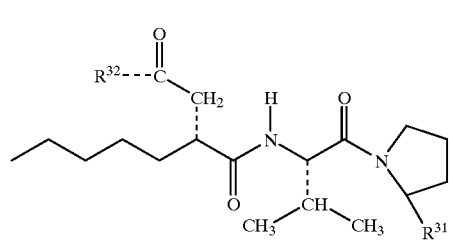

LXI wherein $R^{31}$ is sulfoxymethyl or carboxyl or a substituted carboxy group selected from carboxamide, hydroxyaminocarbonyl and alkoxycarbonyl groups; and $R^{32}$ is hydroxyl, alkoxy, hydroxyamino or sulfoxyamino group. Other enzyme inhibitors include, but are not limited to, aprotinin (Trasylol) and Bowman-Birk inhibitor.

The delivery compositions of the present invention may be formulated into dosage units by the addition of one or more excipient(s), diluent(s), disintegrant(s), lubricant(s), plasticizer(s), colorant(s), or dosing vehicle(s). Preferred dosage unit forms are oral dosage unit forms. Most preferred dosage unit forms include, but are not limited to, tablets, capsules, or liquids. The dosage unit forms can include biologically, pharmacologically, or therapeutically effective amounts of the active agent or can include less than such an amount if multiple dosage unit forms are to be used to administer a total dosage of the active agent. Dosage unit forms are prepared by methods conventional in the art.

The subject invention is useful for administering biologically active agents to any animals such as birds; mammals, such as primates and particularly humans; and insects. The system is particularly advantageous for delivering chemical or biologically active agents which would otherwise be destroyed or rendered less effective by conditions encountered before the active agent in the native state reaches its target zone (i.e. the area to which the active agent to be delivered) and by conditions within the body of the animal to which they are administered. Particularly, the present invention is useful in orally administering active agents, especially those which are not ordinarily orally deliverable.

DESCRIPTION OF THE PREFERRED EMBODIMENTS

The following examples illustrate the invention without limitation. All parts and percentages are by weight unless otherwise indicated.

EXAMPLE 1

α-Interferon Native Gels

Native gradient gels (Pharmacia) were run with 647 μg/ml of α-interferon, (Intron-A—Schering-Plough) and increasing amounts (10–500 mg/mL) of perturbant (mixture of L-Valine, L-Leucine, L-phenylalanine, L-lysine and L-arginine modified with benzenesulfonylchloride) (valine-7.4%, leucine—16.5%, phenylalanine—40.3%, lysine—16.2% and arginine—19.6%). 4 μl of material were loaded onto the gel using a 6/4 comb for loading.

Results are illustrated in FIG. 1.

Lane 1=High molecular weight marker (Bio-Rad)-1:20 dilution w/dH$_2$O–(5 μl–>100 μl).

Lane 2=α-interferon A (647μg/mL) control 5 μl+5 μl Bromophenol Blue (BPB)–(1.29 μg loaded).

Lane 3=α-interferon+perturbant (10 mg/mL)–50 μl α-interferon+50 μl BPB=100 μl (1.29 μg loaded).

Lane 4=α-interferon+perturbant (50 mg/mL) 50 μl α-interferon+50 μl BPB =100 μl (1.29 μg loaded).

Lane 5=α-interferon+perturbant (100 mg/mL ) 50 μl α-interferon+50 μl BPB=100 μl (1.29 μg loaded).

Lane 6=α-interferon+perturbant (500 mg/mL) 5 μl α-interferon+5 μl BPB=10 μl (1.29 μg loaded).

EXAMPLE 1A

α-interferon Native Gradient Gel

The method of Example 1 was followed substituting the thermal condensation product of glutamic acid, aspartic acid, tyrosine, and phenyl-alanine (Glu-Asp-Tye-Phe) that was fractionated through a 3000 molecular weight cut-off filter for the perturbant.

Figure 2:
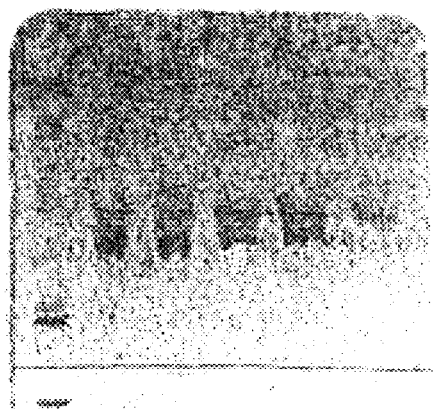

Results are illustrated in FIG. 2.

Samples

Lane 1=High Molecular Weight marker (Bio-Rad).

Lane 2=α-interferon (647 μg/mL)–5 μl+5 μl BPB control.

Lane 3=α-interferon+perturbant (10 mg/mL)–50 μl+50 μl BPB=100 μl.

Lane 4=α-interferon+perturbant–50 μl+50 μl BPB=100 μl.

Lane 5=α-interferon+perturbant (100 mg/mL)–50 μl Intron A+50 μl BPB=100 μl.

Lane 6=α-interferon+perturbant (500 mg/mL)–5 μl Intron A+50 μl BPB=100 μl.

Examples 1 and 1A illustrate that α-interferon alone (lane 2 in FIGS. 1 and 2) banded at the appropriate molecular weight (approximately 19,000 Daltons). As the amount of perturbant added is increased in each subsequent lane relative to a fixed concentration of α-interferon, the α-interferon migrates to a lower, rather than a higher, molecular weight. The change seen with the perturbant of Example 1 is more pronounced than that seen with the perturbant of Example 1 A. This indicates that the α-interferon structure is changing due to the two different perturbants, because if structure were not changing, there would be a shift towards higher molecular weight as perturbant complexes with the active agent.

EXAMPLE 2
Oral Administration of α-interferon and Perturbant to Rats

Male Sprague-Dawley rats (average weight approximately 250 mg) were fasted overnight on wire racks with no bedding. Prior to dosing, animals were anesthetized with a combination ketamine/thorazine subcutaneous. Dosing solutions of the composition prepared according to Example 1 at 500 µg/kg were administered via oral gavage through a 10–12 cm rubber catheter attached to a 1 cc syringe containing the dosing solution. Blood samples were drawn by tail vein bleeding at the designated time points. Serum was prepared and frozen at −70° C. until ready for assay. Serum samples were assayed by ELISA (Biosource International, Camarillo, Calif., Cytoscreen Immunoassay Kit', Catalog #ASY-05 for human IFN-α).

Figure 3:
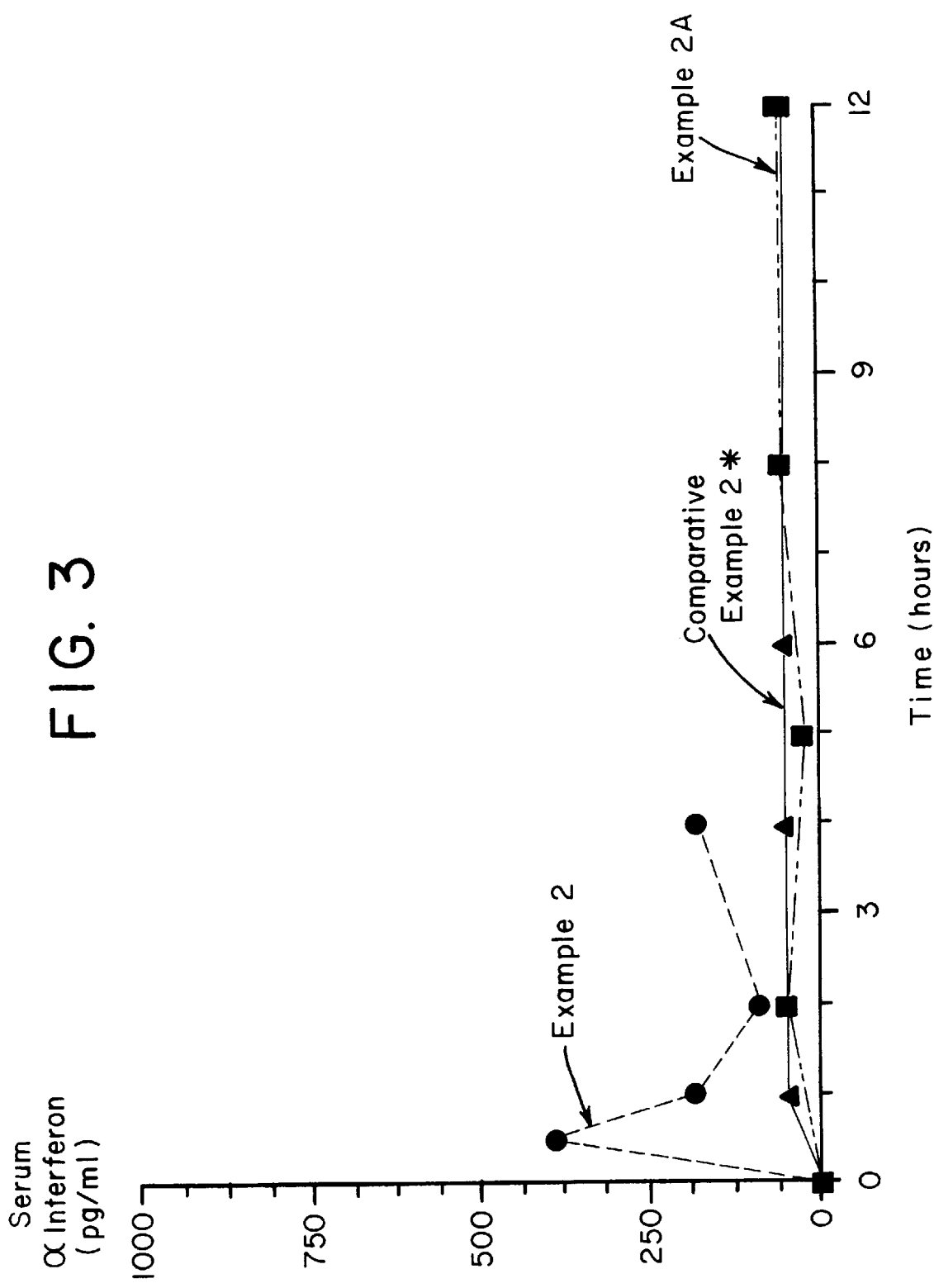

Results are illustrated in FIG. 3.

EXAMPLE 2A
Oral Administration of α-interferon and Perturbant to Rats

The method of Example 2 was followed substituting a dosing solution of the composition prepared according to Example 1 A at 78 µg/kg. Results are illustrated in FIG. 3.

COMPARATIVE EXAMPLE 2*
Oral Administration of α-interferon to Rats

α-interferon at 100 µg/kg without perturbant was administered according to the procedure of Example 2.

Results are illustrated in FIG. 3.

EXAMPLE 3
Oral Administration of Salmon Calcitonin and Perturbant to Rats

The perturbant of Example 1 was reconstituted with distilled water and adjusted to a pH of 7.2–8.0 with HCl or NaOH. Salmon calcitonin (sCt) was dissolved in a citric acid stock solution (0.085 N and then combined with the perturbant solution to obtain the final dosing solution. Final concentrations of perturbant and SCt were 400 mg/mL and 5 µg/mL respectively.

Results are illustrated in Table 1 below.

24 hour fasted male Sprague Dawley rats weighing 100–150 g were anesthetized with ketamine. Rats were administered the dosing solution in a vehicle by oral gavage at 800 mg/kg of perturbant and 10 µg/kg of sCt. The dosing solution was administered using a 10 cm rubber catheter. One hour post-dosing, the rats were administered 1.5 mg/kg thorazine and 44 mg/kg ketamine by intramuscular injection. At 1, 2, 3, and 4 hours post-dosing, blood samples were drawn from the rat tail artery for serum calcium concentration determination using the Sigma Diagnostic Kit (Catalog # 587-A, Sigma Chemical Co, St. Louis, Mo.).

Figure 4:
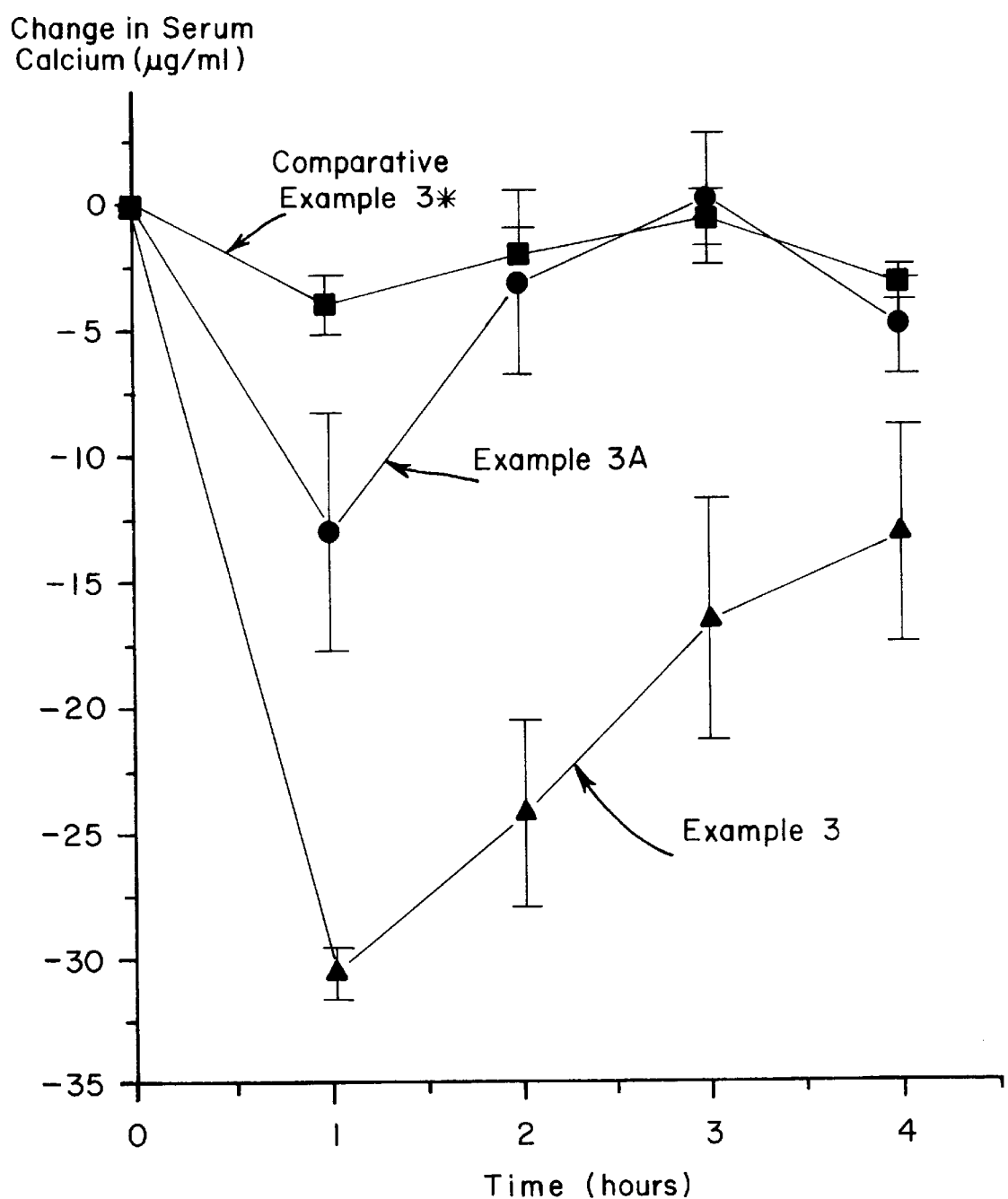

Results are illustrated in FIG. 4.

EXAMPLE 3A
Oral Administration of Salmon Calcitonin and Perturbant to Rats

The method of Example 3 was followed substituting L-tyrosine modified by cyclohexanoyl chloride as the perturbant.

Results are illustrated in FIG. 4.

COMPARATIVE EXAMPLE 3*
Salmon calcitonin (10 µg/kg) without perturbant was administered to rats according to the procedure of Example 3.

Results are illustrated in FIG. 4.

EXAMPLE 4
Isothermal Titration Calometry

A dosing composition of the perturbant of Example 1 at 2.4 mM and sCt at 0.3 mM was prepared, and isothermal titration calorimetry was performed at pH 6.5 and 4.5. The buffer at pH 6.5 was 30 mM Hepes-30 mM NaCl, and the buffer at pH 4.5, was 30 mM sodium acetate-30 mM NaCl.

All experiments were performed at 30° C. using 8.0 mM perturbant in the dropping syringe and 1.0 mM calcitonin in the calorimeter cell. In all experiments, 15×10 µl increments of perturbant were added in 10 second duration additions with 2 minutes equilibration between additions.

Results were validated in experiments where perturbant (8 mM) was placed in the dropping syringe, and equivalent increments were added to pH 4.5 buffer (no sCt) and where perturbant was placed in the dropping syringe and 10 µl increments were added to pH 6.5 buffer (no sCt). Titration curves were not obtained in these experiments, and the results showed that heat of mixing and/or dilution of perturbant is negligible. Therefore, the experimental isotherms were not corrected by background subtraction.

Results are illustrated in Table 1 below.

EXAMPLE 4A
The method of Example 4 was followed substituting the perturbant of Example 1A. Results were validated in experiments where perturbant was placed in the dropping syringe, and equivalent increments were added to pH 4.5 buffer (no sCt).

Results are illustrated in Table 1 below.

TABLE 1

| Binding Parameters of Perturbants as Determined by ITC[1] | | | | |
|---|---|---|---|---|
| | $K_D$ (M) | ΔH (cal/mol) | ΔS (cal/mol ° K.) | N |
| pH 6.6 | | | | |
| Example 4 | $4.59 \times 10^{-8}$ | +240 | +34.4 | 0.6 |
| Example 4A | $6.99 \times 10^{-9}$ | +277 | +38.3 | 11.6 |
| pH 4.5 | | | | |
| Example 4 | Precipitates | | | |
| Example 4A | $1.29 \times 10^{-4}$ | +553 | +19.8 | +0.8 |

[1]Calorimetry experiments were performed essentially as detailed by You, J. L., Scarsdale, J. N., and Harris, R. B., J. Prot. Chem. 10: 301–311, 1991; You, Junling, Page, Jimmy D., Scarsdale, J. Neel, Colman, Robert W., and Harris, R. B., Peptides 14: 867–876, 1993; Tyler-Cross, R., Sobel, M., Soler, D. F., and Harris, R. B., Arch. Biochem. Biophys. 306: 528–533, 1993; Tyler-Cross, R., Sobel, M., Marques, D., and Harris, R. B., Protein Science 3: 620–627, 1994.

EXAMPLE 5
GuHCl Denaturation Of α-Interferon

A stock solution of 9.1 mg/mL of α-interferon (Schering Plough Corp.) in 20 mM sodium phosphate buffer at pH 7.2 was prepared. Samples were prepared by diluting the α-interferon with the sodium phosphate buffer and 10 M guanidine hydrochloride (GuHCl) (Sigma Chemical Co.— St. Louis, Mo.) stock solution to 200 ug/mL concentration of α-interferon at various concentrations of GuHCl. Diluted samples were allowed to come to equilibrium by incubation for approximately 30 minutes at room temperature prior to measurement.

Fluorescence measurements were made at 25° C. using a Hitachi F-4500. Protein tryptophan fluorescence was observed at an excitation wavelength of 298 nm and an emission wavelength of 343 nm. ANS (1-anilinonapthalene-8- sulfonate) fluorescence was observed at an excitation wavelength of 355 nm and an emission wavelength of 530 nm. For all fluorescence measurements, a 5 nm spectral bandpass was chosen for both excitation and emission.

Figure 5:
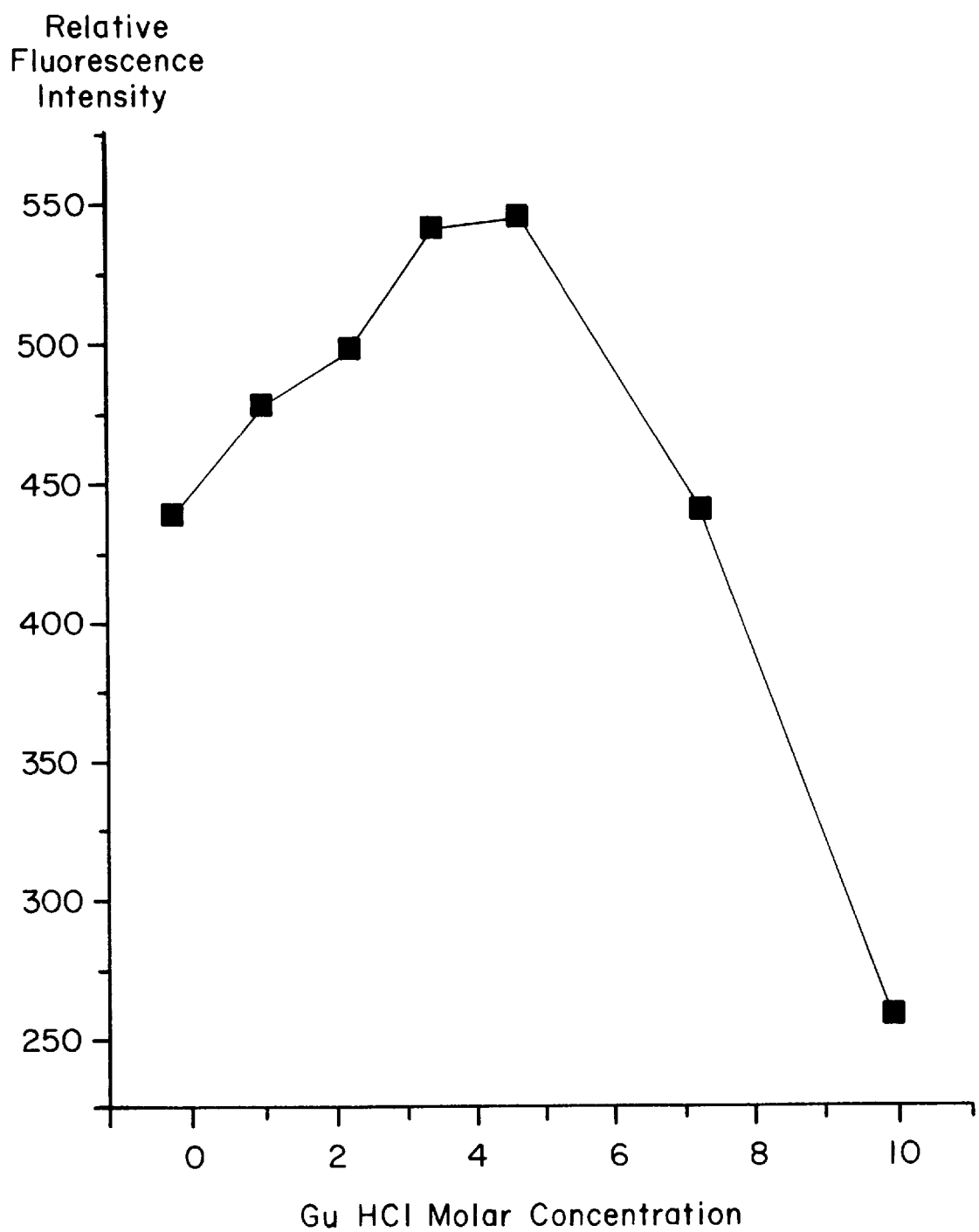

Results are illustrated in FIG. 5.

EXAMPLE 6
Concentration Effect of GuHCl on α-Interferon Configuration

GuHCl 5 M stock solution was prepared using 20 mM sodium phosphate, pH 7.2 buffer. After dilution, the pH of the stock was checked and adjusted by concentrated HCl. To determine the concentration of final solution the refractive index referenced in *Methods in Enzymology,* Vol. 6, page 43 by Yasuhiko Nozalki was used.

α-interferon stock (9.1 mg/mL) was mixed with sufficient amounts of GuHCl to yield the concentrations of Table 1A below:

TABLE 1A

α-Interferon/GuHCl Solutions

| GuHCl (M) | α-IFN (mg/mL) |
|---|---|
| 0.5 | 0.60 |
| 1.0 | 0.53 |
| 1.5 | 0.60 |
| 2.0 | 0.50 |
| 3.0 | 0.60 |
| 4.0 | 0.50 |

Figure 6:
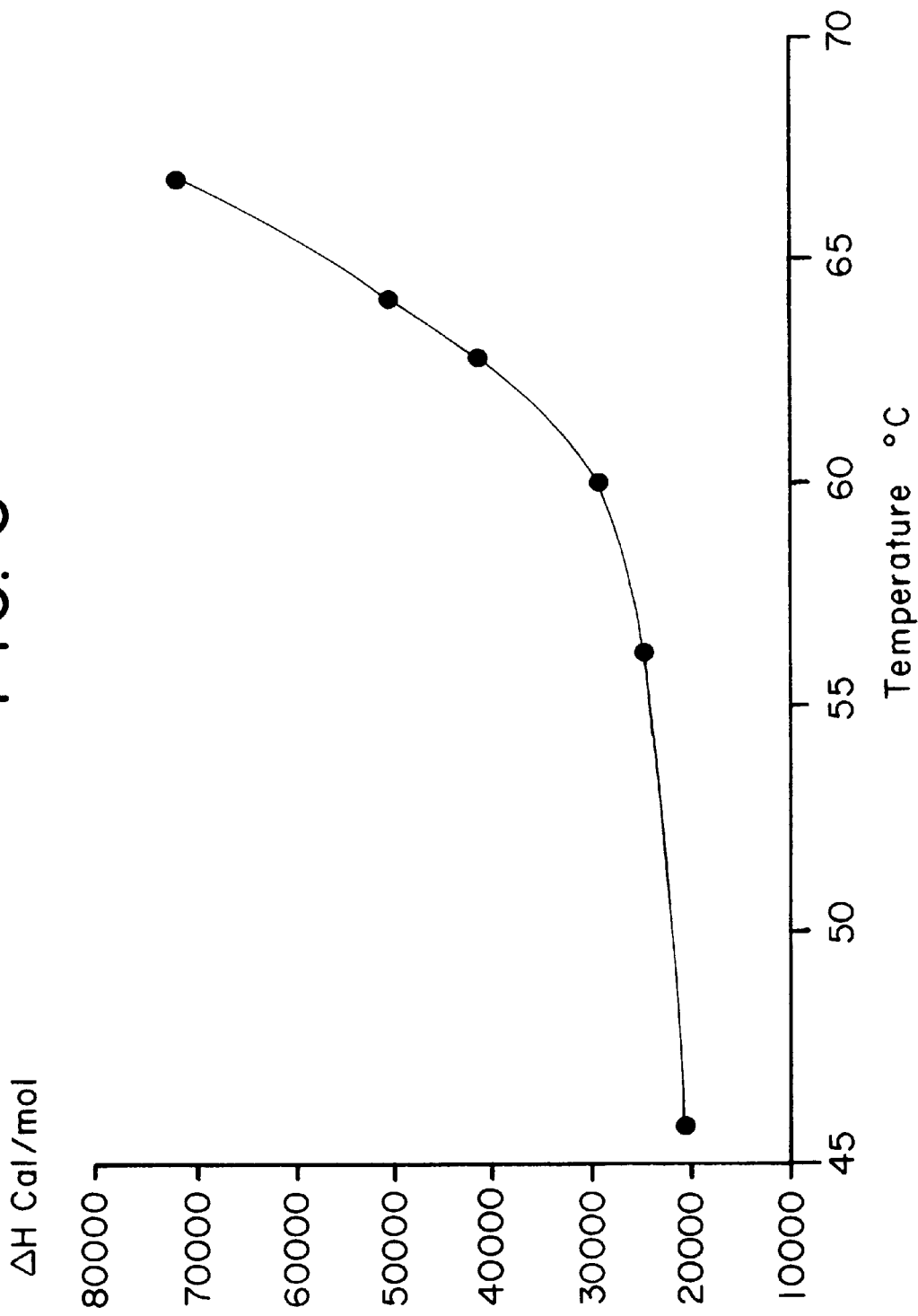

Differential scanning calorimetry (DSC) was run, and results are illustrated in FIG. 6.

EXAMPLE 7
pH Titration of Intron A as Measured by Intrinsic Tryptophan Fluorescence A stock solution of 9.1 mg/mL α-interferon in 20 mM sodium phosphate buffer at pH 7.2 (Schering Plough Corp.) was prepared. Samples were prepared by diluting the α-interferon to a concentration of 200 ug/mL into solution buffered at various pH values using the following buffers: Glycine at pH 2 and 12, sodium phosphate at pH 3, 4, 5, 7, and boric acid at pH 8. These buffers were prepared as described in the Practical Handbook of Biochemistry and Molecular Biology, Edited by Gerald D. Fasman, 1990. Diluted samples were allowed to come to equilibrium by incubation for approximately 30 minutes at room temperature prior to measurement.

Figure 7:
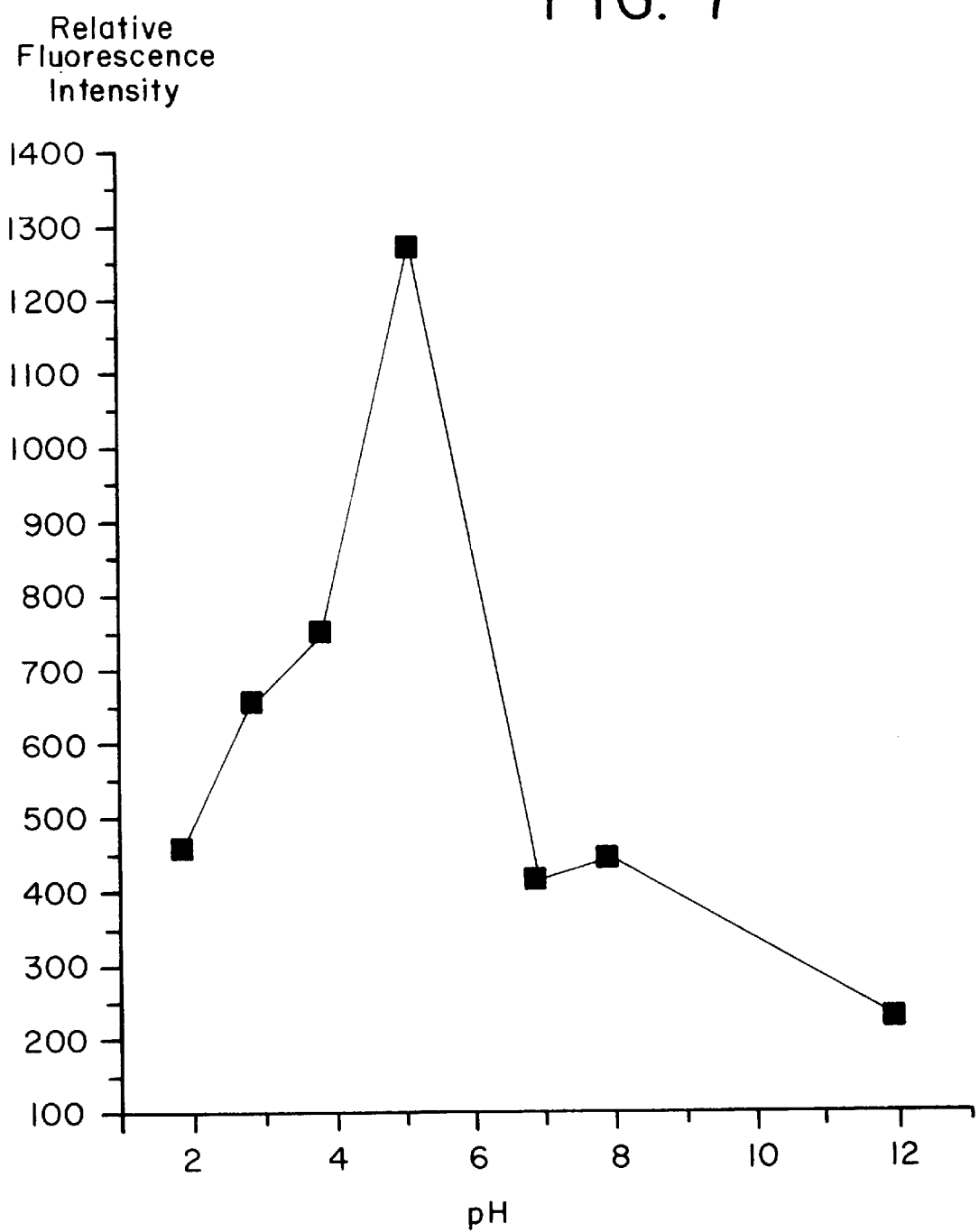

Fluorescence was measured according to the procedure of Example 5. Results are illustrated in FIG. 7.

EXAMPLE 8
ph Titration of Insulin Measured by ANS Fluorescence

A stock solution was prepared by dissolving 2 mg of insulin in 1 mL of deionized water. 1-anilinonaphthalene-8-sulphonate (ANS) stock solution was prepared by dissolving 10 mg in 10 mL of deionized water. Samples were prepared by diluting the insulin to a concentration of 200 ug/mL into solution buffered at various pH values using the following buffers: Glycine at pH 2 and 12, sodium phosphate at pH 3, 4, 5, 7, and boric acid at pH 8. These buffers were prepared as described in the Practical Handbook of Biochemistry and Molecular Biology, Edited by Gerald D. Fasman, 1990. The final ANS concentration was 90 ug/mL. Diluted samples were allowed to come to equilibrium by incubation for approx. 30 minutes at room temperature prior to measurement.

Figure 8:
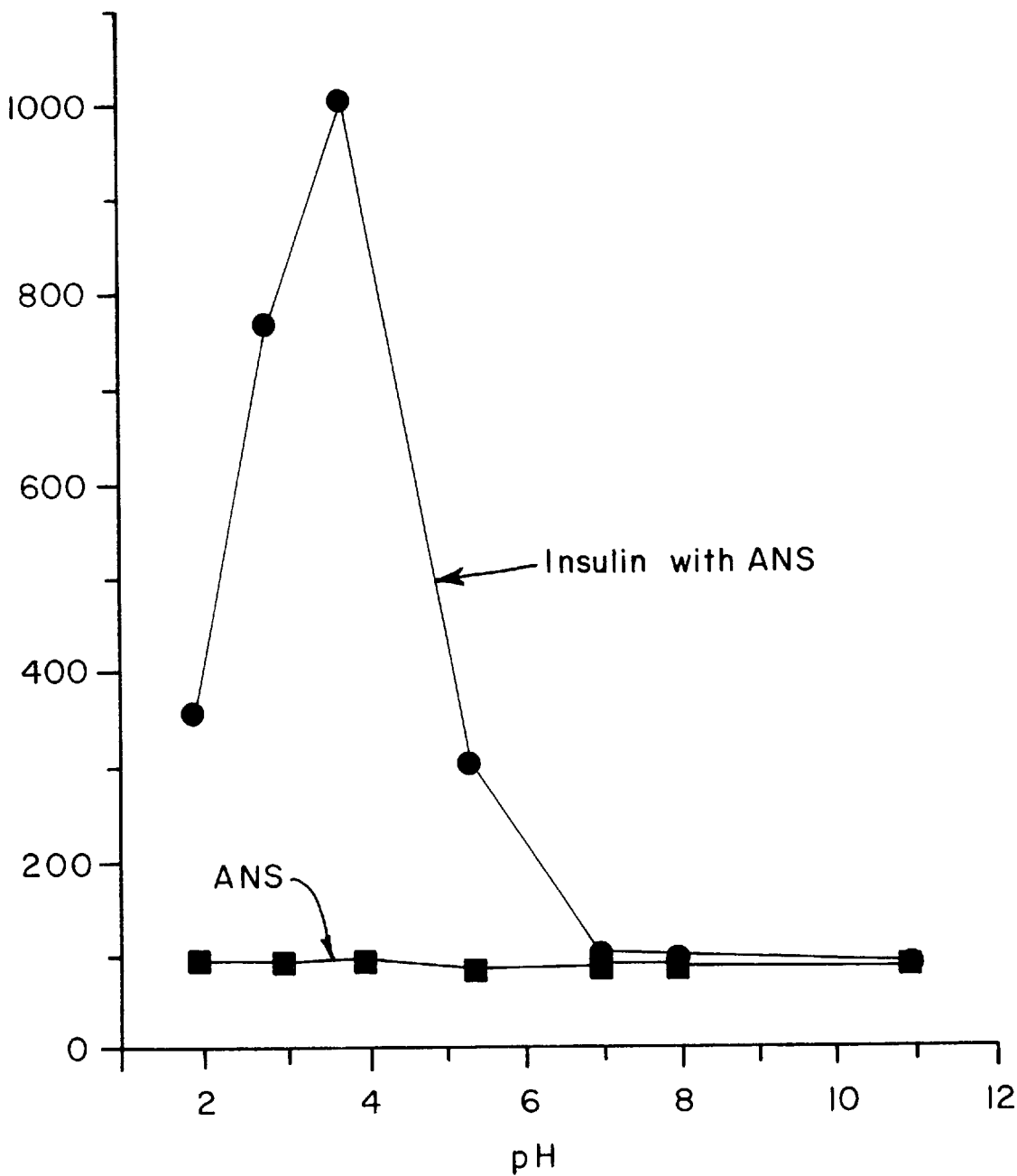

Fluorescence was measured according to the procedure of Example 5. Results are illustrated in FIG. 8.

EXAMPLE 9
Reversibility of Circular Dichroism Spectra of α-interferon at pH 2 and 7.2

Circular dichroism spectra of α-interferon were generated at pH 7.2. The pH of the solution was then readjusted to pH 2, and the sample was rescanned. The sample solution was then readjusted to 7.2 and rescanned.

Concentration of α-interferon was 9.2 $\mu$M or 0.17848 mg/mL, ([IFN] stock=9.1 mg/mL). Buffers used were 20 mM NaPhosphate at pH 7.2; and 20 mM Glycine at pH 2.0.

Reversal of the pH to 7.2 resulted in complete restoration of the native structure, demonstrating the reversibility of the intermediate state. It is believed that the free energy difference between the native state and the intermediate state is small.

Figure 9B:
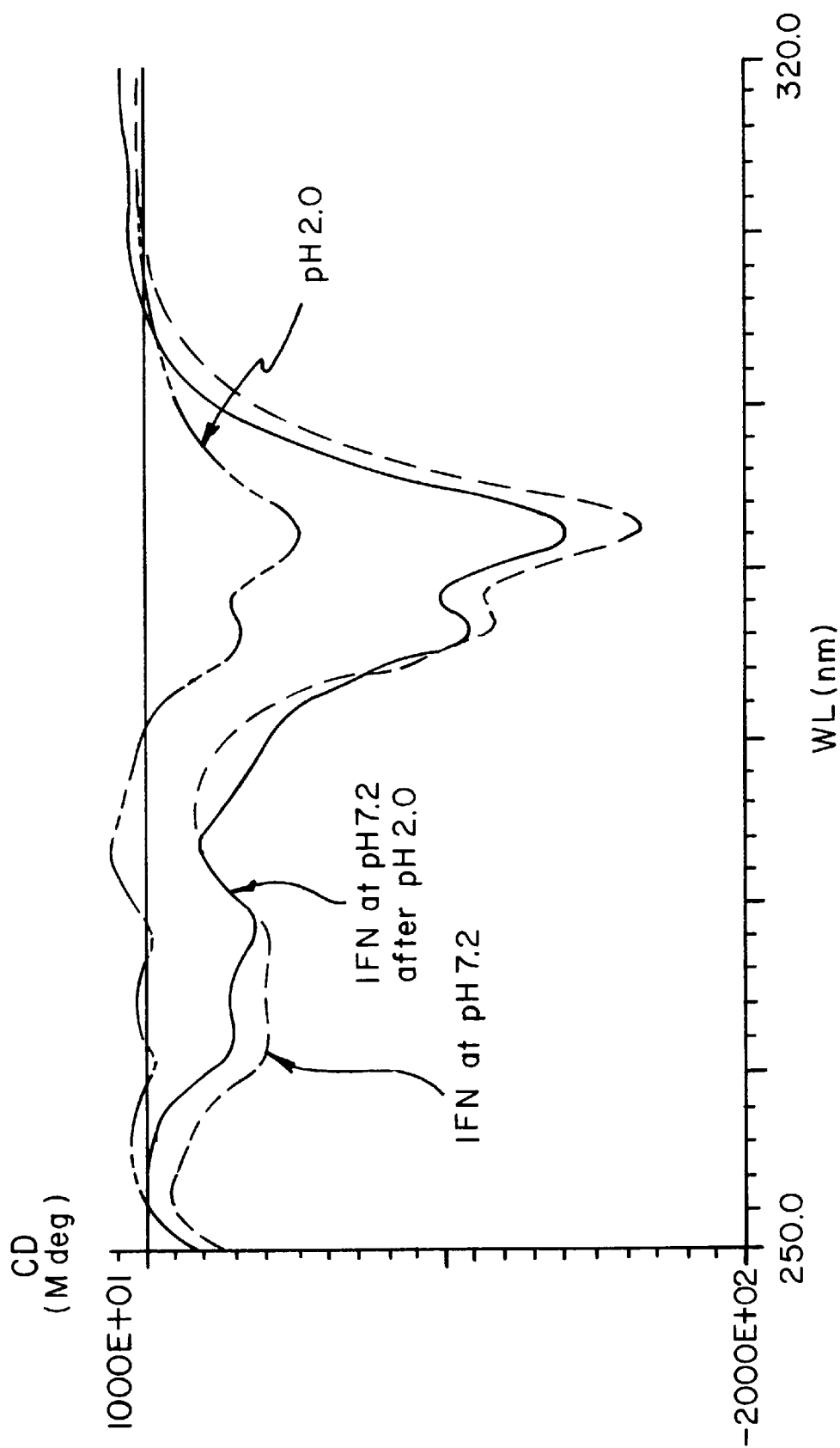

Results are illustrated in FIGS. 9A and 9B.

EXAMPLE 10
Circular Dichroism Spectra of α-interferon at 7.2—pH Dependence

The extent of ordered secondary structure of α-interferon at different pH's was determined by circular dichroism (CD) measurements in the far UV range. The large dilution factor of interferon stock (~50 times) resulted in the sample being at the proper pH. Concentration of α-interferon was 9.2 $\mu$M or 0.17848 mg/mL, ([IFN] stock=9.1 mg/mL). Buffers used were 20 mM sodium phosphate at pH 6.0 and 7.2; 20 mM NaAc at pH 3.0, 4.0, 4.5, 5.0 and 5.5; and 20 mM Glycine at pH 2.0

The secondary structure content was estimated with several fitting programs, each of which decomposes the CD curve into four major structural components: α-helix, β-sheet, turns, and random coil. Two of those programs were provided with the CD instrument as an analysis facility. The first program uses seven reference proteins: Myoglobin, Lysozyme, Papain, Cytochrome C, Hemoglobin, Ribonuclease A and Chymotrypsin. The second uses Yang.REF reference file.

A third program, CCAFAST, uses the Convex Constraint Algorithm and is described in "Analysis of Circular Dichroism Spectrum of Proteins Using the Convex Constraint Algorithm: A Practical Guide". (A. Perczel, K. Park and G. D. Fasman (1992) *Anal. Biochem.* 203: 83–93).

Deconvolution of the far UV scans over a range of pH volumes (2.0–7.2) indicates significant compaction of the secondary structure at pH 3.5. The near UV scan indicates a disruption of tertiary structure packing, and the far UV scan indicates that there is still significant secondary structure at this pH.

Figure 10:
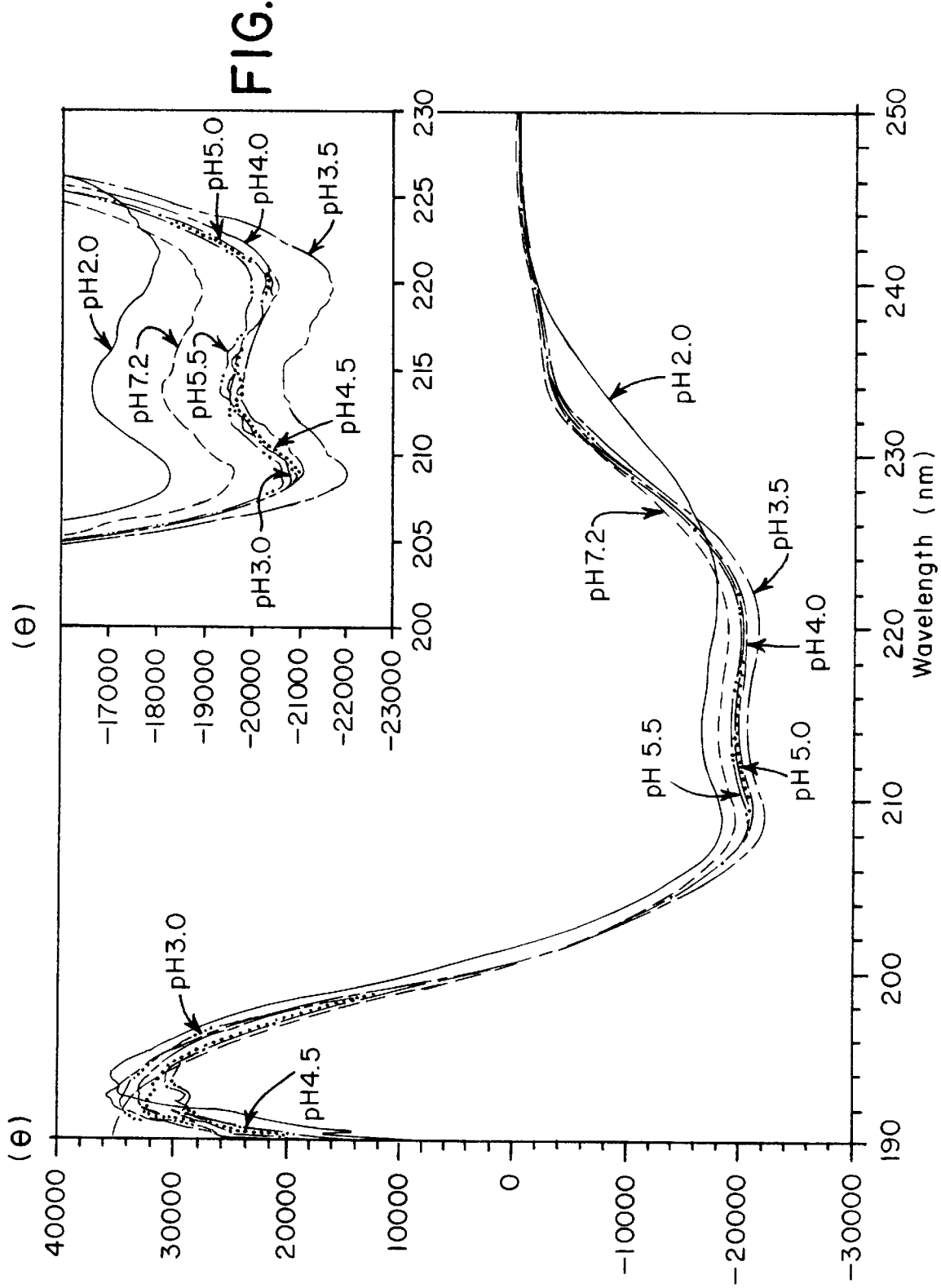

Results are illustrated in FIG. 10.

EXAMPLE 11

DSC of Insulin and Increasing Concentrations of GuHCl

DSC was performed with 6 mg/mL insulin (0.83 mM assuming a molecular weight of 6,000) in 50 mM phosphate buffer, pH 7.5. Each subsequent thermogram was corrected by background subtraction of a 0.6M guanidine-phosphate buffer solution.

Insulin was freshly prepared as a concentrated stock solution in 50 mM phosphate buffer, pH 7.5, and an appropriate aliquot was diluted in buffer, filtered though a 2 micron PTFE filter, and degassed for at least 20 minutes. The reference cell contained degassed buffer.

Scanning calorimetry was performed using 5 mg 0.83 mM porcine insulin (MW 6,000) per mL in 50 mM phosphate buffer, pH 7.5. All thermograms were performed on a Microcal MC-2 scanning calorimeter equipped with the DA2 data acquisition system operated in the upscale mode at 1° C./min (up to 90° C.), and data points were collected at 20 second intervals. All scans were initiated at least degrees below the observed transitions for the active agent. All thermograms were corrected for baseline subtraction and normalized for the concentration of macromolecule. According to the methods of the Johns Hopkins Biocalorimetry Center, See, for example, Ramsay et al. *Biochemistry* (1990) 29:8677–8693; Schon et al. *Biochemistry* (1989) 28:5019–5024 (1990) 29: 781–788. The DSC data analysis software is based on the statistical mechanical deconvolution of a thermally induced macromolecular melting profile.

The effect of GuHCl on structure was assessed in DSC experiments where individual solutions were prepared in phosphate buffer, pH 7.5, containing denaturant diluted from a 5M stock solution to concentrations ranging for 0.5–2M.

Results are illustrated in Table 2 below.

TABLE 2

DSC of Insulin and Increasing Concentrations of Guanidine Hydrochloride

| | Tm (Cp, max) (° C.) |
|---|---|
| Insulin   0.0M GuHCl | 78.3 |
| Insulin + 0.5M GuHCl | 79.3 |
| Insulin + 1.0M GuHCl | 77.5 |
| Insulin + 2.0M GuHCl | 69.7 |
| Insulin + 3.0M GuHCl | no transition observed |

EXAMPLE 12

Effect of Ionic Strength on the DSC Spectrum of Insulin

A sample containing 6 mg/mL insulin (0.83 mM in 50 mM phosphate buffer, pH 7.5, containing 0.25, 0.5, or 1.0M NaCl) was used. Thermograms were performed according to the procedure in Example 11 and were corrected by subtraction of a 0.5M NaCl-phosphate buffer blank as described above.

The effect of increasing ionic strength on structure was assessed in DSC experiments where individual solutions were prepared so as to contain NaCl at concentrations ranging from 0.25–3M.

Results are illustrated in Table 3 below.

TABLE 3

Effect of Ionic Strength on the DSC Spectrum of Insulin

| | Tm (Cp, max) (° C.) |
|---|---|
| Insulin   0.0M NaCl | 78.3 |
| Insulin + 0.25M NaCl | 80.7 |
| Insulin + 0.5M NaCl | 80.7 |
| Insulin + 1.0M NaCl | 80.7 |

EXAMPLE 12A

Effect of Ionic Strength on the DSC Spectrum of rhGh

The method of Example 11 was followed substituting 5 mg/mL recombinant human growth hormone (rhGh) (225 µM based on M, 22,128 of HGH) in 50 mM phosphate buffer, pH 7.5 containing either 0.5 or 1.0M NaCl, for the insulin. The thermograms were corrected by subtraction of a 0.5M NaCl-phosphate buffer blank.

Results are illustrated in Table 4 below.

TABLE 4

Effect of Ionic Strength on the DSC Spectrum of rhGh

| | | Tm (Cp, max) (° C.) | ΔH° (kcal/mol) |
|---|---|---|---|
| rhGh |   0.0M NaCl | 75.2 | 191.0 |
| rhGh + |   0.5M NaCl | 75.8 | 89.7 |
| rhGh + | 10.0M NaCl | 76.5 | 50.5 |

EXAMPLE 13

Effect of pH on the DSC Spectrum of rhGH 5 mg/mL rhGh were dissolved in buffer (0.17 mM in 50 mM phosphate buffer, assuming a molecular weight of 20,000). The pH of the solution was adjusted to the desired value, and all curves were corrected by baseline subtraction. The effect of pH on structure was assessed by DSC according to the procedure of Example 11 where individual solutions were prepared in phosphate buffer ranging in pH value from 2.0 to 6.0.

Results are illustrated in Table 5 below.

TABLE 5

Effect of pH on the DSC Spectrum of rhGh

| | Tm (Cp, max) (° C.) | ΔH° (kcal/mol) |
|---|---|---|
| pH 2.0 | no transition observed | no transition observed |
| pH 3.0 | no transition observed | no transition observed |
| pH 3.5 | no transition observed | no transition observed |
| pH 4.0 | ≈73.0 | broad transition |
| pH 5.0 | 75.0 | 161 |
| pH 6.0 | 75.2 | 191 |
| pH 7.5 (10 mg/mL) | a) 73<br>b) 75 | (a) + (b) = 632 |

EXAMPLE 14

Effect of GuHCl on the DSC Spectrum of rhGh

An initial scan of rhGh was performed at 10 mg/mL in the absence of GuHCl (0.33 mM assuming 20,000 molecular weight). Subsequently, the concentration of rhGh was lowered to 5 mg/mL (0.17 mM) in 50 mM phosphate buffer, pH 7.5 containing varying concentrations of GuHCl. Each subsequent thermogram was corrected by background subtraction of a 0.5M guanidine-phosphate buffer solution. The thermograms were corrected by subtraction of a 0.5M NaCl-phosphate buffer blank. Scans were performed according to the procedure of Example 11.

Results are illustrated in Table 6 below.

TABLE 6

Effect of Guanidine Hydrochloride on DSC Spectrum of rhGh

|   | DOMAIN A Tm (Cp,max) (° C.) | DOMAIN B Tm (Cp,max) (° C.) | ΔH° (kcal/mol) |
| --- | --- | --- | --- |
| rhGh | 72.6 | 74.3 | 632 |
| rhGh + 0.5M GuHCl | 71.5 | not defined, but present | 48 |
| rhGh + 1.0M GuHCl | 70.9 | absent | 109 |
| rhGh + 1.5M GuHCl | 69.7 | absent | 12 |
| rhGh + 2.0M GuHCl | 70.0 | absent | 58 |
| rhGh + 2.5M GuHCl | 70.7 | absent | 99 |

EXAMPLE 15
pH Dependence of α-Interferon Conformation

α-interferon stock (9.1 mg/mL) was diluted with buffer to a concentration of 0.6 mg/mL. The sample was dialyzed overnight in buffer (volume ratio of α-interferon to buffer was 1:4000). Since there was no extinction coefficient provided, concentration of the sample used was determined by comparison of absorption spectra of the sample before and after dialysis. For each particular pH, the absorbance of the nondialyzed α-interferon of known concentration was measured at 280 nm. Then after dialysis, absorbance was read again to account for the protein loss, dilution, etc. Buffer conditions and α-interferon concentrations were:

| pH 3.0: Buffer - 20 mM NaAc. | [IFN] = 0.50 mg/mL; |
| --- | --- |
| pH 4.1: Buffer - 20 mM NaAc. | [IFN] = 0.53 mg/mL; |
| pH 5.0: Buffer - 20 mM NaAc. | [IFN] = 0.37 mg/mL; |
| pH 6.0: Buffer - 20 mM Na Phosphate. | [IFN] = 0.37 mg/mL; |
| pH 7.2: Buffer - 20 mM Na Phosphate. | [IFN] = 0.48 mg/mL. |

DSC scans were performed according to the procedure of Example 11. Although clear, transparent solutions of α-interferon were obtained for every pH at room temperature, there were noticeable signs of precipitation at pH 5.0 and 6.0 after the temperature scans.

Results are illustrated in Table 7 below.

TABLE 7

α-Interferon - pH dependence DSC

| pH | Tm ° C. | ΔH cal/mol |
| --- | --- | --- |
| 7.2 | 66.84 | 732717 |
| 6.0 | 65.34 | 45580 |
| 5.0 | 67.32 | 69782 |
| 4.1 | 65.64 | 60470 |
| 3.0 | — | — |

EXAMPLE 16
Concentration Effect of GuHCl on α-interferon Conformation

GuHCL/α-interferon samples were prepared according to the method of Example 6. DSC scans were performed according to the procedure of Example 11.

Results are illustrated in Table 8 below.

TABLE 8

α-Interferon in GuHCl DSC

| [GuHCl] M | Tm ° C. | ΔH cal/mol |
| --- | --- | --- |
| 0.0 | 67.12 | 72562 |
| 0.5 | 64.43 | 50827 |
| 1.0 | 63.04 | 41705 |
| 1.5 | 60.11 | 29520 |
| 2.0 | 56.32 | 24980 |
| 3.0 | 45.90 | 20577 |
| 4.0 | — | — |

Examples 5–16 illustrate that ionic strength, guanidine hydrochloride concentration, and pH result in changes in the Tm of active agents, indicating a change in conformation. This was confirmed by fluorescence spectroscopy. The reversible intermediate conformational states can be used as templates to prepare mimetics.

EXAMPLE 17
Preparation of α-Interferon Intermediate State Mimetics

An intermediate conformational state of α-interferon is determined. A peptide mimetic having the secondary and tertiary structure of the intermediate state is prepared.

EXAMPLE 18
Preparation of Insulin Intermediate State Mimetics

The method of Example 17 is followed substituting an insulin for the α-interferon.

EXAMPLE 19
Preparation of rhGh Intermediate State Mimetics

The method of Example 17 is followed substituting recombinant human growth hormone for the α-interferon.

EXAMPLE 20
In vivo Administration of α-Interferon Mimetics

Rats are dosed according to the procedure of Example 2 with the mimetic prepared according to the procedure of Example 17.

EXAMPLE 21
In vivo Administration of Insulin Mimetics

The procedure of Example 20 was followed, substituting the mimetic prepared according to the procedure of Example 18.

EXAMPLE 22
In vivo Administration of rhGH Mimetics

The procedure of example 19 was followed, substituting the mimetic prepared according to the procedure of Example 19.

EXAMPLE 24
Titration of α-Interferon as Measured by Intrinsic Tryptophan Fluorescence A stock solution of 9.1 mg/mL α-interferon in 20 mM sodium phosphate buffer at pH 7.2 was prepared. A stock solution of perturbant was prepared by dissolving 800 mg of perturbant (L-arginine acylated with cyclohexanoyl chloride) in 2 mL of 20 mM Sodium Phosphate buffer (pH7).

Samples were prepared by diluting the α-interferon with the sodium phosphate buffer and perturbant stock solution at various perturbant concentrations. Diluted samples were allowed to come to equilibrium by incubation for approximately 30 minutes at room temperature prior to measurement.

Fluorescence from the endogenous tryptophan resident of α-interferon were measured according to the procedure of Example 5. The perturbant did not contain a fluoophore.

Figure 11:
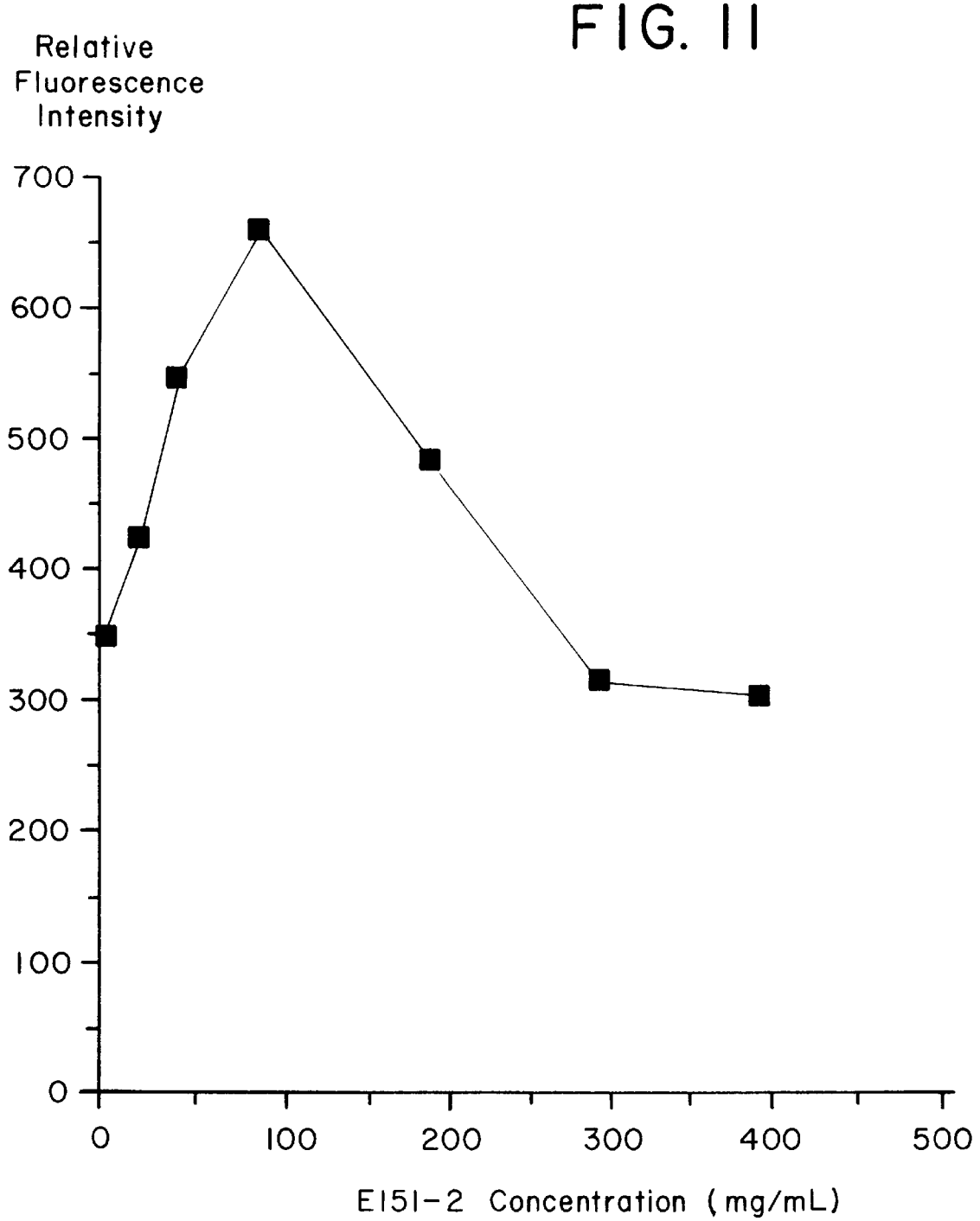

Results are illustrated in FIG. 11.

EXAMPLE 25
In vivo Administration of Perturbant and α Interferon to Rats

Rats were dosed according to the method of Example 2 with dosing solutions containing the perturbant of Example 24 (800 mg/kg) mixed with α-interferon (1 mg/kg). Serum samples were collected and assayed by ELISA according to the procedure of Example 2.

Figure 12:
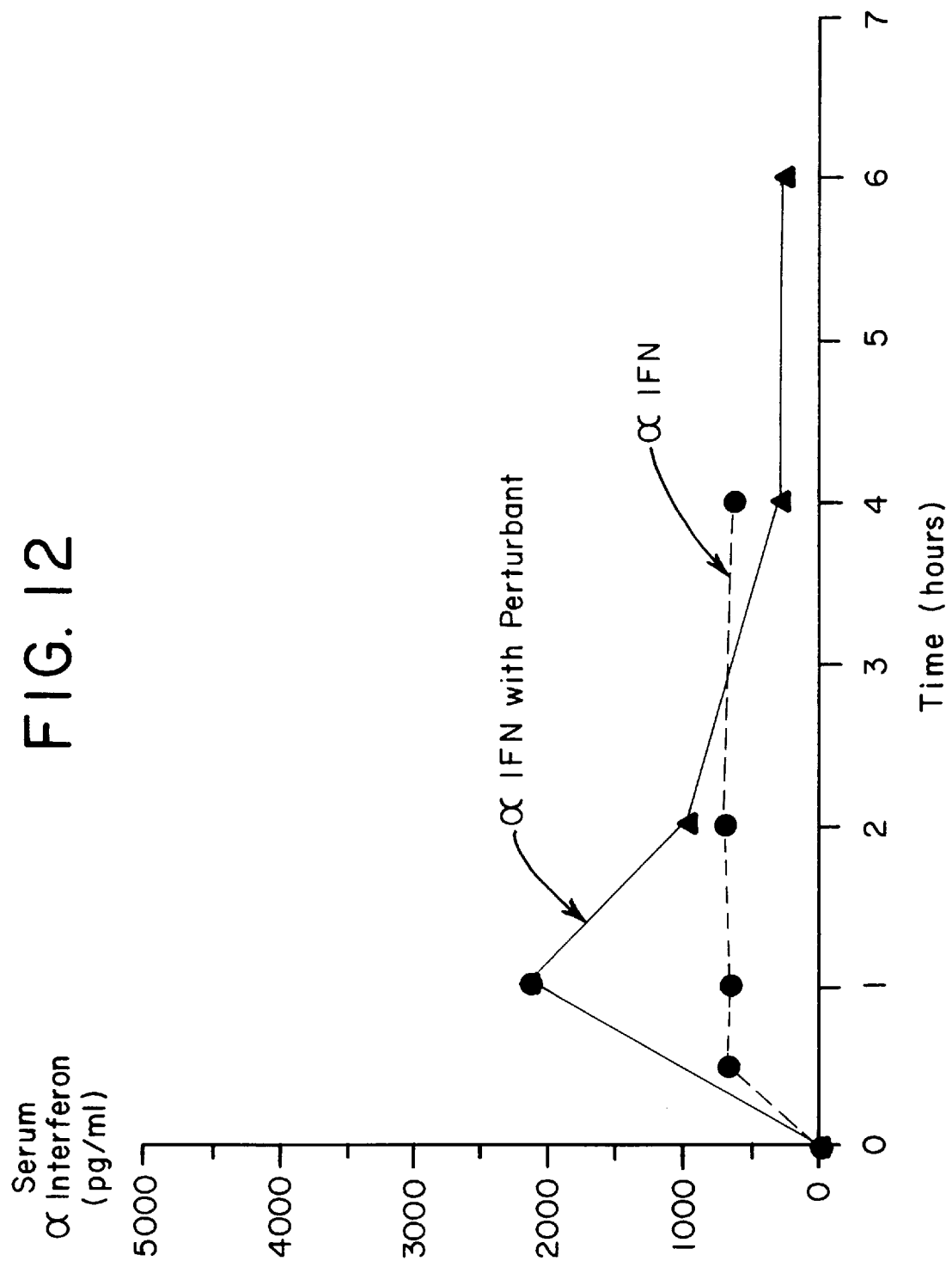
Figure 13:
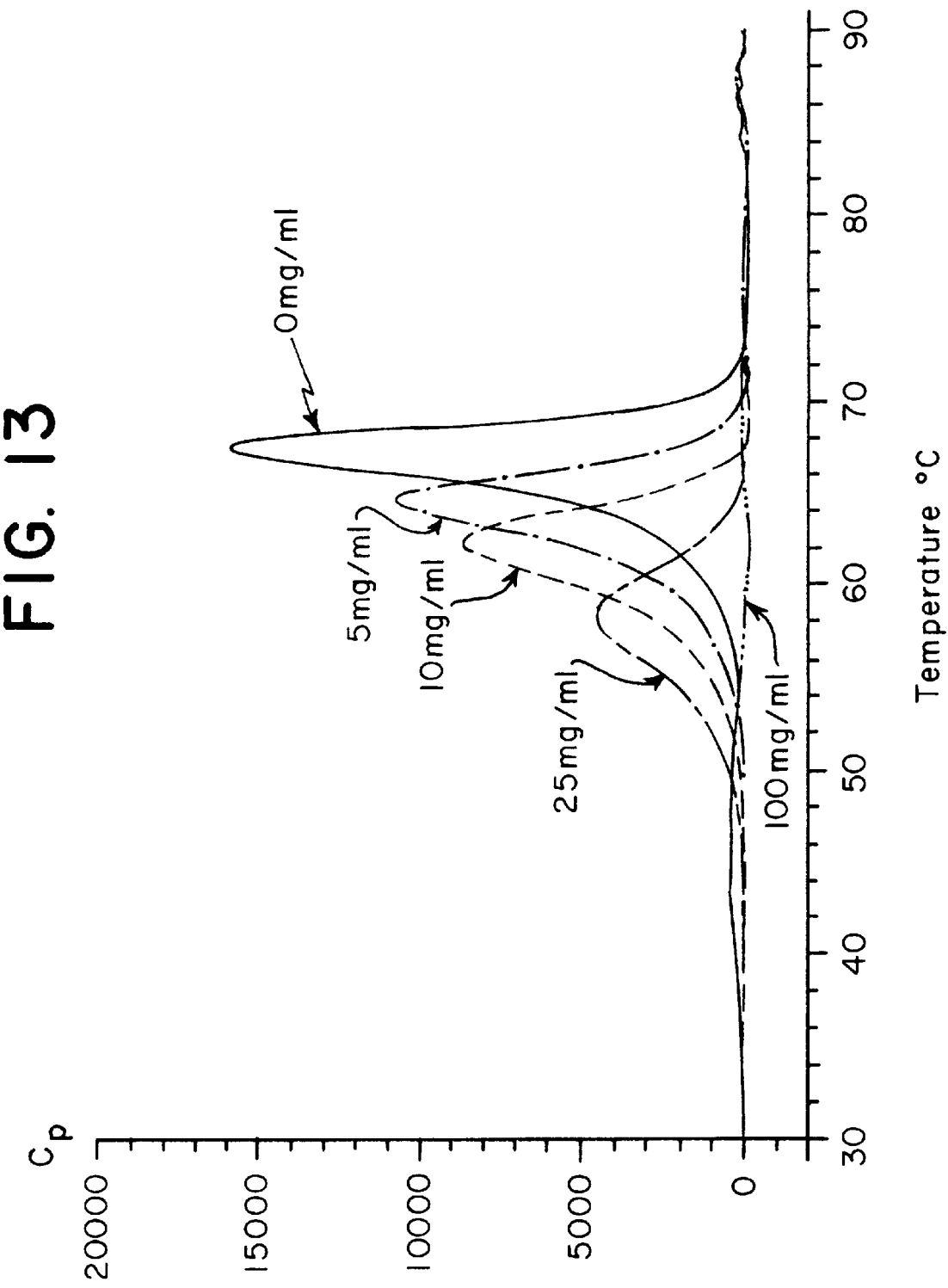

Results are illustrated in FIG. 12.

COMPARATIVE EXAMPLE 25*

Rats were dosed according to the method of Example 25 with α-interferon (1 mg/kg). Serum samples were collected and assayed according to the procedures of Example 25.

Results are illustrated in FIG. 12.

EXAMPLE 26
Differential Scanning Colorimetry of α-Interferon and Perturbant

Perturbant binding DSC was conducted using 20 mM NaPhosphate buffer at pH 7.2. Dry perturbant was weighed out to make perturbant stock solutions. α-interferon stock was diluted in the buffer. α-interferon solution was not dialyzed prior to experiments for the purpose of having the same active concentration for the whole set.

DSC thermograms were generated with α-interferon at a concentration of 0.64 mg/ml and a perturbant (phenylsulfonyl-para-aminobenzoic acid purified to >98% (as determined by reverse phase chromatography prior to generation of the spectra)) at perturbant concentrations of 5, 10, 25 and 100 mg/ml. DSC was conducted on a DASM-4 differential scanning calorimeter interfaced to an IBM PC for automatic collection of the data. The scanning rate was 60° C./h.

Results are illustrated in Table 9 below and Example 13.

COMPARATIVE EXAMPLE 26*
Different Scanning Calorimetry of α-Interferon

The method of Example 26 was followed substituting α-interferon without perturbant. Results are illustrated in Table 9 below and Example 13.

TABLE 9

| α-Interferon + Perturbant DSC | | |
| --- | --- | --- |
| Perturbant - mg/ml | Tm ° C. | ΔH cal/mol |
| 0 | 67.12 | 72562 |
| 5 | 64.37 | 60151 |
| 10 | 62.3 | 53161 |
| 25 | 58.15 | 35393 |
| 100 | 46.18 | 5439.3 |

DSC scans where the added concentration of perturbant ranged from 0–100 mg/mL show induced conformational changes in the α-interferon that occur in a concentration dependent manner. At 100 mg/mL of the perturbant, the thermogram indicated that the α-interferon Cp vs. Tm curve was a flat line. The flat Cp vs. Tm curve obtained at 100 mg/mL of perturbant indicates that hydrophobic residues within the α-interferon molecule became solvent exposed. It is clear that the perturbant was able to change the structure of α-interferon in a concentration dependent manner.

EXAMPLE 27
Dialysis Experiments—Reversibility of Complexing with the Perturbant An α-interferon stock solution at a concentration of 9.1 mg/mL was diluted with buffer to an α-interferon concentration of 0.6 mg/mL. DSC was performed according to the procedure of Example 26.

Figure 14A:
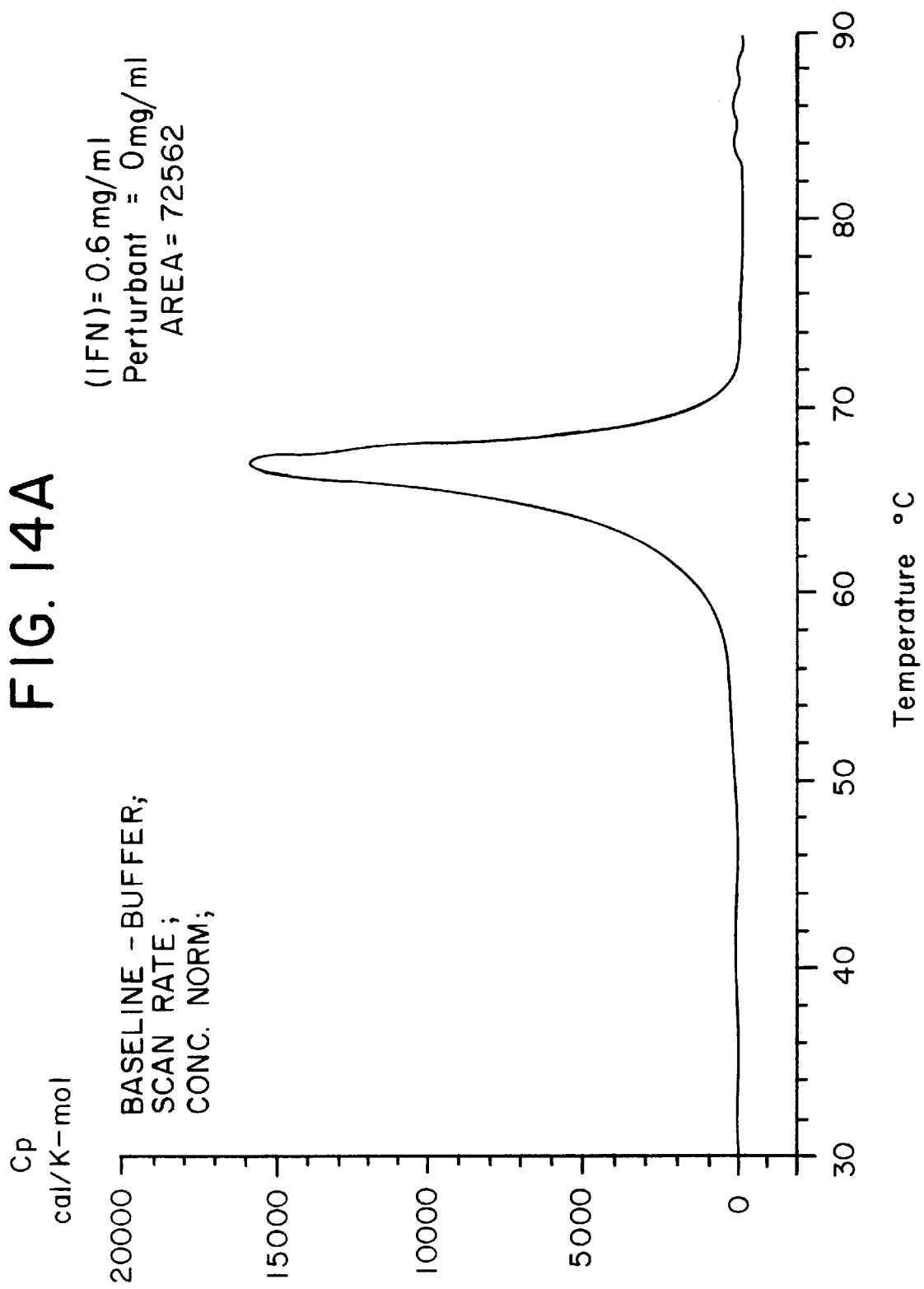
Figure 14B:
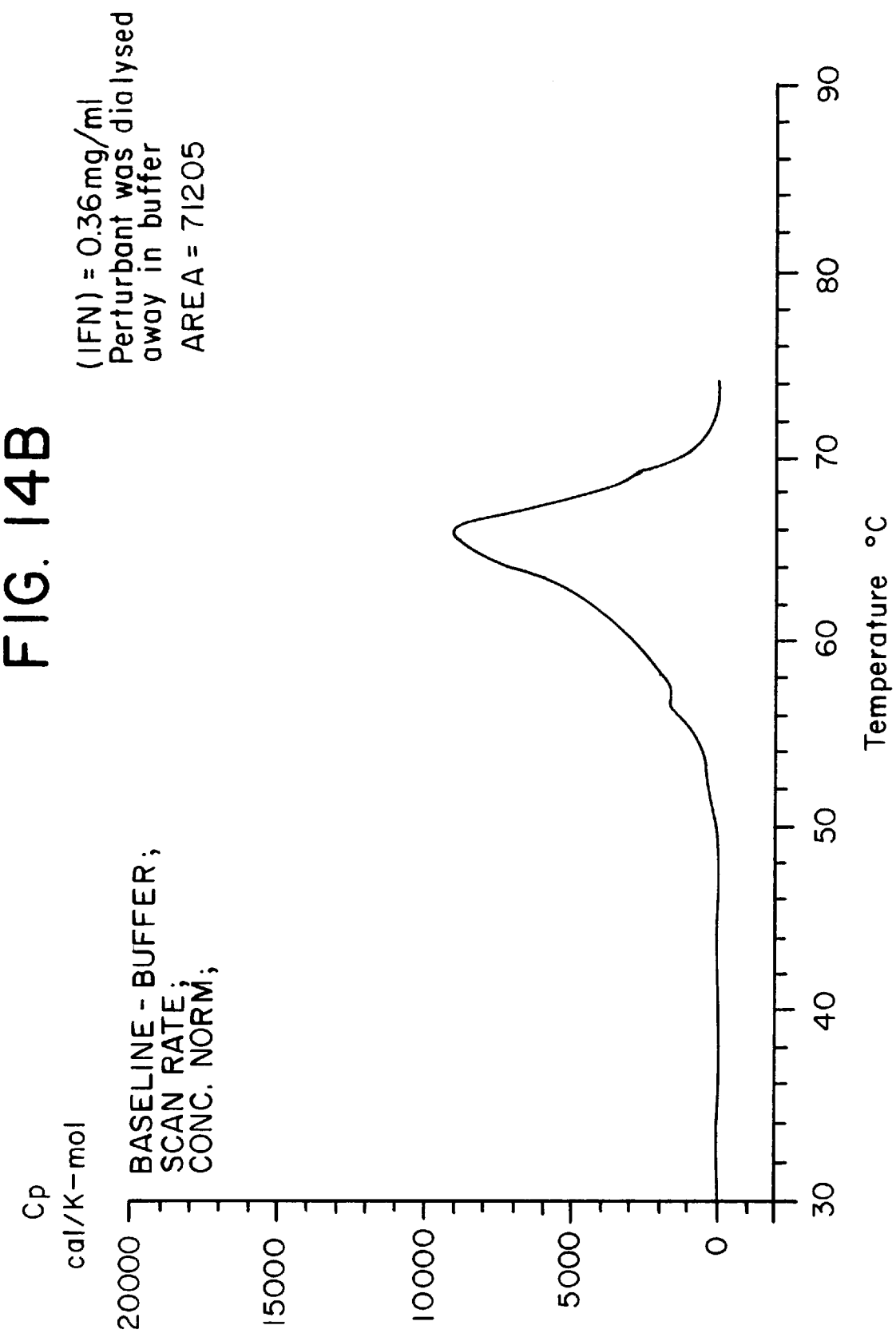

Results are illustrated in FIG. 14A.

α-interferon (0.6 mg/ml) and the perturbant of Example 26 (100 mg/ml) were mixed with no apparent changes in the Cp of the solution. This solution was then dialyzed overnight into phosphate buffer, and the thermogram was rerun. Results are illustrated in FIG. 14B.

The dialyzed sample had essentially the same Tm and the same area under the Cp vs. Tm curve as it did prior to addition of the perturbant. This indicated that not only was the perturbant able to induce conformational changes in the protein but that this process was reversible. Dilution was enough of a driving force to effect disengagement of the perturbant from the active agent.

EXAMPLE 28
Perturbant and α-interferon DSC

The method of Example 6 was followed, substituting the perturbant of Example 26 for the GuHCl.

Results are illustrated in FIG. 15.

The DSC experiments on the equilibrium denaturation of α-interferon indicate the existence of intermediate conformations of the molecule. ΔH vs. Tm plots indicate the energetics of intermediate conformations occupied by α-interferon at each set of experimental conditions.

EXAMPLE 29
In Vivo Administration of Perturbant and α Interferon to Rats

Rats were dosed according to the method of Example 2 with a dosing solution of the perturbant of Example 4 (800 mg/kg) and α-interferon (1 mg/kg). Serum samples were collected and assayed by ELISA according to the procedure of Example 2.

Figure 16:
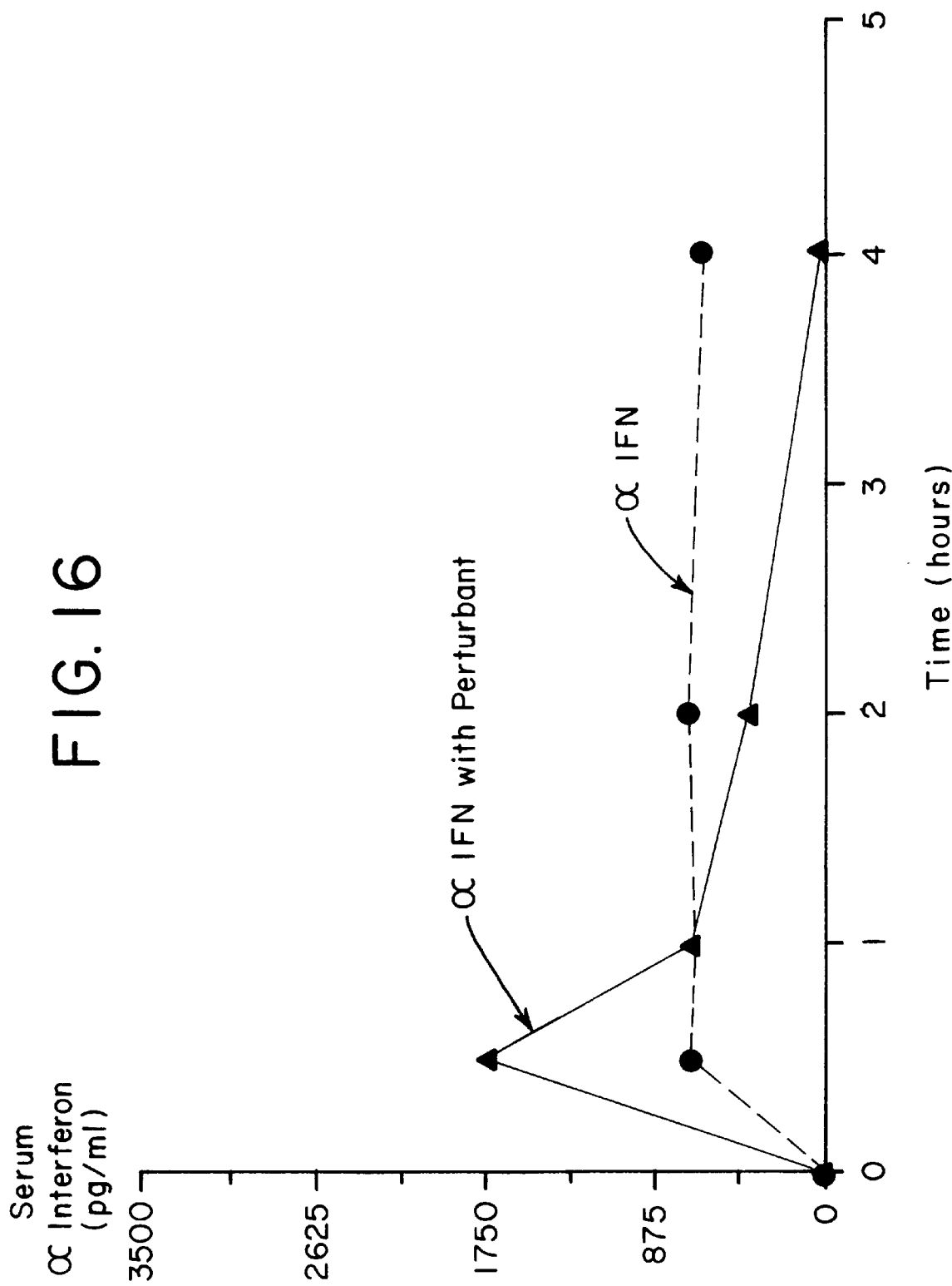

Results are illustrated in FIG. 16.

COMPARATIVE EXAMPLE 29*
In Vivo Administration of a Interferon to Rats

Rats were dosed according to the method of Example 29 with α-interferon (1 mg/kg) without perturbant. Serum samples were collected and assayed according to the procedure of Example 29.

Results are illustrated in FIG. 16.

FIG. 16 illustrates that when active agent mixed with perturbant was orally gavaged into animals, significant serum titers of α-interferon were detectable in the systemic circulation, and the α-interferon was fully active. Confirming data that the delivered α-interferon was fully active included the fact that the serum was assayed by a commercial ELISA kit which utilizes a monoclonal antibody able to recognize an epitope specific to the native conformation of Intron and that the serum was further assayed using the cytopathic effect assay which determined titers of Intron that correlated with the titers measured by ELISA (data not shown). Therefore, the conformational changes which occurred as a result of with the perturbant, were reversible changes.

EXAMPLE 30
Perturbant Concentration Dependent Change in α-Interferon

The method of Example 26 was followed substituting cyclohexanoyl phenylglycine for the perturbant.

Figure 17:
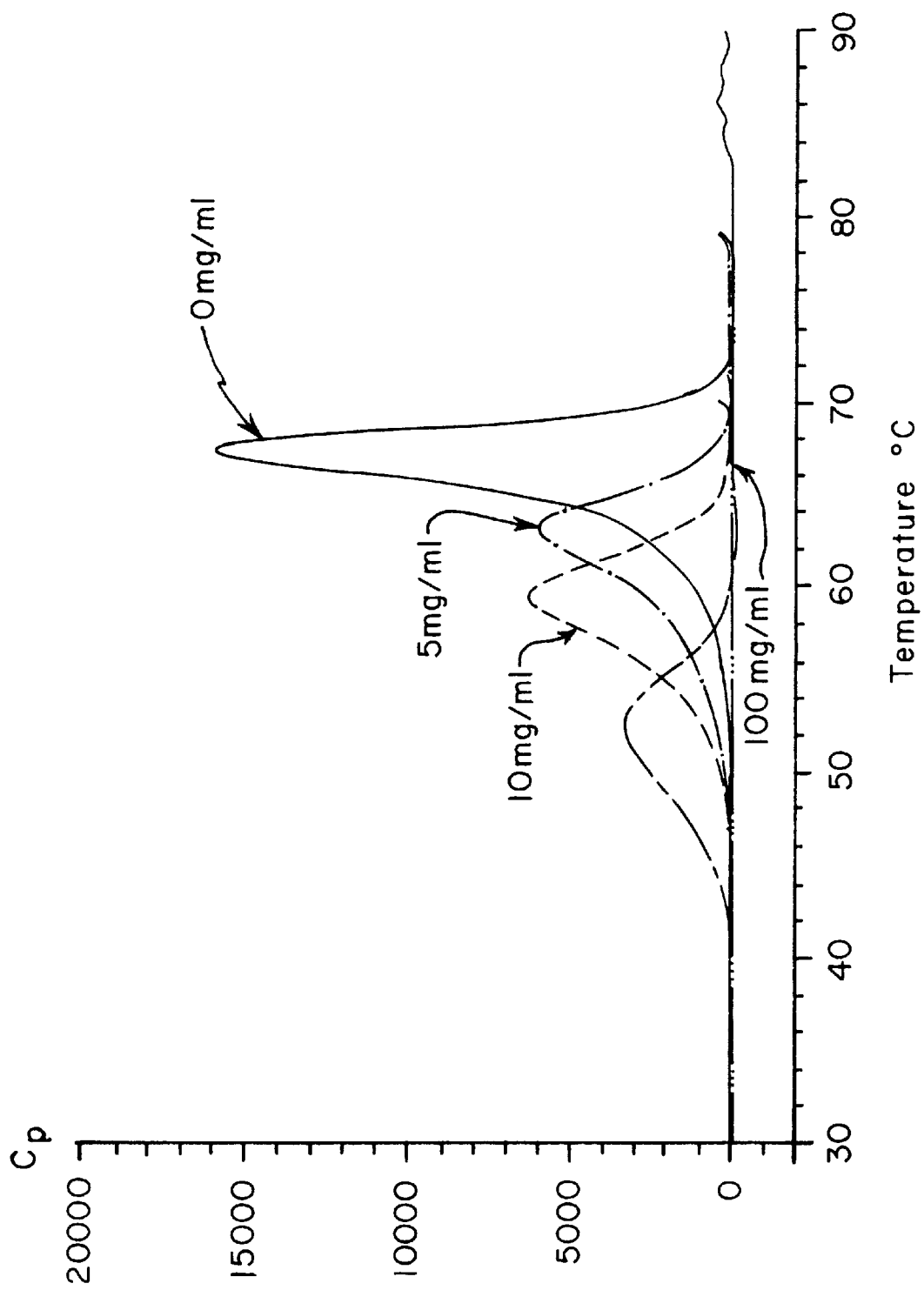

Results are illustrated in Table 10 below and in FIG. 17.

TABLE 10

| α-Interferon + Perturbant DSC | | |
|---|---|---|
| Perturbant mg/ml | Tm ° C. | ΔH cal/mol |
| 0 | 67.12 | 72562 |
| 5 | 63.00 | 42299 |
| 10 | 59.49 | 43058 |
| 25 | 52.79 | 27237 |
| 100 | — | 0 |

Cyclohexanoyl phenylglycine induced conformational changes in α-interferon that were concentration dependent.

EXAMPLE 31

In Vivo Administration of Perturbant and α-interferon to Rats

Rats were dosed according to the method of Example 2 with dosing solutions containing the perturbant of Example 30 (800 mg/kg) and α-interferon 1 (mg/kg). Serum samples were collected and assayed by ELISA according to the procedure of Example 2.

Figure 18:
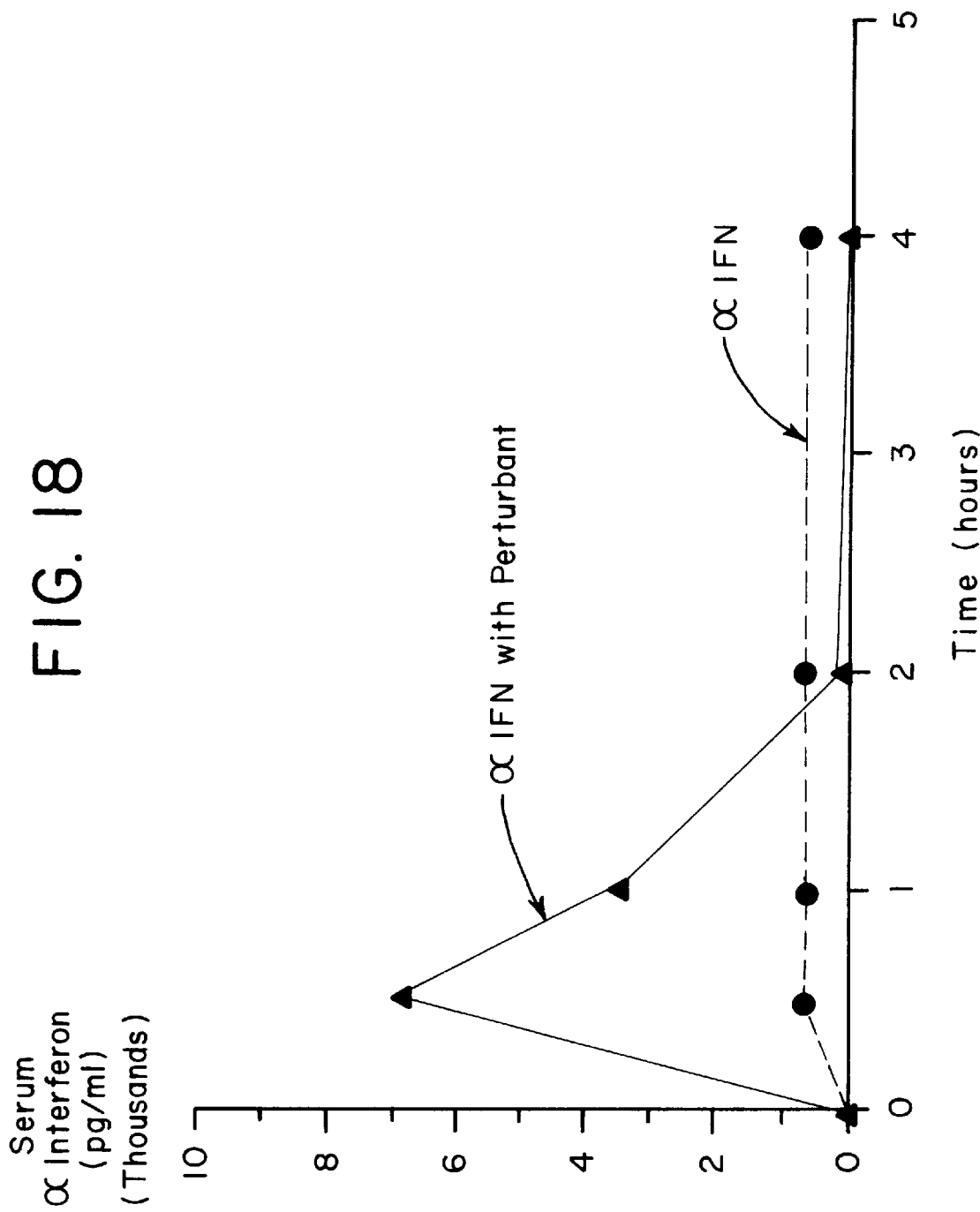

Results are illustrated in FIG. 18.

COMPARATIVE EXAMPLE 31*

In vivo Administration of Perturbant and α-Interferon to Rats

Rats were dosed according to the method of Example 2 with α-interferon (1 mg/kg) without perturbant. Serum samples were collected and assayed by ELISA according to the procedure of Example 2.

Results are illustrated in FIG. 18.

EXAMPLE 32

Perturbant and α-interferon DSC

The method of Example 6 was followed substituting the perturbant of Example 30 for the GuHCl.

Figure 19:
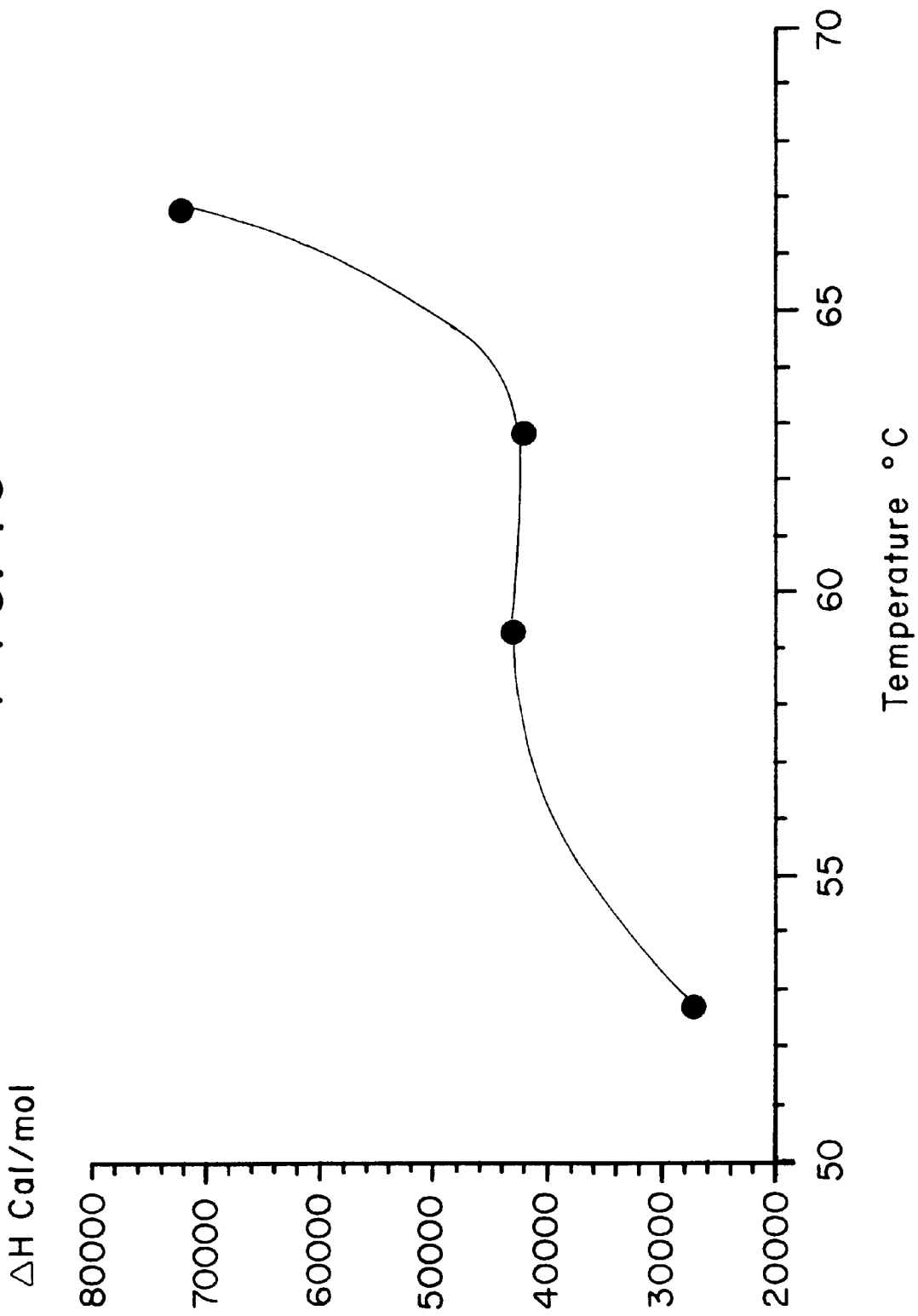

Results are illustrated in FIG. 19.

The ΔH v. Tm plot indicates the existence of an equilibrium intermediate conformation of α-interferon that is stable at below 5 and 25 mg/ml of added cyclohexanoyl phenylglycine perturbant.

EXAMPLE 33

Isothermal Titration Calorimetry of α-interferon with Perturbant

Isothermal titration calorimetry of perturbant complexing with α-interferon was performed at 25° C. at two different pH's. The buffers used were 20 mM NaPhosphate for pH 7.2 and 20 mM NaAc for pH 3.0. α-interferon solution was dialyzed before the experiment to reach the appropriate pH. Dry perturbants were weighed and diluted in dialysate.

ITC was conducted on a MicroCal OMEGA titration calorimeter (MicroCal Inc. Northampton, Mass.). Data points were collected every 2 seconds, without subsequent filtering. α-interferon solution placed in 1.3625 mL cell was titrated using a 250 µL syringe filled with concentrated perturbant solution. A certain amount of titrant was injected every 3–5 minutes for up to 55 injections.

A reference experiment to correct for the heat of mixing of two solutions, was performed identically except that the reaction cell was filled with buffer without active agent.

Analysis of the data was performed using the software developed at the Johns Hopkins University Biocalorimetry Center.

The titration at pH 7.2 included 53 injections of 2 µL of the perturbant of Example 30 (50 mg/mL=191.6 mM (MW 261)) and α-interferon (1.3 mg/mL 0.067 mM (MW 19400)).

Figure 20:
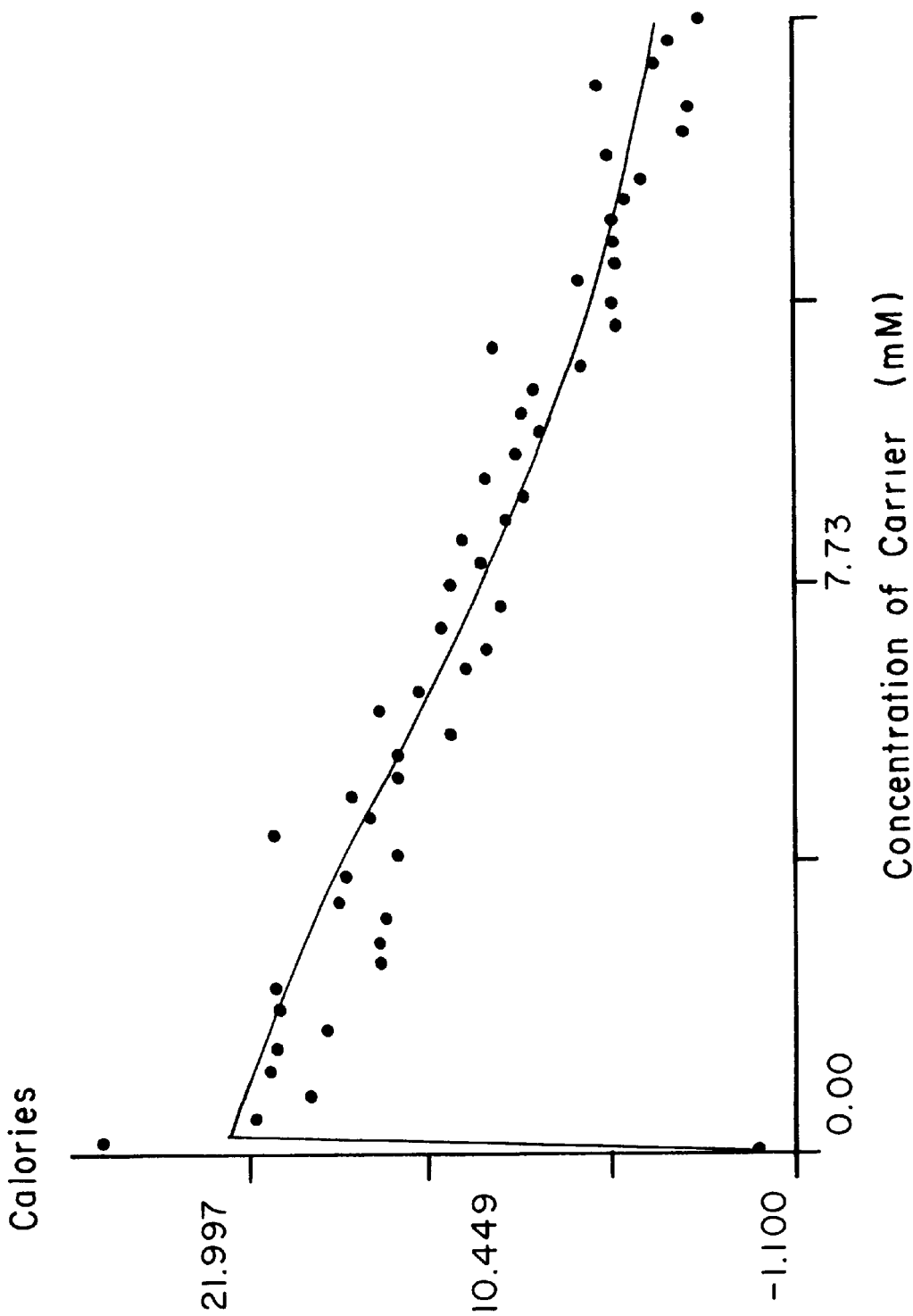

Results are illustrated in FIG. 20.

Curve fitting indicated multiple independent sites:

n(1)=121.0354 where n=# of completed perturbant molecules

ΔH(1)=58.5932 cal/Mole perturbant log 10 Ka(1)=2.524834 where Ka=association constant x-axis units are concentration of carrier in mM.

y-axis units represent heat/injection expressed in calories.

At pH 3, complexing resulted in a negative enthalpy.

COMPARATIVE EXAMPLE 33*

Isothermal Titration Calorimetry of Perturbant

The method of Example 33 was followed, substituting 53 injections of 2 µl for the perturbant (50 mg/mL=191.6 mM) [IFN]=0 mg of Example 30 without active agent.

Example 33 and Comparative Example 33 illustrate that α-interferon has a positive enthalpy and a binding constant ($K_d \approx 10^{-3}$M).

EXAMPLE 34

Isothermal Titration Calorimetry of α-interferon and Perturbant Complexing

The method of Example 33 was followed substituting the perturbant of Example 26 for the perturbant of Example 30.

The titration at pH 7.2 included two runs of 55 injections each of 5 µL of perturbant (50 mg/mL=181 mM (FW 277)) and α-interferon (2.31 mg/mL 0.119 mM, (MW 19400)).

Figure 21:
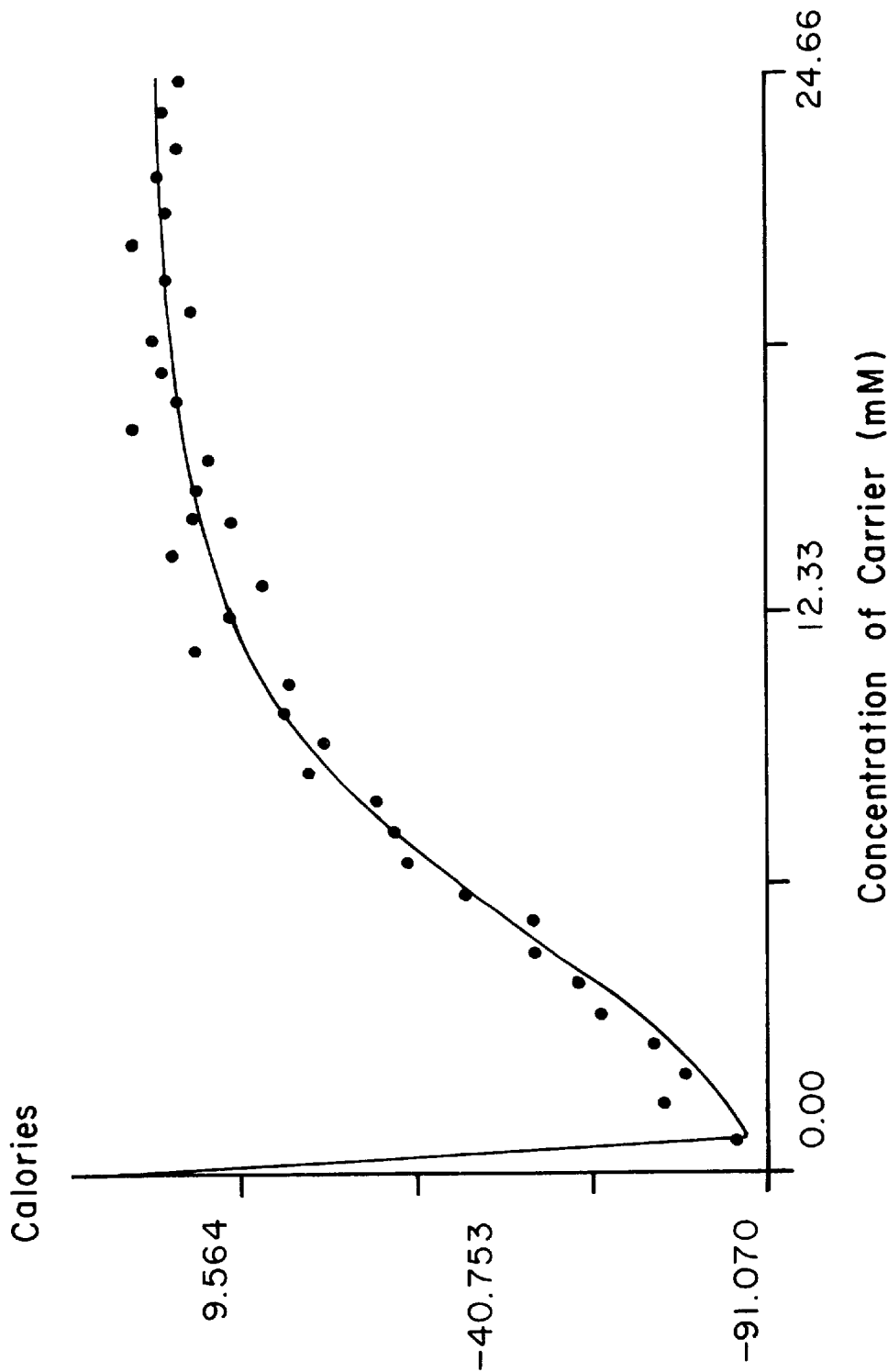

Results are illustrated in FIG. 21.

Curve fitting indicated multiple independent sites:

n (1)=55.11848 where n=# of complex perturbant molecules

ΔH (1)=−114.587 cal/Mole perturbant log 10 Ka (1)=2.819748 where Ka=association constant x-axis units are concentration of carrier in mM.

y-axis units represent heat/injection expressed in calories.

Complexing of perturbant to α-interferon at pH 3.0 resulted in precipitation of the complex out of the solution. Due to the heat effect produced by this process, it was impossible to measure the complexing parameters.

COMPARATIVE EXAMPLE 34* isothermal Titration Calorimetry of Perturbant

The method of Example 34 was followed, substituting 55 injections of 5 µl of the perturbant of Example 26 (50 mg/mL=181 mM) in 20 mM sodium phosphate pH 7.2 without active agent.

The perturbant of Example 26 complexed with α-interferon resulted in a negative enthalpy and a comparable binding constant to that of the perturbant of Example 30 and α-interferon.

Examples 33 and 34 indicate that the stronger the perturbant complexes with the active agent and the more thermodynamically stable the intermediate state of the active agent, the greater the bioavailability of the active agent.

Therefore, by plotting the ΔH v. Tm curve for an active agent and a perturbant, those perturbants that induce little or no enthalpic change over the broadest range of Tm would be preferred perturbants. It is believed that perturbants that stabilize the intermediate state to a greater extent will result in more efficient delivery of the active agent.

EXAMPLE 35

Comparison of the Effects of Three Perturbants On ΔH vs. Tm Plots with α-interferon DSC experiments were carried out according to the procedure of Example 26, with 0.5 mg/ml α-interferon mixed with (1) benzoyl para-amino phenylbutyric acid, (2) the perturbant of Example 30, or (3) the perturbant of Example 26.

Benzoyl para-amino phenylbutyric acid was poorly soluble under the buffer conditions. Maximum concentration at which the solution was still transparent at room temperature was ~8 mg/mL. Therefore, the concentrations of the perturbant used were 2, 4, and 6 mg/mL. Results are illustrate in FIGS. 22 and 23. The dashed line in FIG. 22 represents the linear least squares, and the regression equation is at the top of FIG. 22.

$$Y=-1.424e^5+3148.8x$$

Figure 22:
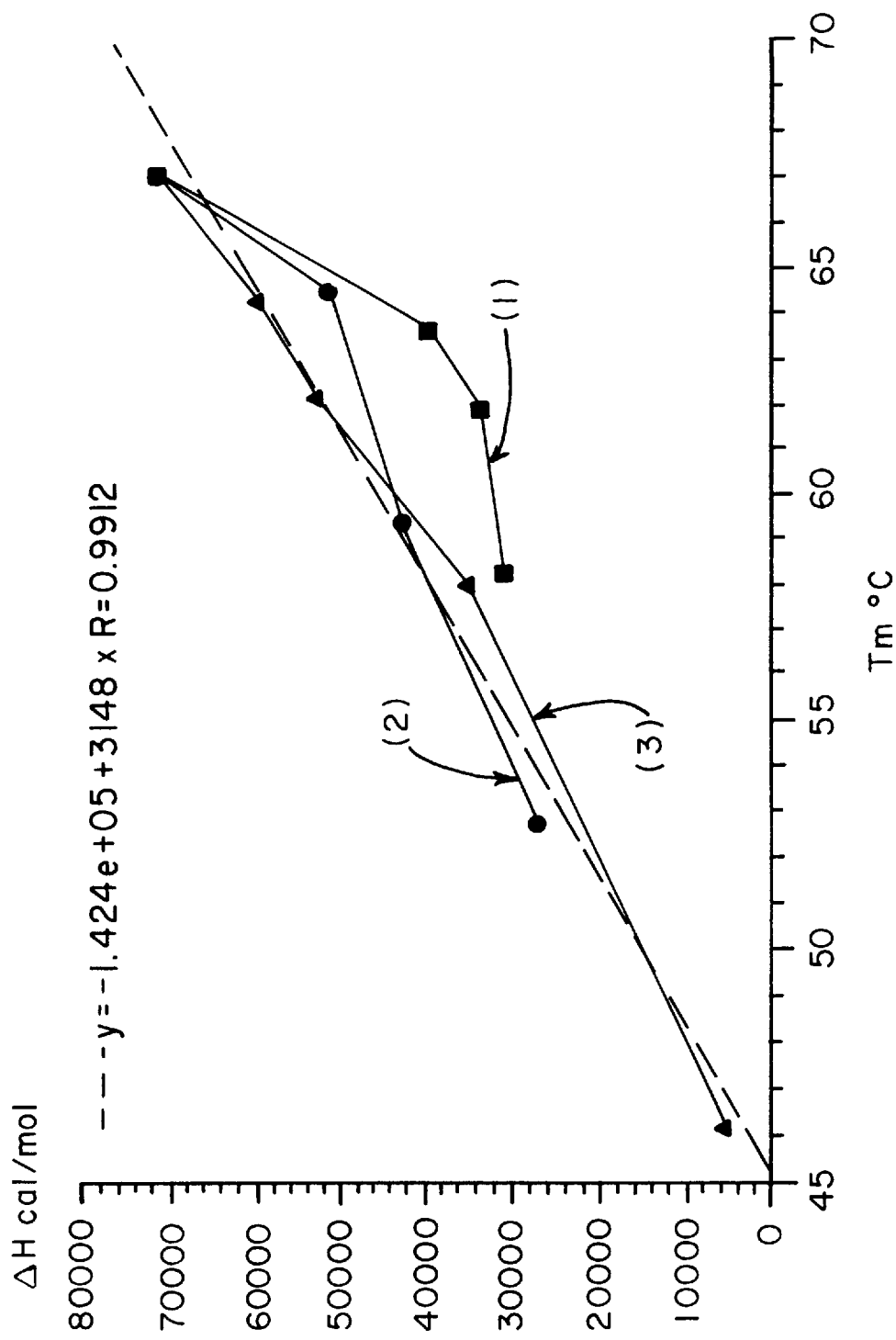
Figure 23:
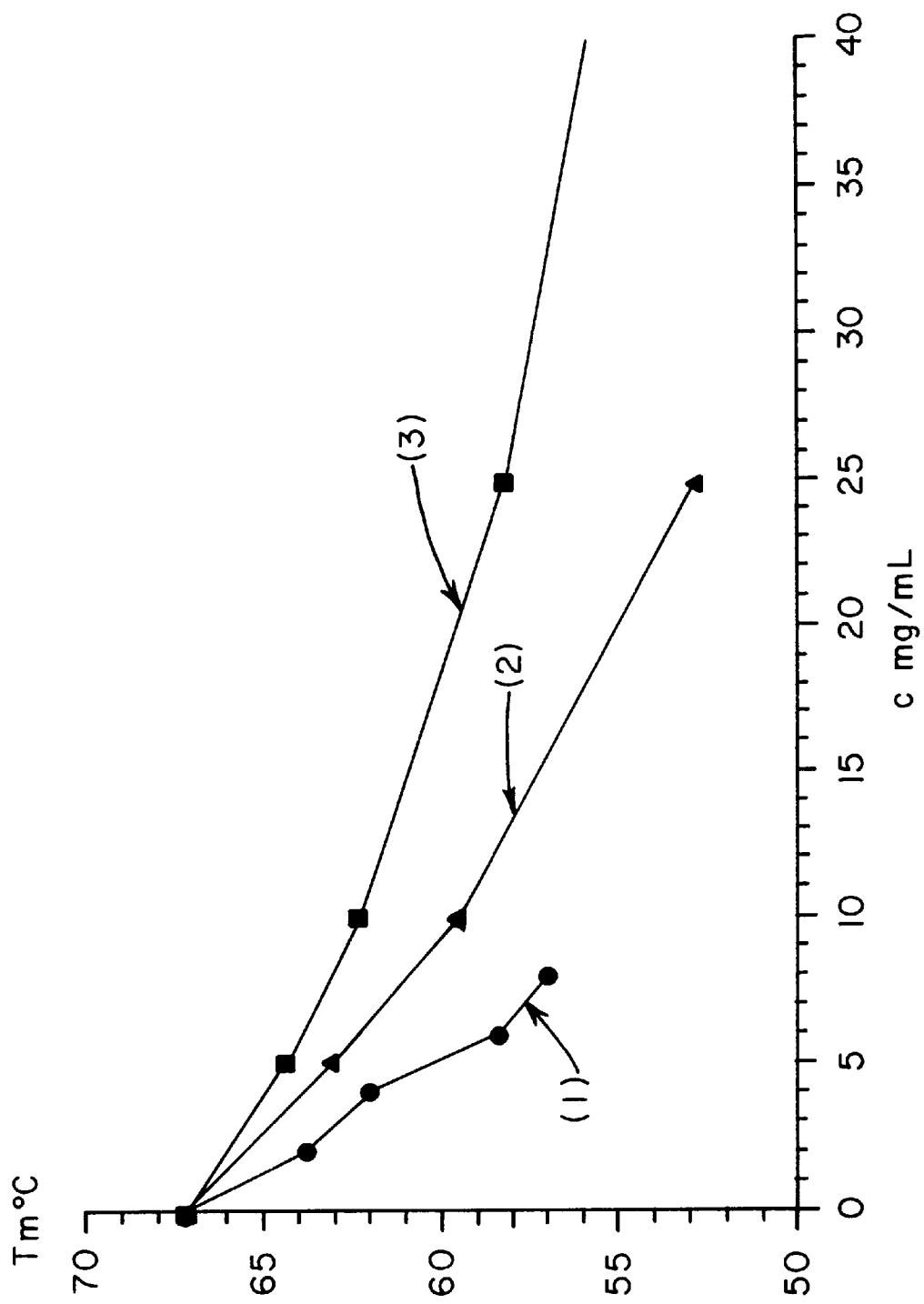

FIGS. 22 and 23 illustrate that conformational changes in α-interferon are more readily produced by benzoyl para-amino phenylbutyric acid than by the perturbants of Examples 30 and 26, and that such changes are more readily produced by the perturbant of Example 30 than by the perturbant of Example 26.

EXAMPLE 36
Isothermal Titration Calorimetry of α-interferon and Complexing

ITC was performed according to the method of Example 33 with 40 injections of 5 μL of the perturbant benzoyl para-amino phenylbutyric acid (7.5 mg/mL=24.59 mM, (FW 305)) and α-interferon (2.5 mg/mL=0.129 mM, (MW 19400)).

Figure 24:
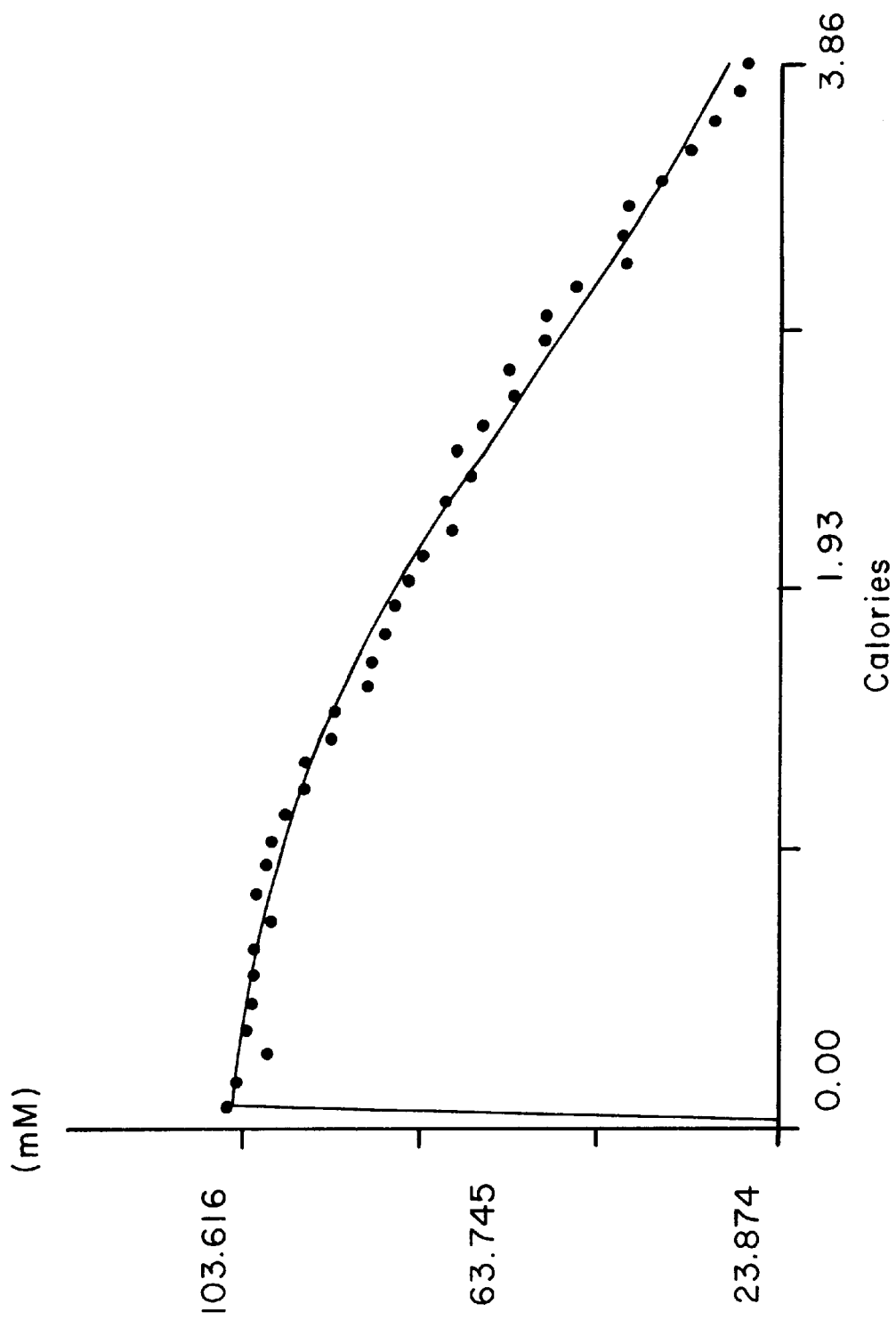

Results are illustrated in FIG. 24.
Curve fitting indicated multiple independent sites:
n (1)=23.69578 where n=# of complexed perturbant molecules
ΔH (1)=791.5726 cal/Mole perturbant
log 10 Ka (1)=3.343261 where Ka=association constant
x-axis represents concentration of carrier in mM.
y-axis represents heat/injection expressed in calories.

COMPARATIVE EXAMPLE 36*

ITC was performed according to the method of Example 36 with 40 injections of 5 μl of the perturbant benzoyl para-amino phenylbutyric acid (7.5 mg/mL=24.59 mM) in 20 mM NaPhosphate pH 7.2 buffer, without active agent.

The apparent dissociation constant for the perturbant of Example 35 is greater than that for the perturbant of Example 30 ($10^4$M) at pH 7.

Therefore, benzoyl para-amino phenylbutyric acid complexes more strongly to α-interferon and induces the native state-reversible intermediate conformational state at lower concentrations of perturbant.

EXAMPLES 37–39
Comparative In Vivo Pharmacokinetics of Various Perturbants and α-interferon Rats were dosed according to the procedure of Example 2 with dosing solutions containing the perturbant of Example 26 (800 mg/kg) (1), the perturbant of Example 30 (800 mg/kg) (2), or the perturbant of benzoyl para-amino phenylbutyric acid (300 mg/kg) (3) and α-interferon at 1 mg/kg. Serum samples were collected and assayed by ELISA according to the procedure of Example 2.

Figure 25:
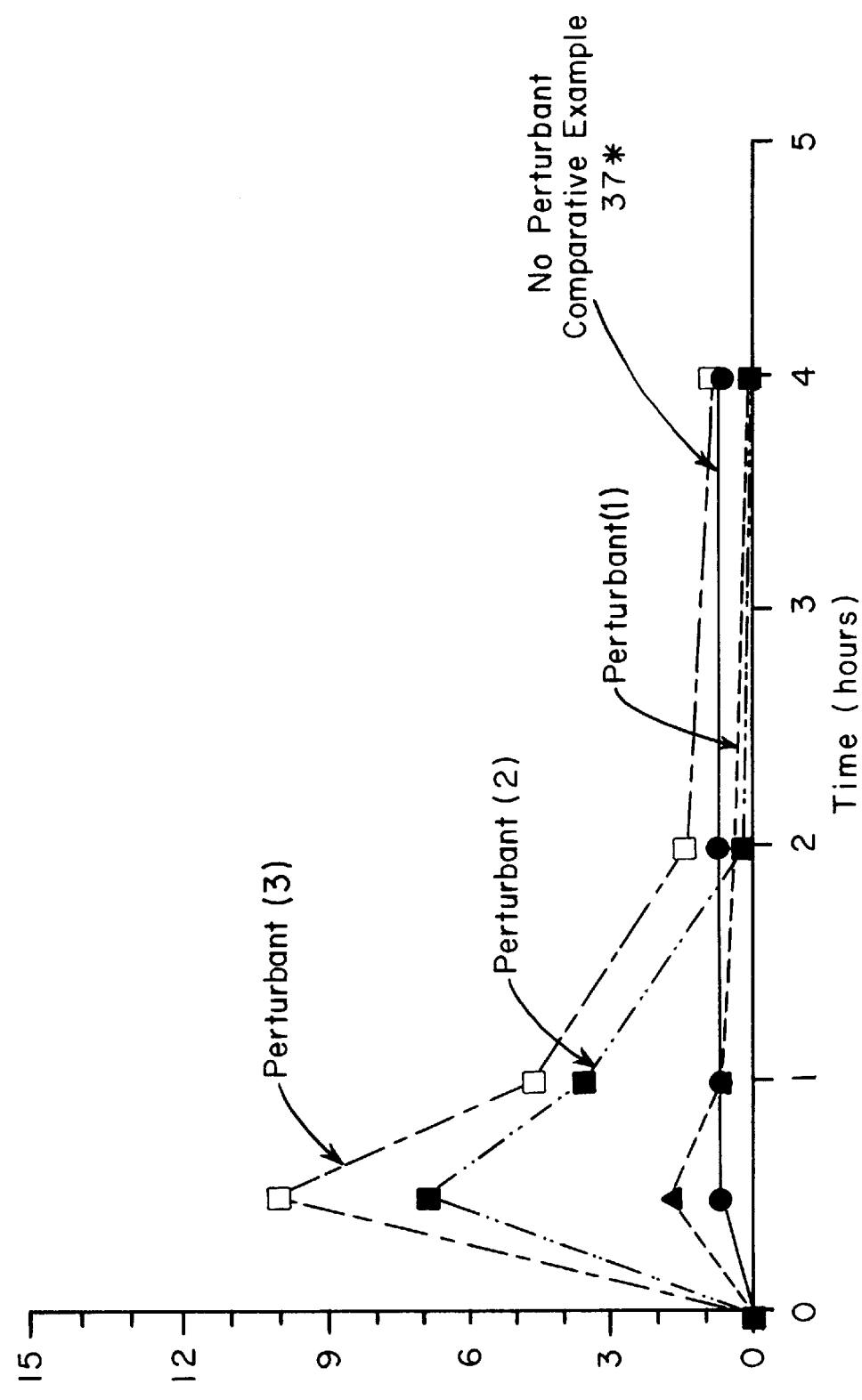

Results are illustrated in FIG. 25.

COMPARATIVE EXAMPLE 37*
In Vivo Pharmacokinetics of α-interferon

Rats were dosed according to the method of Example 37 with α-interferon without perturbant. Serum samples were collected and assayed by ELISA according to the procedure of Example 2.

Results are illustrated in FIG. 25.

Examples 35–39 illustrate that in vivo potency was correctly predicted by in vitro modeling.

EXAMPLES 40–42
Comparative In Vivo Pharmacokinetics of Various Perturbants with rhGh in Hypophysectomized Rats Rats were dosed according to the procedure of Example 2, with dosing solutions containing the perturbants salicyloyl chloride modified L-phenylalanine (1.2 g/kg) (40), phenylsulfonyl para-amino benzoic acid (1.2 g/kg) (41), or cyclohexanoyl chloride modified L-tyrosine (1.2 g/kg) (42) mixed with rhGh (1 mg/kg).

Rats were hypophysectomized according to the procedure of Loughna, P. T. et al, *Biochem. Biophys. Res. Comm.*, Jan. 14, 1994, 198(1), 97–102. Serum samples were assayed by ELISA (Medix Biotech, Inc., Foster City, Calif., HGH Enzyme Immunoassay Kit).

Figure 26:
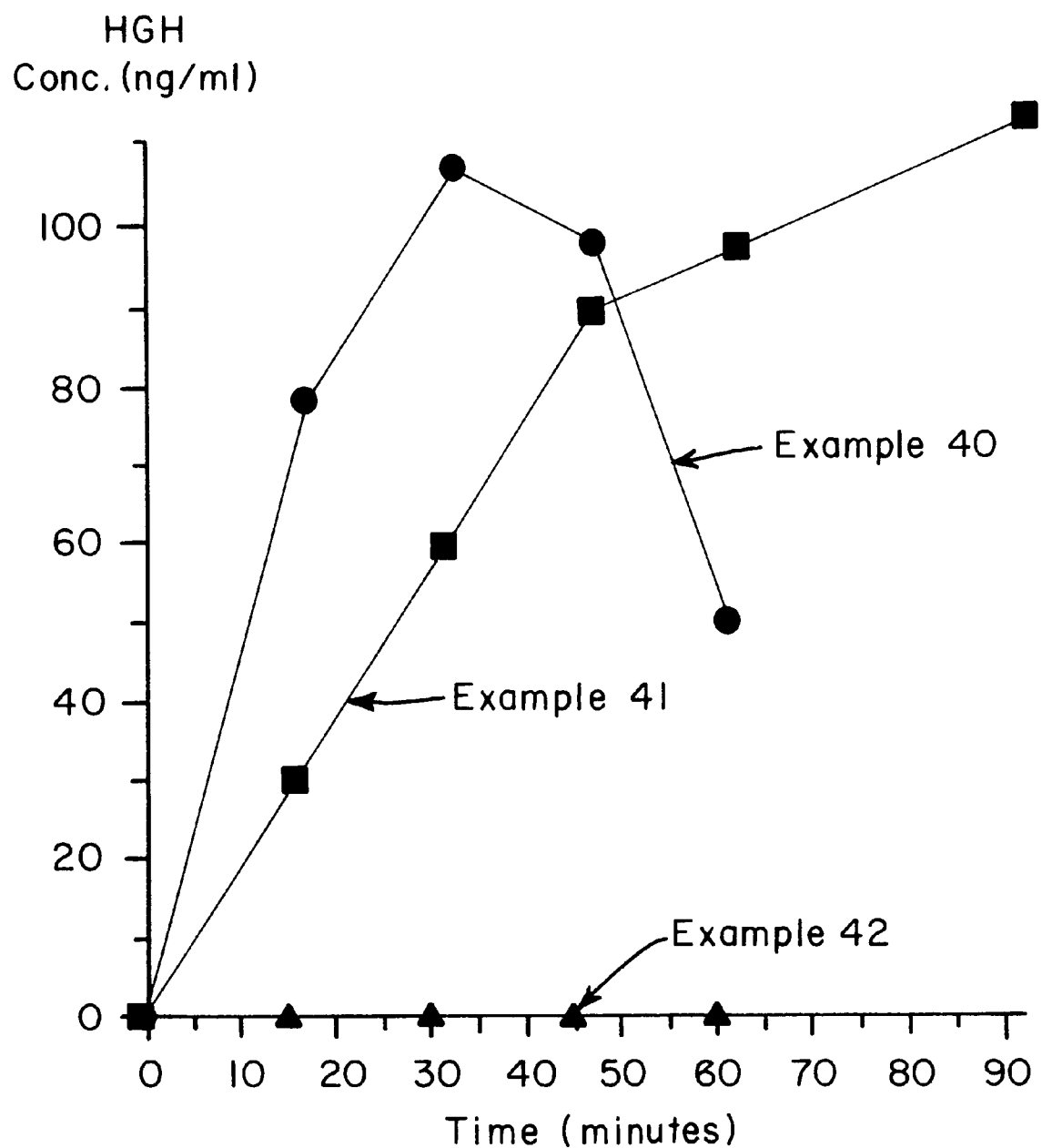

Results are illustrated in FIG. 26.

EXAMPLES 43–45
Isothermal Titration Calorimetry of rhGH at pH 7.5 and 4.0 with Different Perturbants The ability of rhGh to complex with various perturbants was assessed by ITC using a Microcal Omega titrator, usually equilibrated at 30° C. The sample cell of the calorimeter was filled with degassed rhGH (usually at 0.25 mM) prepared in 50 mM phosphate buffer, pH 7.5 or 4.0. The perturbant (cyclohexanoyl chloride modified L-tyrosin (a), salicyloyl modified L-phenylalanine (b), or phenylsulfonyl-para-amino benzoic acid (c)) was then placed in the dropping syringe at 1 mM (for pH 7.5) and 2.5 mM, (for pH 4.0). Twenty to twenty-five 10 μl injections were made into rapidly mixing (400 rpm) solution with 2 minute intervals between injections.

Initial concentration of perturbant placed in the calorimeter sample cell assumed a formula weight of 200 for each perturbant. The pH of each solution was checked after dissolution, but no adjustments of the pH were required. All experiments were performed at 30° C. Initial concentration of rhGh placed in the dropping syringe assumed a molecular weight of 20,000 for rhGh. The pH of each solution was checked after dissolution, but no adjustment of the pH was required.

The heats of reaction were determined by integration of the observed peaks. To correct for heat of mixing and dilution, a control experiment was also performed under identical conditions where aliquots of the test perturbant or rhGh were added to buffer solution only. The sum total of the heat evolved was plotted against the total perturbant concentration to produce the isotherm from which the association constant ($K_A$, M), enthalpy change (ΔH, kcal/mol), entropy change (ΔS eu), and N, and the stoichiometry of perturbant molecules complexed per equivalent of complexed supramolecular complex, were determined by curve-fitting the binding isotherm against the binding equation described for perturbant complexing in a supramolecular complex possessing one set of independent perturbant complexing sites. The data were deconvoluted using the nonlinear least squares algorithm supplied in the software of the manufacturer.

Results are illustrated in Table 11 below.

TABLE 11

Isothermal Titration Calorimetry of rhGH at pH 7.5 and 4.0 with Different Perturbants

| Perturbant | rhGh (mM) | KD (M) | ΔH (kcal/mol) | ΔS (eu) | N |
|---|---|---|---|---|---|
| pH 7.5 | | | | | |
| A at 0.25 mM | 1.0 | $9.88 \times 10^{-5}$ | +1.4 | +23.5 | 7.0 |
| B at 0.25 mM | 1.0 | $1.11 \times 10^{-6}$ | +2.1 | +35.0 | 0.7 |
| C at 0.25 mM | 1.0 | $1.11 \times 10^{-9}$ | +0.8 | +44.0 | 10.0 |
| pH 4.0 | | | | | |
| A at 0.25 mM | 1.0 | $7.81 \times 10^{-5}$ | −1.5 | −5.6 | 2.3 |
| B at 0.25 mM | 1.0 | $1.61 \times 10^{-9}$ | −35.6 | −90.0 | 155.9 |
| C at 0.25 mM | 1.0 | $2.67 \times 10^{-8}$ | −1.2 | −30.0 | 122.0 |

A = cyclohexanoyl chloride modified L-tyrosine
B = salicyloyl modified L-phenylalanine
C = phenylsulfonyl-para-aminobenzoic acid The positive ΔS values at pH 7.5 indicate that complexing at this pH results in structural change.

EXAMPLES 46 AND 47

Pancreatin Inhibition Assay with α-interferon and Perturbants

The assay for pancreatin activity was prepared as follows: 0.1 mL of a stock solution of α-interferon (9.1 mg/mL, 20 mM $NaH_2PO_4$, pH 7.2) (Schering-Plough Corp.) was added to 2.5 mL of either phenylsulfonyl-para-aminobenzoic acid perturbant (46) or cyclohexanoyl phenylglycine perturbant (47) (200 mg/mL) in 5 mM $KH_2PO_4$, pH 7.0. Incubation was carried out at 37° C. for 30 and 60 minutes following the addition of 0.1 mL of USP pancreatin (20 mg/mL) (Sigma Chemical Co.) 0.1 mL aliquots were withdrawn at those times points. Enzyme reactions were stopped by the addition of protease inhibitors (Aprotinin and Bowman-Birk Inhibitor (BBI), each at 2 mg/mL) and were diluted five-fold to quantitate α-interferon left intact. A reverse phase HPLC method using a Butyl C-4 cartridge (3.0×0.46 cm, Rainin) and employing gradient elution between 0.1% TFA/water and 90% ACN in 0.1% TFA coupled with UV detection at 220 nm was used for separating and quantitating α-interferon. The α-interferon at 0 minutes was quantitated from an aliquot prior to the addition of pancreatin and was taken to be 100%.

Figure 27:
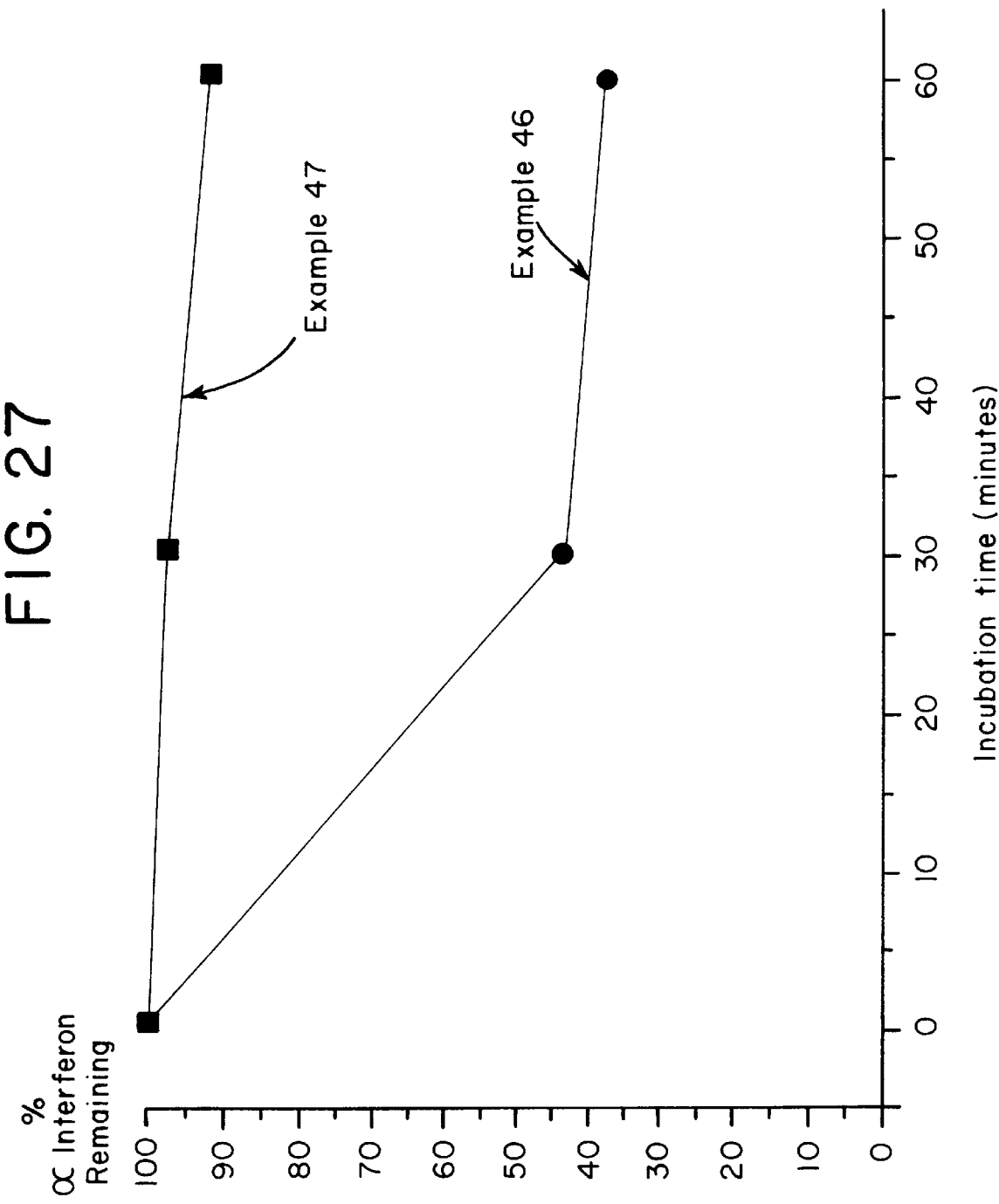

Results are illustrated in FIG. 27.

Examples 46 and 47 illustrate that both supramolecular complexes resisted enzymatic degradation. However, in additional testing no correlation was shown between the enzyme inhibitors potency and the ability to deliver drug.

EXAMPLE 48

DSC of Heparin at pH 5.0

DSC thermograms of heparin at pH 5.0 were conducted according to the method of Example 11 using pH, GuHCl, and ionic strength as perturbants.

Thermograms were corrected by subtraction of a heparin 0.05M NaCl-phosphate buffer blank, but an individual blank was not used for each NaCl concentration.

Figure 28:
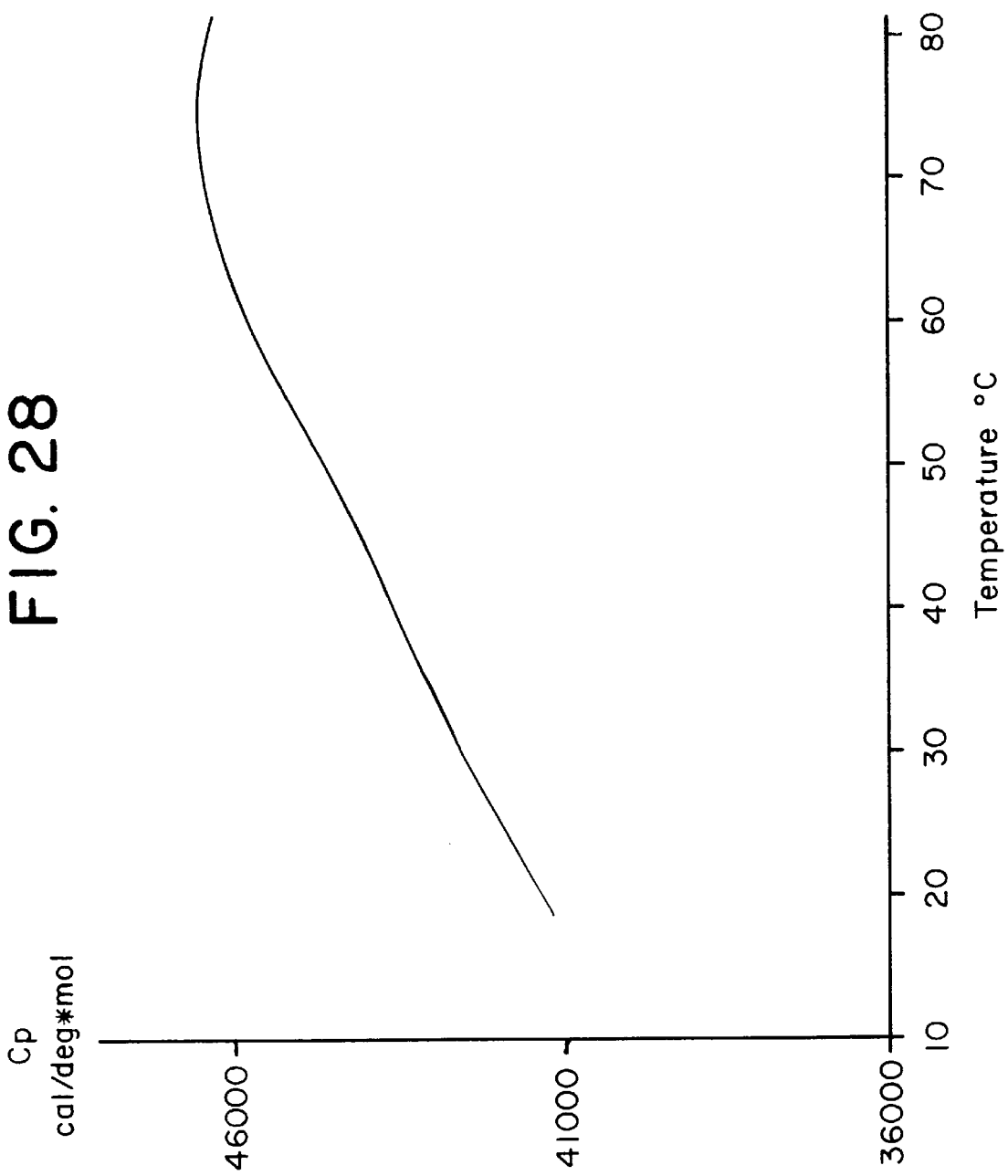

Results are illustrated in Tables 12–14 below and in FIG. 28.

TABLE 12

Effects of pH on the DSC Spectrum of 20 μg/ml Heparin in 50 mM Phosphate Buffer

| | Tm (Cp,max) | ΔH (kcal/mol) | $ΔH_{vH}$ (kcal/mol) |
|---|---|---|---|
| pH 6.0 | 62.5 | 232.1 | 13.8 |
| pH 6.5 (a) | 62.7 | 213.9 | |
| (b) | 71.8 | 751.9 | 56.8 |
| pH 7.0 (a) | 47.1 | 187.1 | |
| (b) | 72.9 | 136.4 | 27.6 |
| pH 7.5 | 66.2 | 499.4 | 83.8 |

(a) = a domain
(b) = b domain

TABLE 13

Effects of 10M Guanidine Hydrochloride in 50 mM Phosphate Buffer on the DSC Spectrum of Heparin

| | Tm (Cp,max) | ΔH (kcal/mol) | $ΔH_{vH}$ (kcal/mol) |
|---|---|---|---|
| heparin | 67.2 | 499.4 | 83.8 |
| heparin + 0.5M GuHCl | 50.5 | 287.3 | 170.9 |
| heparin + 1.0M GuHCl | 60.5 | 415.0 | 97.1 |
| heparin + 1.5M GuHCl | — | 1716.5 | 24.3 |
| heparin + 2.0M GuHCl | — | 2533.7 | 19.2 |

TABLE 14

Effect of Ionic Strength on the DSC Spectrum of 20 μg/ml of Heparin in 50 mM Phosphate Buffer pH 7.0

| | Tm (Cp,max) | | ΔH (kcal/mol) | $ΔH_{vH}$ (kcal/mol) |
|---|---|---|---|---|
| 0.0M NaCl | 47.1 | 187.1 | 72.9 | 136.4 |
| 0.25M NaCl | 46.1 | 0.112 | not present | |
| 0.50M NaCl | 41.6 | 0.094 | not present | |
| 0.75M NaCl | 27.5 | 0.00 | not present | |
| 1.0M NaCl | no transition observed | | | |

These data indicate that non-proteinaceous active agents are able to change conformation in response to a perturbant.

EXAMPLE 49

Column Chromatography of Heparin and Perturbants
The following materials were used:
Column:
10 mm×30 cm, low pressure, glass column from Pharmacia w/adjustable bed volume. The bed volume used was 22 cm at a pressure of 0.8 Mpa.
Packing:
Heparin covalently bonded to Sepharose CL-6B with no linker molecule.
Sepharose fractionation range: 10,000–4,000,000.
The density of heparin was 2 mg/cc as per Pharmacia Q.C. Department.
Conditions:
The mobil phase was 67 mM phosphate buffer, pH7.4.
The flow rate was 1.5 mL/min isocratic.
The run time was 45 minutes.
Sample detection was done wit Perkin Elmer refractive index detector.
Column integrity was confirmed by injecting protamine and observing a retention time greater than 1 hour. Void volume was determined by injecting water and measuring time of elution.

Each of the perturbants of Table 15 below (5 mg) was independently dissolved in 1 mL of mobil phase and injected (100 ul) into the column. Time of elution was measured. K' value was determined by using the following equation (as per USP):

$$K'=(\text{Ret. time Carrier}/\text{Ret. time Water})-1$$

Figure 29:
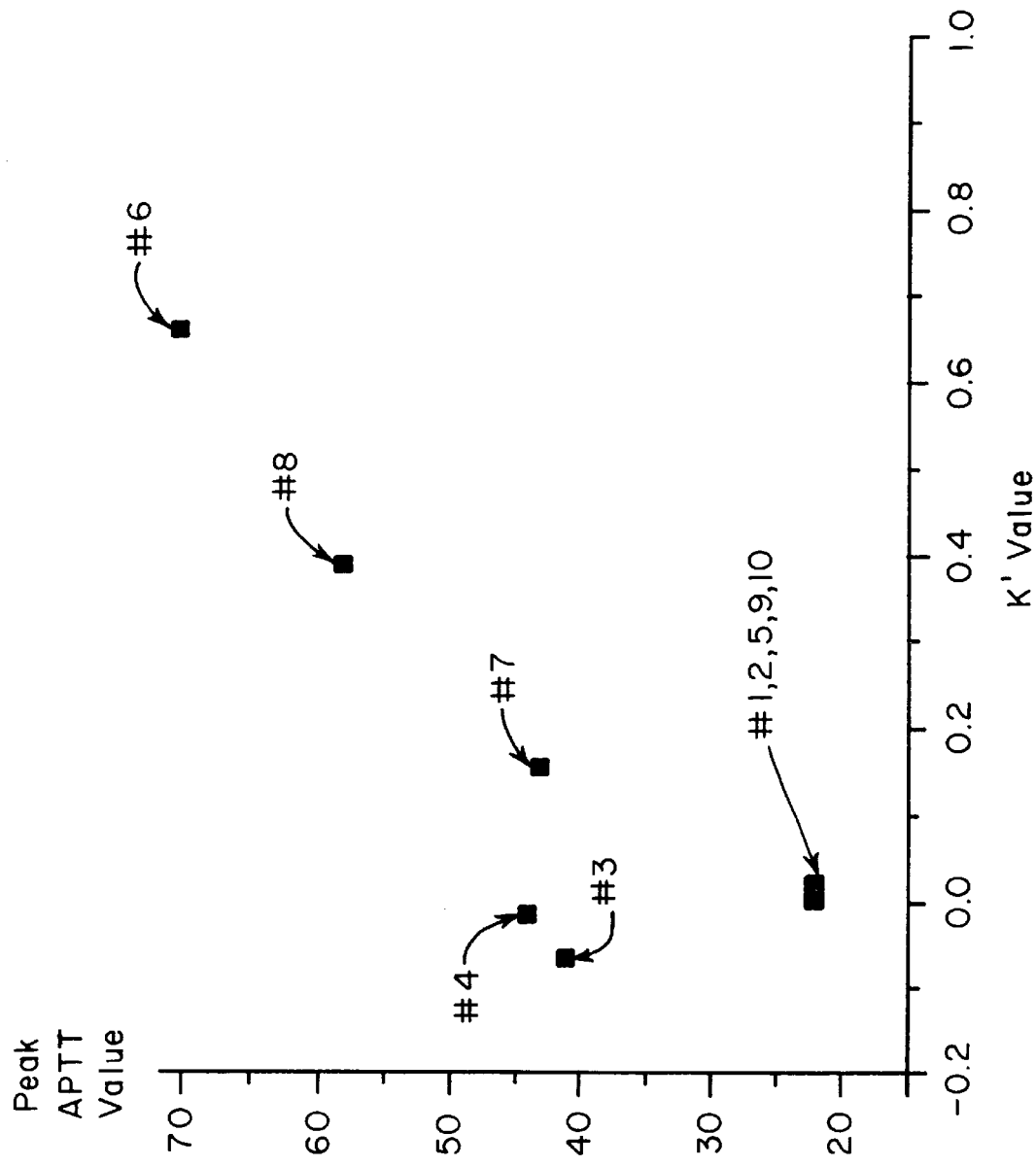

The results were compared between each perturbant as well as their respective in vivo performance in FIG. 29. K' (the degree of retardation) values in the figure have been corrected by subtraction of the K' value determined from the sepharose column from the K' value determined from the heparin-sepharose column.

TABLE 15

PERTURBANTS

| | |
|---|---|
| cyclohexylidenebutyric acid(2)-Na salt | #1 |
| cylcohexanebutyroyl(2-)aminobutyric acid(4) | #2 |
| phenylacetyl-para-aminobutyric acid | #3 |
| ortho-methylcyclohexanoyl-aminobutyric acid(4) | #4 |
| phenylacetyL-aminohexanoic acid(6-) | #5 |
| cinnamoyL-para-aminophenylbutyric acid | #6 |
| cyclohexanebutyroyl(2-)-para-aminophenylbutyric acid | #7 |
| hydrocinnamoyl-para-aminophenylbutyric acid | #8 |
| cyclohexanebutyroyl(2-)-leu-leu | #9 |
| cyclohexanebutyroyl(2-)-gly | #10 |

EXAMPLE 50

Oral Administration of Heparin to Rats

Rats were dosed with the dosing solutions of Table 16 below according to the procedure of Example 2. Blood was collected, and activated partial thromboplastin time (APTT) was performed as described in Henry, J. B., *Clinical Diagnosis and Management by Laboratory Methods*, W. B. Saunders, 1979.

Figure 30:
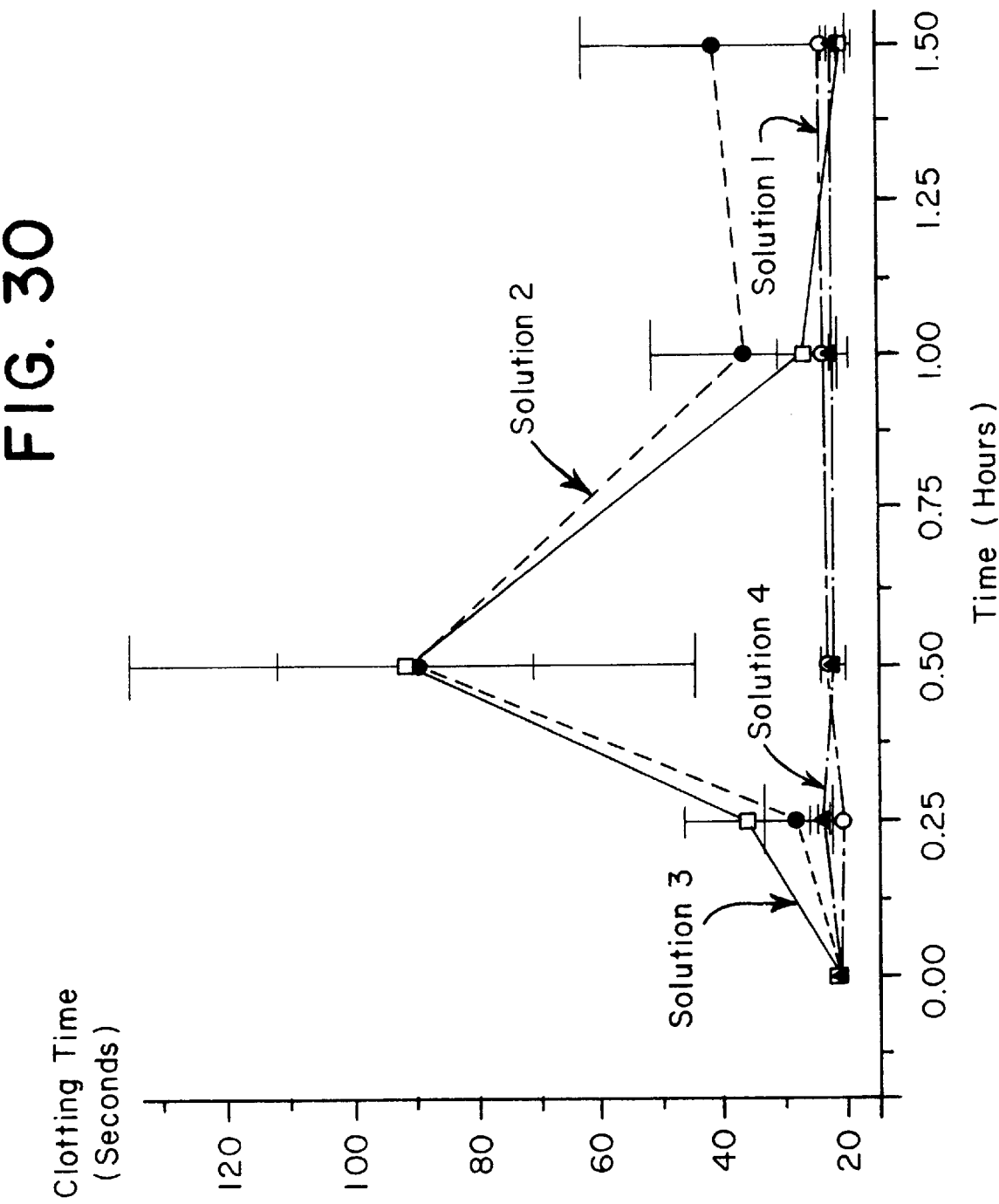

Results are illustrated in FIGS. 29 and 30.

FIG. 29 illustrates that as predicted in the model, the greater the binding to heparin the greater the elevation of APTT. The data suggests that at K' values below 0.2, activity is likely to be poor. At K' values >0.2, activity will be significant.

The data indicate a correlation between the retardation by the heparin sepharose column relative to just a sepharose column and the increased in vivo activity as measured by elevation of APTT. Notably protamine, which binds most strongly to heparin, has no oral bioavailability (K'=3.68). This indicates that balancing binding strength and conformational changes with the ability to dissociate will optimize the full complement of biological activity of the drug.

TABLE 16

HEPARIN/PERTURBANTS DOSING SCHEDULES

Solution 1 = cinnamoyl-para-aminophenylbutyric acid pH 7.5, N = 5
Solution 2 = cinnamoyl-para-aminophenylbutyric acid (300 mg/kg) + Heparin (100 mg/kg) in propylene glycol/water (1:1, pH 7.4)
Solution 3 = Heparin (100 mg/kg, pH 7.4, N = 5)
Solution 4 = hydrocinnamoyl-para-aminophenylbutyric acid (300 mg/kg) + Heparin (100 mg/kg) in propylene glycol/water (1:1, pH 7.4)

All patents, applications, test methods, and publications mentioned herein are hereby incorporated by reference.

Many variations of the present invention will suggest themselves to those skilled in the art in light of the above detailed disclosure. For example, oral drug delivery entails crossing from the lumen of the gastrointestinal tract to the blood. This occurs as a result of crossing several cellular lipid bilayers that separate these anatomical compartments. The complexation of the perturbant with the active agent and the change in conformation of the active agent creates a supramolecular complex having physicochemical properties, such as, for example, solubility and conformation in space, which are different than those of either the perturbant or the active agent alone. This suggests that one can take advantage of this property to cross other membranes such as the blood-brain barrier, and ophthalmic, vaginal, rectal, and the like membranes. All such modifications are within the full extended scope of the appended claims.

What is claimed is:

1. A method for delivering, by the oral route, a biologically active agent to a subject in need of said biologically active agent, said method comprising:

(a) providing a biologically active agent which can exist in a native conformational state, a denatured conformational state, an d an intermediate conformational state which is reversible to said native state and is conformationally between said native and denatured states;

(b) exposing said biologically active agent to a complexing perturbant to reversibility transform said biologically active agent to said intermediate state and to form an orally deliverable supramolecular complex, said perturbant having a molecular weight between about 150 to about 600 daltons, and having at least one hydrophilic moiety and at least one hydrophobic moiety, said supramolecular complex comprising said perturbant non-covalently complexed with said biologically active agent, said biologically active agent not forming a microsphere with said perturbant, and said perturbant being present is in an amount effective for oral delivery of said biologically active agent; and (c) orally administering said supramolecular complex to said subject.

2. A method as defined in claim 1, further comprising (d) after said administering step, removing said perturbant from said supramolecular complex to transform said biologically active agent to said native state.

3. A method as defined in claim 2, wherein step (d) comprises diluting said supramolecular complex.

4. A method as defined in claim 1, wherein said intermediate state has a ΔG ranging from about −20 kcal/mole to about 20 kcal/moles relative to said native state.

5. A method as defined in claim 1, wherein said biologically active agent is selected from the group consisting of a peptide, a mucoopolysaccharide, a carbohydrate, a lipid, a pesticide, or any combination of the foregoing.

6. A method as defined in claim 5, wherein said biologically-active agent is selected from the group consisting of human growth hormone, bovine growth hormone, growth hormone-releasing hormone, an interferon, interleukin-II, insulin, heparin, calcitonin, erythropoietin, atrial naturetic factor, an antigen, a monoclonal antibody, somatostatin, adrenocorticotropin, gonadotropin releasing hormone, oxytocin, vasopressin, cromolyn sodium, vancomycin, desferrioxamine (DFO), or any combination of any of the foregoing.

7. A method as defined in claim 1, wherein said perturbant comprises a proteinoid.

8. A method as defined in claim 1, wherein said perturbant is selected from the group consisting of an acylated amino acid and an acylated poly amino acid.

9. A method as defined in claim 1, wherein said perturbant is selected from the group consisting of a sulfonated amino acid and a sulfonated poly amino acid.

10. A method as defined in claim 1, wherein said perturbant is selected from the group consisting of an acylated aldehyde of an amino acid and an acylated aldehyde of a poly amino acid.

11. A method as defined in claim 1, wherein said perturbant is selected from the group consisting of an acylated ketone of an amino acid and an acylated ketone of a poly amino acid.

12. A method as defined in claim 1, wherein said perturbant comprises a carboxylic acid having the formula

wherein R is $C_1$ to $C_{24}$ alkyl, $C_2$ to $C_{24}$ alkenyl, $C_3$ to $C_{10}$ cycloalkyl, $C_3$ to $C_{10}$ cycloalkenyl, phenyl, naphthyl, ($C_1$ to $C_{10}$ alkyl)phenyl, ($C_2$ to $C_{10}$ alkenyl)phenyl, ($C_1$ to $C_{10}$ alkyl)naphthyl, ($C_2$ to $C_{10}$ alkenyl)naphthyl, phenyl($C_1$ to $C_{10}$ alkyl), phenyl($C_2$ to $C_{10}$ alkenyl), naphthyl($C_1$ to $C_{10}$ alkyl) and naphthyl($C_2$ to $C_{10}$ alkenyl);

R being optionally substituted with $C_1$ to $C_{10}$ alkyl, $C_2$ to $C_{10}$ alkenyl, $C_1$ to $C_4$ alkoxy, —OH, —SH, —$CO_2R^1$, $C_3$ to $C_{10}$ cycloalkyl, $C_3$ to $C_{10}$ cycloalkenyl, heterocyclic having 3–10 ring atoms wherein the hetero atom is one or more atoms of N, O, S or any combination thereof, aryl, ($C_1$ to $C_{10}$ alkyl)aryl, aryl($C_1$ to $C_{10}$)alkyl, or any combination thereof;

R being optionally interrupted by oxygen, nitrogen, sulfur, or any combination thereof; and $R^1$ is hydrogen, $C_1$ to $C_4$ alkyl or $C_2$ to $C_4$ alkenyl; or a salt thereof.

13. A method for preparing an orally deliverable biologically active agent, said method comprising:
(a) providing a biologically active agent which can exist in a native conformational state, a denatured conformational state, and an intermediate conformational state which is reversible to said native state and is conformationally between said native and denatured states; and
(b) exposing said biologically active agent to a complexing perturbant to reversibility transform said biologically active agent to said intermediate state and to form an orally deliverable supramolecular complex,
said perturbant having a molecular weight ranging from about 150 to about 600 daltons, and having at least one hydrophilic moiety and at least one hydrophobic moiety,
said supramolecular complex comprising said perturbant non-covalently complexed with said biologically active agent,
said biologically active agent not forming a microsphere with said perturbant, and
said perturbant being present is in an amount effective for oral delivery of said biologically active agent.

14. A method as defined in claim 13, wherein said intermediate state has ΔG ranging from about −20 kcal/mole to about 20 kcal/moles relative to said native state.

15. A method as defined in claim 13, wherein said biologically active agent is selected from the group consisting of a peptide, a micropolysaccharide, a carbohydrate, a lipid, a pesticide, or any combination of the foregoing.

16. A method as defined in claim 15, wherein said biologically-active agent is selected from the group consisting of human growth hormone, bovine growth hormone, growth hormone-releasing hormone, an interferon, interleukin-II, insulin, heparin, calcitonin, erythropoietin, atrial naturetic factor, an antigen, a monoclonal antibody, somatostatin, adrenocorticotropin, gonadotropin releasing hormone, oxytocin, vasopressin, cromolyn sodium, vancomycin, desferrioxamine (DFO), or any combination of any of the foregoing.

17. A method as defined in claim 13, wherein said perturbant comprises a proteinoid.

18. A method as defined in claim 13, wherein said perturbant is selected from the group consisting of an acylated amino acid and an acylated poly amino acid.

19. A method as defined in claim 13, wherein said perturbant i s selected from the group consisting of a sulfonated amino acid and a sulfonated poly amino acid.

20. A method as defined in claim 13, wherein said perturbant is selected from the group consisting of an acylated aldehyde of an amino acid and an acylated aldehyde of a poly amino acid.

21. A method as defined in claim 13, wherein said perturbant is selected from the group consisting of an acylated ketone of an amino acid and an acylated ketone of a poly amino acid.

22. A method as defined in claim 13, wherein said perturbant comprises a carboxylic acid having the formula

wherein R is $C_1$ to $C_{24}$ alkyl, $C_2$ to $C_{24}$ alkenyl, $C_1$ to $C_{10}$ cycloalkyl, $C_3$ to $C_{10}$ cycloalkenyl, phenyl, naphthyl, ($C_1$ to $C_{10}$ alkyl)phenyl, ($C_2$ to $C_{10}$ alkenyl)phenyl, ($C_1$ to $C_{10}$ alkyl)naphthyl, ($C_2$ to $C_{10}$ alkenyl)naphthyl, phenyl($C_1$ to $C_{10}$ alkyl), phenyl($C_2$ to $C_{10}$ alkenyl), naphthyl($C_1$ to $C_{10}$ alkyl) and naphthyl($C_2$ to $C_{10}$ alkenyl);

R being optionally substituted with $C_1$ to $C_{10}$ alkyl, $C_2$ to $C_{10}$ alkenyl, $C_1$ to $C_4$ alkoxy, —OH, —SH, —$CO_2R^1$, $C_3$ to $C_{10}$ cycloalkyl, $C_3$ to $C_{10}$ cycloalkenyl, heterocyclic having 3–10 ring atoms wherein the hetero atom is one or more atoms of N, O, S or any combination thereof, aryl, ($C_1$ to $C_{10}$ alkyl)aryl, aryl($C_1$ to $C_{10}$)alkyl, or any combination thereof;

R being optionally interrupted by oxygen, nitrogen, sulfur, or any combination thereof; and $R^1$ is hydrogen, $C_1$ to $C_4$ alkyl or $C_2$ to $C_4$ alkenyl; or a salt thereof.

23. An oral delivery composition comprising
a supramolecular complex comprising:
(a) a biologically active agent in an intermediate conformational state non-covalently complexed with
(b) a complexing perturbant having a molecular weight ranging from about 150 to about 600 and having at least one hydrophilic moiety and at least one hydrophobic moiety;
wherein said intermediate state is reversible to said native state and is conformationally between a native conformational and a denatured conformational state of said biologically active agent and said composition is not a microsphere; and
said perturbant being present in an amount effective for oral delivery of said biologically active agent.

24. A composition as defined in claim 23, wherein said biologically active agent is selected from the group consisting of a peptide, a micropolysaccharide, a carbohydrate, a lipid, a pesticide, or any combination of the foregoing.

25. A composition as defined in claim 24, wherein said biologically-active agent is selected from the group consisting of human growth hormone, bovine growth hormone, growth hormone-releasing hormone, an interferon, interleukin-II, insulin, heparin, calcitonin, erythropoietin, atrial naturetic factor, an antigen, a monoclonal antibody, somatostatin, adrenocorticotropin, gonadotropin releasing hormone, oxytocin, vasopressin, cromolyn sodium, vancomycin, desferrioxamine (DFO), or any combination of any of the foregoing.

26. A composition as defined in claim 23, wherein said perturbant comprises a proteinoid.

27. A composition as defined in claim 23, wherein said perturbant is selected from the group consisting of an acylated amino acid and an acylated poly amino acid.

28. A composition as defined in claim 23, wherein said perturbant is selected from the group consisting of a sulfonated amino acid and a sulfonated poly amino acid.

29. A composition as defined in claim 23, wherein said perturbant is selected from the group consisting of an acylated aldehyde of an amino acid and an acylated aldehyde of a poly amino acid.

30. A composition as defined in claim 23, wherein said perturbant is selected from the group consisting of an acylated ketone of an amino acid and an acylated ketone of a poly amino acid.

31. A composition as defined in claim 23, wherein said perturbant comprises a carboxylic acid having the formula $$R-CO_2H$$

wherein R is $C_1$ to $C_{24}$ alkyl, $C_2$ to $C_{24}$ alkenyl, $C_3$ to $C_{10}$ cycloalkyl, $C_3$ to $C_{10}$ cycloalkenyl, phenyl, naphthyl, ($C_1$ to $C_{10}$ alkyl)phenyl, ($C_2$ to $C_{10}$ alkenyl)phenyl, ($C_1$ to $C_{10}$ alkyl)naphthyl, ($C_2$ to $C_{10}$ alkenyl)naphthyl, phenyl($C_1$ to $C_{10}$ alkyl), phenyl($C_2$ to $C_{10}$ alkenyl), naphthyl($C_1$ to $C_{10}$ alkyl) and naphthyl($C_2$ to $C_{10}$ alkenyl);

R being optionally substituted with $C_1$ to $C_{10}$ alkyl, $C_2$ to $C_{10}$ alkenyl, $C_1$ to $C_4$ alkoxy, —OH, —SH, —$CO_2R^1$, $C_3$ to $C_{10}$ cycloalkyl, $C_3$ to $C_{10}$ cycloalkenyl, heterocyclic having 3–10 ring atoms wherein the hetero atom is one or more atoms of N, O, S or any combination thereof, aryl, ($C_1$ to $C_{10}$ alkyl)aryl, aryl($C_1$ to $C_{10}$)alkyl, or any combination thereof;

R being optionally interrupted by oxygen, nitrogen, sulfur, or any combination thereof; and $R^1$ is hydrogen, $C_1$ to $C_4$ alkyl or $C_2$ to $C_4$ alkenyl; or a salt thereof.

32. An orally deliverable dosage unit form comprising:
(A) a composition as defined in claim 23; and
(B) (a) an excipient,
  (b) a diluent,
  (c) a disintegrant,
  (d) a lubricant,
  (e) a plasticizer,
  (f) a colorant,
  (g) a dosing vehicle, or
  (h) any combination thereof.

33. A method for preparing an agent which is capable of being delivered by the oral route to a subject in need of said agent, said method comprising:
(a) providing a biologically active agent which can exist in a native conformational state, a denatured conformational state, and an intermediate conformational state which is reversible to said native state and is conformationally between said native and denatured states;
(b) exposing said biologically active agent to a complexing perturbant to reversibly transform said biologically active agent to said intermediate state and to form an orally deliverable supramolecular complex,
  said perturbant having a molecular weight between about 150 and about 600 daltons, and having at least one hydrophilic moiety and one hydrophilic moiety,
  said supramolecular complex comprising said perturbant non-covalently complexed with said biologically active agent,
  said biologically active agent not forming a microsphere with said perturbant, and
said perturbant being present in an amount effective for oral delivery of said biologically active agent; and
(c) preparing a mimetic of said supramolecular complex.

34. A method as defined in claim 33, wherein said biologically active agent comprises a peptide and said mimetic comprises a peptide mimetic.

35. A method for preparing an agent which is capable of being delivered by the oral route to a subject in need of said agent, said method comprising:
(a) providing a biologically active agent which can exist in a native conformational state, a denatured conformational state, and an intermediate which is reversible to said native state and is conformationally between said native and denatured states;
(b) exposing said biologically active agent to a perturbant to reversibly transform said biologically active agent to said intermediate state, said perturbant being present in an amount effective for oral delivery of said biologically active agent; and
(c) preparing a mimetic of said intermediate state.

36. A method as defined in claim 35, wherein said perturbant comprises a pH changing agent, an ionic strength changing agent, or guanidine hydrochloride.

37. An orally deliverable composition comprising a mimetic of the orally deliverable composition prepared by the method of claim 13.

* * * * *

UNITED STATES PATENT AND TRADEMARK OFFICE
CERTIFICATE OF CORRECTION

PATENT NO.      : 6,348,207 B1
DATED           : February 19, 2002
INVENTOR(S)     : Milstein et al.

It is certified that error appears in the above-identified patent and that said Letters Patent is hereby corrected as shown below:

<u>Title page,</u>
Item [73], Assignee, delete "Emisiphere Technologies, Inc." and substitute
-- Emisphere Technologies, Inc. --

Signed and Sealed this

Eighth Day of April, 2003

JAMES E. ROGAN
*Director of the United States Patent and Trademark Office*

UNITED STATES PATENT AND TRADEMARK OFFICE
CERTIFICATE OF CORRECTION

PATENT NO.   : 6,348,207 B1
DATED        : February 19, 2002
INVENTOR(S)  : Sam J. Milstein et al.

It is certified that error appears in the above-identified patent and that said Letters Patent is hereby corrected as shown below:

<u>Title page,</u>
Item [73], Assignee, should read -- Emisphere Technologies, Inc. --

Signed and Sealed this

First Day of July, 2003

JAMES E. ROGAN
*Director of the United States Patent and Trademark Office*